US011331348B2

(12) United States Patent
Chen et al.

(10) Patent No.: US 11,331,348 B2
(45) Date of Patent: May 17, 2022

(54) COMPOSITIONS COMPRISING EXTRACELLULAR MATRIX OF PRIMITIVE ANIMAL SPECIES AND RELATED METHODS

(71) Applicant: University of Pittsburgh—Of the Commonwealth System of Higher Education, Pittsburgh, PA (US)

(72) Inventors: Chien-Wen Chen, Somerville, MA (US); Yadong Wang, Bradford Woods, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 432 days.

(21) Appl. No.: 16/096,400

(22) PCT Filed: Apr. 28, 2017

(86) PCT No.: PCT/US2017/030096
§ 371 (c)(1),
(2) Date: Oct. 25, 2018

(87) PCT Pub. No.: WO2017/189986
PCT Pub. Date: Nov. 2, 2017

(65) Prior Publication Data
US 2019/0134103 A1    May 9, 2019

Related U.S. Application Data

(60) Provisional application No. 62/328,829, filed on Apr. 28, 2016.

(51) Int. Cl.
| | |
|---|---|
| *A61K 35/583* | (2015.01) |
| *A61K 35/616* | (2015.01) |
| *A61K 35/618* | (2015.01) |
| *A61L 27/36* | (2006.01) |
| *A61K 35/62* | (2006.01) |
| *A61K 35/646* | (2015.01) |
| *A61K 35/12* | (2015.01) |
| *A61K 35/63* | (2015.01) |
| *A61K 35/64* | (2015.01) |
| *A61K 35/60* | (2006.01) |
| *A61L 27/50* | (2006.01) |
| *A61K 35/36* | (2015.01) |
| *C12N 5/00* | (2006.01) |

(52) U.S. Cl.
CPC ............ *A61K 35/60* (2013.01); *A61K 35/12* (2013.01); *A61K 35/36* (2013.01); *A61K 35/583* (2013.01); *A61K 35/616* (2013.01); *A61K 35/618* (2013.01); *A61K 35/62* (2013.01); *A61K 35/63* (2015.01); *A61K 35/64* (2013.01); *A61K 35/646* (2013.01); *A61L 27/3604* (2013.01); *A61L 27/3633* (2013.01); *A61L 27/3687* (2013.01); *A61L 27/3691* (2013.01); *A61L 27/50* (2013.01); *C12N 5/0068* (2013.01); *A61L 2400/06* (2013.01); *A61L 2430/40* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 4,902,508 | A | 2/1990 | Badylak et al. |
| 4,956,178 | A | 9/1990 | Badylak et al. |
| 5,281,422 | A | 1/1994 | Badylak et al. |
| 5,352,463 | A | 10/1994 | Badylak et al. |
| 5,372,821 | A | 12/1994 | Badylak et al. |
| 5,554,389 | A | 9/1996 | Badylak et al. |
| 5,573,784 | A | 11/1996 | Badylak et al. |
| 5,645,860 | A | 7/1997 | Knapp, Jr. et al. |
| 5,753,267 | A | 5/1998 | Badylak et al. |
| 5,762,966 | A | 6/1998 | Knapp, Jr. et al. |
| 5,771,969 | A | 6/1998 | Garay |
| 5,866,414 | A | 2/1999 | Badylak et al. |
| 6,099,567 | A | 8/2000 | Badylak et al. |
| 6,485,723 | B1 | 11/2002 | Badylak et al. |
| 6,576,265 | B1 | 6/2003 | Spievack |
| 6,579,538 | B1 | 6/2003 | Spievack |
| 6,696,270 | B2 | 2/2004 | Badylak et al. |
| 6,783,776 | B2 | 8/2004 | Spievack |
| 6,793,939 | B2 | 9/2004 | Badylak |
| 6,849,273 | B2 | 2/2005 | Spievack |

(Continued)

FOREIGN PATENT DOCUMENTS

| | | |
|---|---|---|
| WO | 2005009497 A1 | 2/2005 |
| WO | 2011042794 A2 | 4/2011 |

(Continued)

OTHER PUBLICATIONS

Reckers LJ, Fagundes DJ, Cohen M, Raymundo JLP, Moreira MB, Paiva VC. Medial meniscus transplantation using cyanoacrylate in rabbits. Acta Cir Bras. [serial on the Internet] Mar.-Apr. 2006;21(2). (Year: 2006).*
Akhtar et al., "Activation of EGFR/ERBB2 via Pathways Involving ERK1/2, P38 MAPK, AKT and FOXO Enhances Recovery of Diabetic Hearts from Ischemia-Reperfusion Injury", PLoS ONE, 2012, vol. 7, Issue 6, Article No. e39066.
Ali et al., "Existing cardiomyocytes generate cardiomyocytes at a low rate after birth in mice", Proceedings of the National Academy of Sciences, 2014, pp. 8850-8855, vol. 111, No. 24.
Badylak, "Decellularized Allogeneic and Xenogeneic Tissue as a Bioscaffold for Regenerative Medicine: Factors that Influence the Host Response", Annals of Biomedical Engineering, 2014, pp. 1517-1527, vol. 42, No. 7.
Bergmann et al., "Evidence for Cardiomyocyte Renewal in Humans", Science, 2009, pp. 98-102, vol. 324.

(Continued)

*Primary Examiner* — Allison M Fox
(74) *Attorney, Agent, or Firm* — The Webb Law Firm

(57) ABSTRACT

A method is provided for preparing an ECM material, including an ECM gel, from regenerative or regenerating tissue. ECM material prepared from regenerative or regenerating materials also is provided.

14 Claims, 28 Drawing Sheets

(56) References Cited

U.S. PATENT DOCUMENTS

| | | | |
|---|---|---|---|
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 8,361,503 B2 | 1/2013 | Badylak et al. | |
| 8,613,957 B2 | 12/2013 | Sigurjonsson et al. | |
| 8,637,067 B1 * | 1/2014 | Sun | A61L 26/0057 424/426 |
| 9,072,816 B2 | 7/2015 | Matheny | |
| 9,814,744 B2 | 11/2017 | Badylak et al. | |
| 10,617,790 B2 † | 4/2020 | Early | |
| 2005/0013870 A1 | 1/2005 | Freyman et al. | |
| 2010/0152852 A1 * | 6/2010 | Ingham | A61L 27/3683 623/14.12 |
| 2010/0226895 A1 | 9/2010 | Boruch | |
| 2011/0151011 A1 * | 6/2011 | Flynn | A61P 17/02 424/490 |
| 2011/0244054 A1 * | 10/2011 | Sigurjonsson | A61L 15/40 424/572 |
| 2014/0356331 A1 | 12/2014 | Badylak et al. | |

FOREIGN PATENT DOCUMENTS

| | | | | |
|---|---|---|---|---|
| WO | 2011087743 A2 | 7/2011 | | |
| WO | 2013009595 A2 | 1/2013 | | |
| WO | 2014046752 A1 | 3/2014 | | |
| WO | WO 14/110269 | * | 7/2014 | A61K 35/56 |

OTHER PUBLICATIONS

Bersell et al., "Neuregulin1/ErbB4 Signaling Induces Cardiomyocyte Proliferation and Repair of Heart Injury", Cell, 2009, pp. 257-270, vol. 138.
Bonfanti, "From Hydra Regeneration to Human Brain Structural Plasticity: A Long Trip through Narrowing Roads", Scientific World Journal, 2011, pp. 1270-1299, vol. 11.
Bowers et al., "The extracellular matrix: At the center of it all", Journal of Molecular and Cellular Cardiology, 2010, pp. 474-482, vol. 48.
Brockes et al., "Comparative Aspects of Animal Regeneration" Annual Review of Cell and Developmental Biology, 2008, pp. 525-549, vol. 24.
Chen et al., "Human Pericytes for Ischemic Heart Repair", Stem Cells, 2013, pp. 305-316, vol. 31.
Chen et al., "Controlled dual delivery of fibroblast growth factor-2 and Interleukin-10 by heparin-based coacervate synergistically enhances ischemic heart repair", Biomaterials, 2015, pp. 138-151, vol. 72.
Chen et al., "Human Myocardial Pericytes: Multipotent Mesodermal Precursors Exhibiting Cardiac Specificity", Stem Cells, 2015, pp. 557-573, vol. 33.
Chen et al., "Decellularized zebrafish cardiac extracellular matrix induces mammalian heart regeneration", Science Advances, 2016, 16 pages, vol. 2, Article No. e1600844.
Chu et al., "The effect of a heparin-based coacervate of fibroblast growth factor-2 on scarring in the infarcted myocardium", Biomaterials, 2013, pp. 1747-1756, vol. 34.
Clause et al., "Extracellular matrix signaling in morphogenesis and repair", Current Opinion in Biotechnology, 2013, pp. 830-833, vol. 24.
Cote et al., "ERBB2 Inhibition and Heart Failure", The New England Journal of Medicine, 2012, pp. 2150-2153, vol. 367, No. 22.
Crone et al., "ErbB2 is essential in the prevention of dilated cardiomyopathy", Nature Medicine, 2002, pp. 459-465, vol. 8, No. 5.
D'Uva et al., "ERBB2 triggers mammalian heart regeneration by promoting cardiomyocyte dedifferentiation and proliferation", Nature Cell Biology, 2015, pp. 627-638, vol. 17, No. 5.
D'Uva et al., "The key roles of ERBB2 in cardiac regeneration", Cell Cycle, 2015, pp. 2383-2384, vol. 14, No. 15.
Daley et al., "ECM-modulated cellular dynamics as a driving force for tissue morphogenesis", Current Opinion in Genetics & Development, 2013, 408-414, vol. 23.
Drenckhahn et al., "Compensatory Growth of Healthy Cardiac Cells in the Presence of Diseased Cells Restores Tissue Homeostasis during Heart Development", Developmental Cell, 2008, pp. 521-533, vol. 15.
Foglia et al., "Building and re-building the heart by cardiomyocyte proliferation", Development, 2016, pp. 729-740, vol. 143.
Force et al., "Molecular mechanisms of cardiotoxicity of tyrosine kinase inhibition", Nature Reviews Cancer, 2007, pp. 332-344, vol. 7.
Gemberling et al., "Nrg1 is an injury-induced cardiomyocyte mitogen for the endogenous heart regeneration program in zebrafish.", eLife, 2015, 17 pages, vol. 4, Article No. e05871.
Gilbert, "Strategies for Tissue and Organ Decellularization", Journal of Cellular Biochemistry, 2012, pp. 2217-2222, vol. 113.
Godwin et al., "Extracellular matrix considerations for scar-free repair and regeneration: Insights from regenerative diversity among vertebrates", The International Journal of Biochemistry & Cell Biology, 2014, pp. 47-55, vol. 56.
Guedelhoefer et al., "Planarian Immobilization, Partial Irradiation, and Tissue Transplantation", Journal of Visualized Experiments, 2012, 7 pages, vol. 66, Article No. e4015.
Handorf et al., "Tissue Stiffness Dictates Development, Homeostasis, and Disease Progression", Organogenesis, 2015, pp. 1-15, vol. 11, No. 1.
He et al., "Comparison of Methods for Whole-Organ Decellularization in Tissue Engineering of Bioartificial Organs", Tissue Engineering Part B: Reviews, 2013, pp. 194-208, vol. 19, No. 3.
Hoshiba et al., "Decellularized matrices for tissue engineering", Expert Opinion on Biological Therapy, 2010, pp. 1717-1728, vol. 10, No. 12.
Janson et al., "Extracellular matrix elasticity and topography: Material-based cues that affect cell function via conserved mechanisms", Journal of Biomedical Materials Research Part A. 2015, pp. 1246-1258, vol. 103A.
Kikuchi et al., "Cardiac Regenerative Capacity and Mechanisms", Annual Review of Cell and Developmental Biology, 2012, pp. 719-741, vol. 28.
Lafontant et al., "Cardiac Myocyte Diversity and a Fibroblast Network in the Junctional Region of the Zebrafish Heart Revealed by Transmission and Serial Block-Face Scanning Electron Microscopy", PLoS ONE, 2013, 12 pages, vol. 8, Issue 8, Article No. e72388.
Li et al., "Elastin is an essential determinant of arterial morphogenesis", Nature, 1998, pp. 276-280, vol. 393.
Lubinski et al., "Speckle Tracking Methods for Ultrasonic Elasticity Imaging Using Short-Time Correlation", IEEE Transactions on Ultrasonics, Ferroelectrics, and Frequency Control, 1999, pp. 82-96, vol. 46, No. 1.
Missinato et al., "Extracellular component hyaluronic acid and its receptor Hmmr are required for epicardial EMT during heart regeneration", Cardiovascular Research, 2015, pp. 487-498, vol. 107.
Miyagawa et al., Estrogen-independent activation of erbBs signaling and estrogen receptor α in the mouse vagina exposed neonatally to diethylstilbestrol. Oncogene. 2004;23:340-9.
Mollova et al., "Cardiomyocyte proliferation contributes to heart growth in young humans", PNAS, 2013, pp. 1446-1451, vol. 110, No. 4.
Naqvi et al., "A Proliferative Burst during Preadolescence Establishes the Final Cardiomyocyte Number", Cell, 2014, pp. 795-807, vol. 157.
O'Donnell et al., "Internal Displacement and Strain Imaging Using Ultrasonic Speckle Tracking", IEEE Transactions on Ultrasonics, Ferroelectrics, and Frequency Control, 1994, pp. 314-325, vol. 41, No. 3.
Okada et al., "Differential efficacy of gels derived from small intestinal submucosa as an injectable biomaterial for myocardial infarct repair", Biomaterials, 2010, pp. 7678-7683, vol. 31.

(56) References Cited

OTHER PUBLICATIONS

Osherov et al., "Selective Inhibition of the Epidermal Growth Factor and HER2/Neu Receptors by Tyrphostins", Journal of Biological Chemistry. 1993;268:11134-42.
Polizzotti et al., "Neuregulin stimulation of cardiomyocyte regeneration in mice and human myocardium reveals a therapeutic window", Science Translational Medicine, 2015, 15 pages, vol. 7, Issue 281, Article No. 281ra45.
Pollick et al., "Echocardiographic and Cardiac Doppler Assessment of Mice" Journal of the American Society of Echocardiography, 1995, pp. 602-610, vol. 8.
Porrello et al., "Transient Regenerative Potential of the Neonatal Mouse Heart", Science, 2011, pp. 1078-1080, vol. 331.
Poss et al., "Heart Regeneration in Zebrafish", Science, 2002, pp. 2188-2190, vol. 298.
Qiu et al., "A role for matrix stiffness in the regulation of cardiac side population cell function", American Journal of Physiology Heart and Circulatory Physiology, 2015, pp. H990-H997, vol. 308.
Roosens et al., "Impact of Detergent-Based Decellularization Methods on Porcine Tissues for Heart Valve Engineering", Annals of Biomedical Engineering, 2016:1-13.
Sarras Jr., "Components, structure, biogenesis and function of the Hydra extracellular matrix in regeneration, pattern formation and cell differentiation", The International Journal of Developmental Biology, 2012, pp. 567-576, vol. 56.
Seif-Naraghi et al., "Safety and Efficacy of an Injectable Extracellular Matrix Hydrogel for Treating Myocardial Infarction", Science Translational Medicine, 2013, 12 pages, vol. 5, Issue 173, Article No. 173ra25.
Senyo et al., "Mammalian heart renewal by pre-existing cardiomyocytes", Nature, 2013, pp. 433-436, vol. 493.
Singelyn et al., "Injectable Materials for the Treatment of Myocardial Infarction and Heart Failure: The Promise of Decellularized Matrices", Journal of Cardiovascular Transplant Research, 2010, pp. 478-486, vol. 3.
Sonnenberg et al., "Delivery of an engineered HGF fragment in an extracellular matrix-derived hydrogel prevents negative LV remodeling post-myocardial infarction", Biomaterials, 2015, pp. 56-63, vol. 45.
Sturzu et al., "Fetal Mammalian Heart Generates a Robust Compensatory Response to Cell Loss", Circulation, 2015, pp. 109-121, vol. 132.
Uygur et al., "Mechanisms of Cardiac Regeneration", Developmental Cell, 2016, pp. 362-374, vol. 36.
Valiente-Alandi et al., "Extracellular matrix-mediated cellular communication in the heart", Journal of Molecular and Cellular Cardiology, 2016, pp. 228-237, vol. 91.
Walsh et al., "Cardiomyocyte cell cycle control and growth estimation in vivo—an analysis based on cardiomyocyte nuclei", Cardiovascular Research, 2010, pp. 365-373, vol. 86.
Wandt et al., "Echocardiographic assessment of ejection fraction in left ventricular hypertrophy", Heart, 1999, pp. 192-198, vol. 82.
Wang et al., "Fibronectin is deposited by injury-activated epicardial cells and is necessary for zebrafish heart regeneration", Developmental Biology, 2013, pp. 427-435, vol. 382, No. 2.
Wassenaar et al., Evidence for Mechanisms Underlying the Functional Benefits of a Myocardial Matrix Hydrogel for Post-MI Treatment. Journal of the American College of Cardiology 2016;67:1074-86.
Watt et al., "Role of the extracellular matrix in regulating stem cell fate", Nature Reviews Molecular Cell Biology, 2013, pp. 467-473, vol. 14.
Yates et al., "Skin Wound Healing and Scarring: Fetal Wounds and Regenerative Restitution", Birth Defects Research Part C: Embryo Today: Reviews, 2012, pp. 325-333, vol. 96, No. 4.
Yutzey, "Regenerative biology: Neuregulin 1 makes heart muscle", Nature, 2015, 445-446, vol. 520.
Zacchigna et al., "Extra- and intracellular factors regulating cardiomyocyte proliferation in postnatal life", Cardiovascular Research, 2014, pp. 312-320, vol. 102.
Hong et al., "Tailoring the degradation kinetics of poly(ester carbonate urethane)urea thermoplastic elastomers for tissue engineering scaffolds", Biomaterials, 2010, pp. 4249-4258, vol. 31.
Satoh, et al., "Collagen Reconstitution is Inversely Correlated with Induction of Limb Regeneration in Ambystoma mexicanum", Zoological Science, 29(3):191-197, (2012).†

\* cited by examiner
† cited by third party

A

Healthy Heart 1D post Amputation 3D post Amputation

B

Note: * For hzECM only

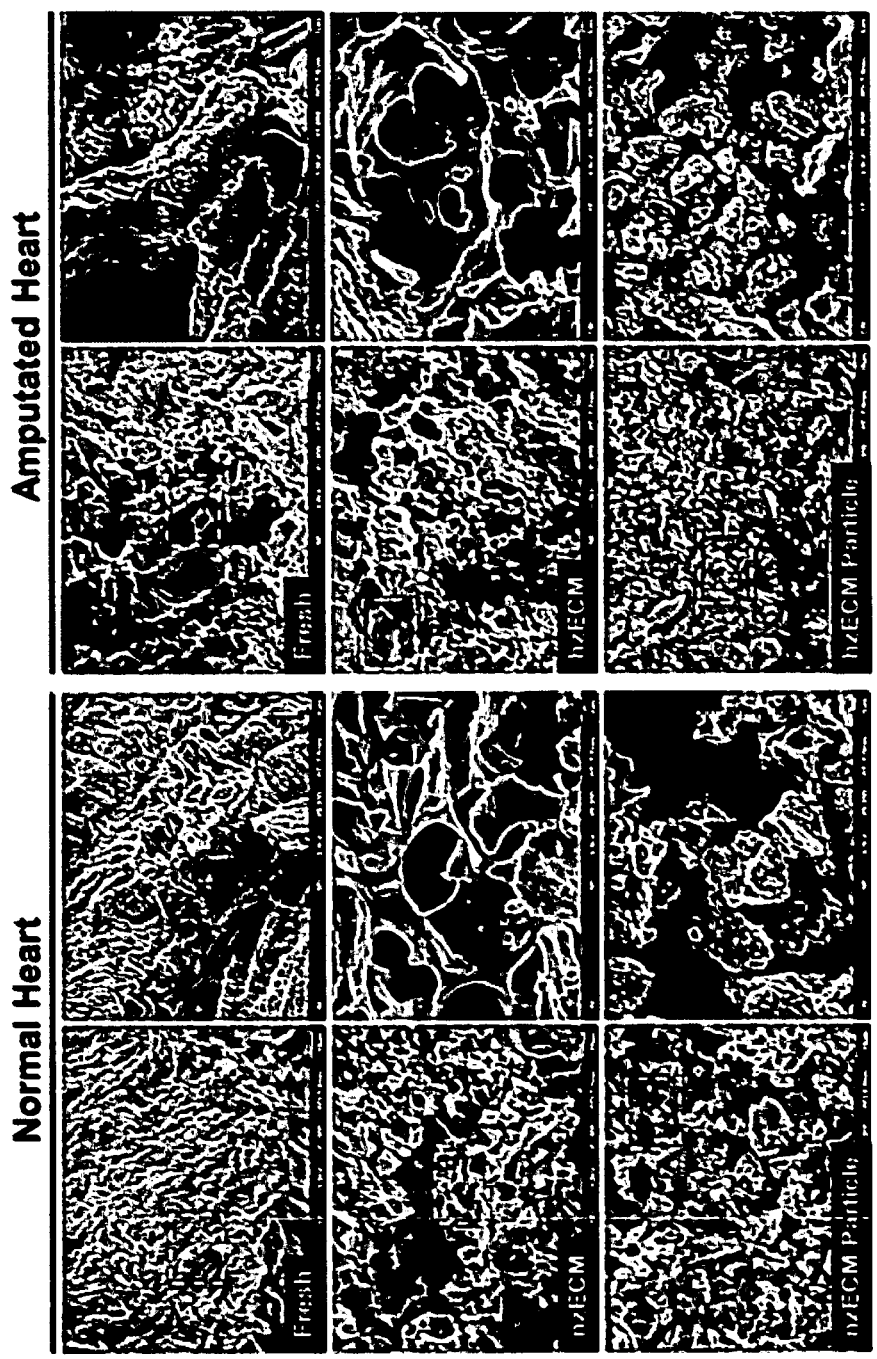

| ECM Composition | mECM | nzECM |
|---|---|---|
| Collagen (μg/mg) | 408.8±25.81 | 299.1±32.05** |
| Elastin (μg/mg) | 45.7±9.51 | 62.67±9.07* |
| GAGs (μg/mg) | 2.35±0.58 | 3.34±0.61* |

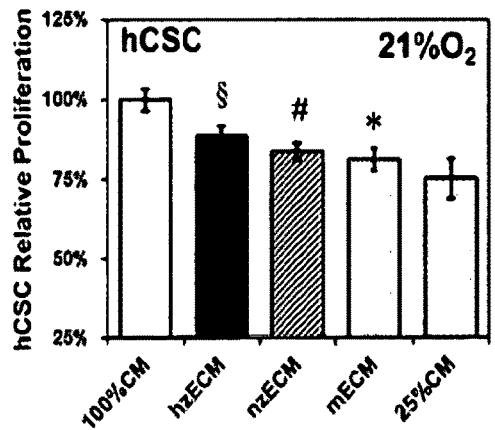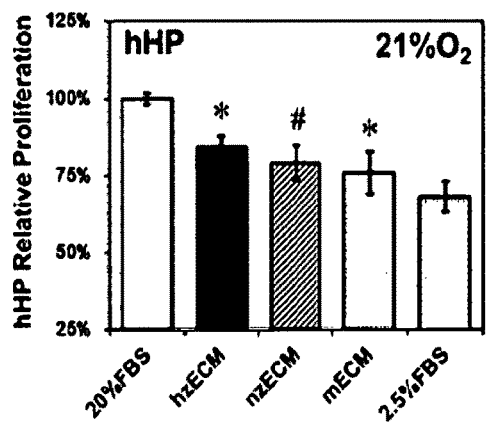
Fig. 3A     Fig. 3B
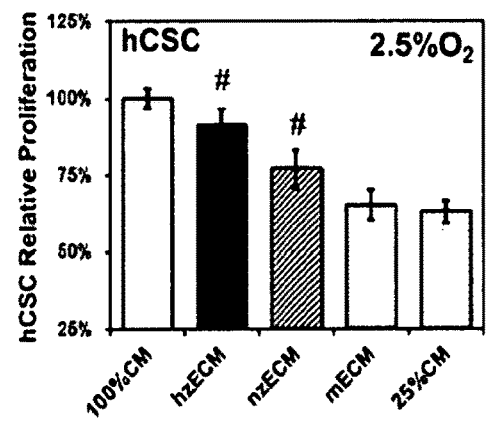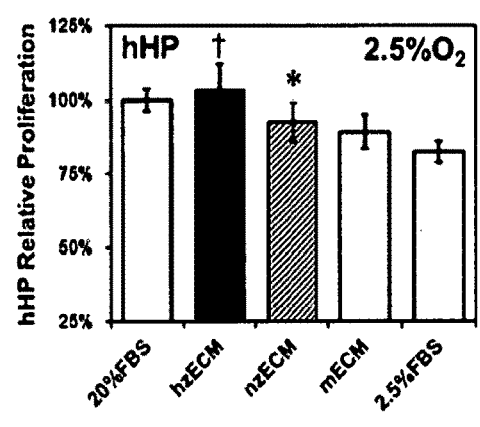
Fig. 3C     Fig. 3D
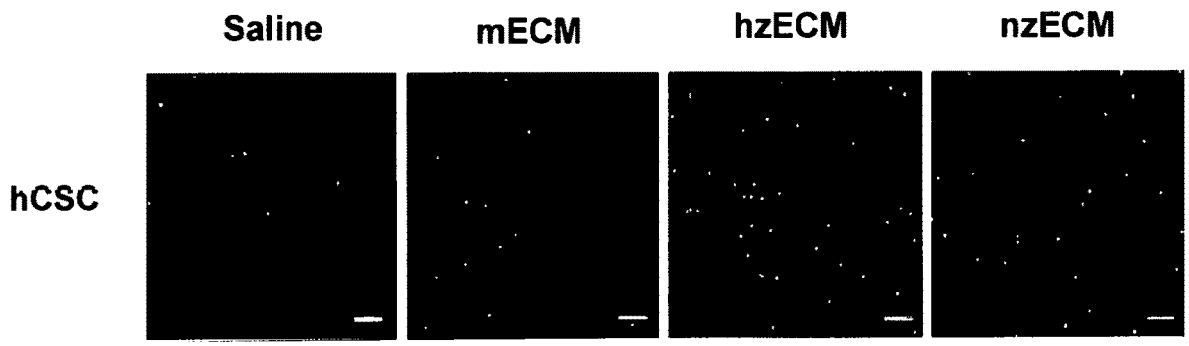
Fig. 3E

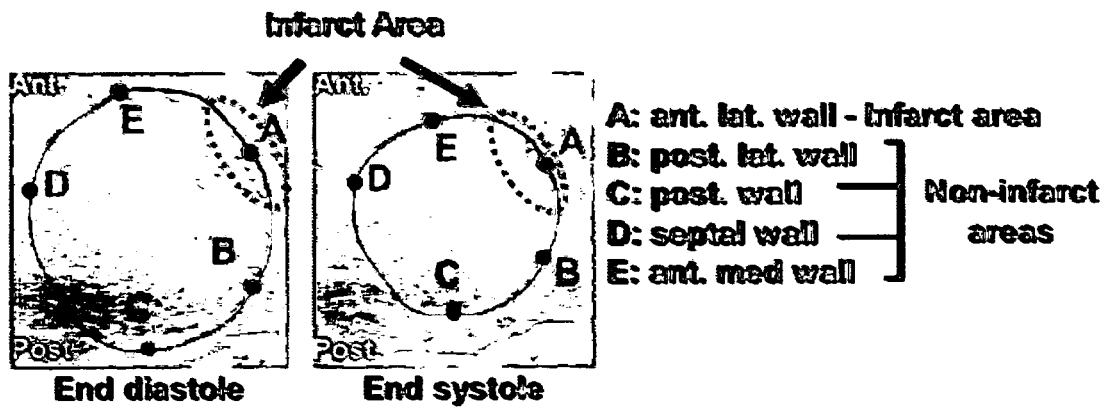
Fig. 6A
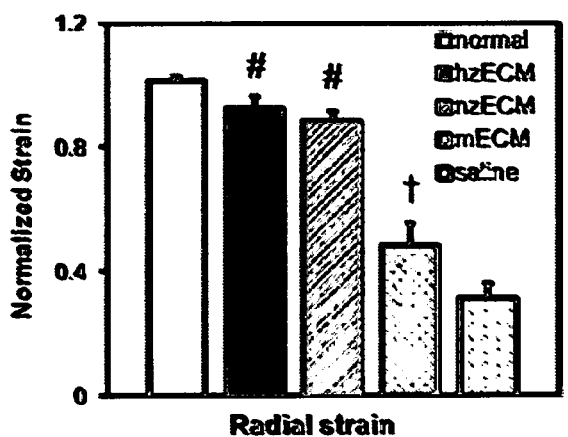
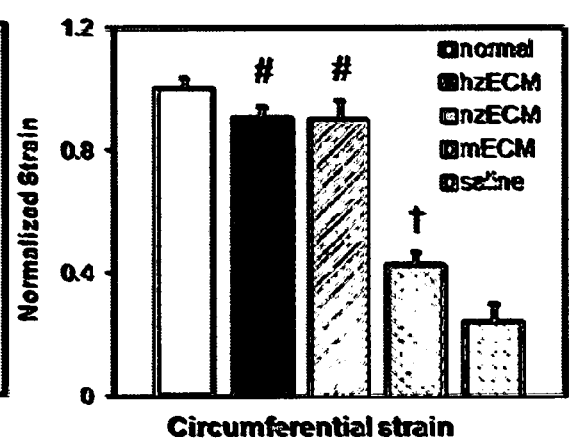
Fig. 6C  Fig. 6D

COMPOSITIONS COMPRISING EXTRACELLULAR MATRIX OF PRIMITIVE ANIMAL SPECIES AND RELATED METHODS

CROSS REFERENCE TO RELATED APPLICATIONS

This application is the United States national phase of International Application No. PCT/US2017/030096 filed Apr. 28, 2017, and claims the benefit of United States Provisional Patent Application No. 62/328,829, filed Apr. 28, 2016, each of which is incorporated herein by reference in its entirety.

The extracellular matrix (ECM) is the architectural foundation of tissue morphogenesis, development, homeostasis, and regeneration across the animal kingdom. Evolutionarily primitive species generally have higher regenerative capability than mammals; the ECM may contribute to this difference.

To date, faithful regeneration of non-regenerative tissues, such as damaged myocardium, has not been achieved. The general field of regenerative medicine has focused on use of either generic ECM material, such as decellularized porcine UBM (urinary bladder matrix) or SIS (small intestine submucosa), or organ-specific ECM, such as using CNS or nerve-derived ECM for nerve regeneration or cardiac-derived ECM for heart repair. While some success has been achieved, regeneration and/or faithful regeneration of many tissues has not been achieved. There remains a great need for a cell growth matrix that promotes faithful tissue growth for repair of damaged or defective tissues.

SUMMARY

Provided herein are regenerative ECM (rECM) compositions and methods useful for tissue regeneration that use rECM. ECM material prepared from regenerating, developing or rapidly-growing tissue is shown herein to promote regeneration of normal, differentiated tissue in tissues that have previously been difficult to regenerate.

According to one aspect, a method of producing regenerative extracellular matrix (rECM) composition is provided. The method comprises: freezing and thawing tissue that has inherent regenerative capability or that is undergoing regeneration, growth, or development, to kill cells within the tissue; treating the thawed tissue with one or more nucleases to digest nucleic acids in the tissue to produce rECM; and washing the nuclease-digested tissue in an aqueous solution, to remove cellular debris. An rECM product, such as an rECM prepared according to the method, also is provided in one aspect.

According to another aspect of the invention, a method of treating a patient having a tissue injury, condition or defect is provided. The method comprises administering to the patient an amount of an rECM composition to the patient at a location in the patient of tissue injury, condition or defect, in an amount effective to treat the tissue injury, condition or defect in the patient.

In a further aspect of the invention, a medical device or apparatus is provided comprising or coated with an rECM material as described herein.

In yet another aspect of the invention, a method of preparing an rECM gel material is provided. The method comprises neutralizing an acid protease-digested material that is prepared by: a. freezing and thawing tissue that has inherent regenerative capability or that is undergoing regeneration, growth, or development, to kill cells within the tissue; b. treating the thawed tissue with one or more nucleases to digest nucleic acids in the tissue to produce rECM; c. washing the nuclease-digested tissue in an aqueous solution, to remove cellular debris; d. digesting the nuclease-digested tissue with an acid protease; and e. optionally freezing or lyophilizing the acid protease-digested material.

A kit is provided according to a further aspect of the invention. The kit comprises rECM or rECM combined with other materials contained in a vessel, wherein the rECM is optionally prepared according to a method provided herein.

BRIEF DESCRIPTION OF THE DRAWINGS

(FIG. 1A) Representative images of zebrafish hearts: (a) healthy, (b) 1-day, and (c) 3-day post amputation. Roughly 70% of the ventricular tissue (dotted lines), including the regenerating area in the amputated heart, is harvested. (FIG. 1B) The work flow of production of decellularized zebrafish heart ECM.

FIGS. 2A-2C. Characterization of decellularized zebrafish cardiac ECM (zECM). (FIG. 2A) Scanning electron microscopic images of fresh, decellularized, and ground decellularized normal and healing (3 dpa) zebrafish ventricular tissues. 1000× images, scale bar=10 µm; 5000× images, scale bar=1 µm. (FIG. 2B) Particle size analysis of ground zECM by dynamic light scattering (N=3). (FIG. 2C) Composition analyses of normal zebra fish cardiac ECM (nzECM) and adult mouse cardiac ECM (mECM) showing the amount of collagen, elastin, and glycosaminoglycans (GAGs) in each group respectively (N=3 per group; data showing means±SD; *p<0.05, **p<0.01).

(FIGS. 3A-D) Relative proliferation rates of hCSC and hHP under stressed culture conditions following different cardiac ECM treatments. Addition of hzECM, nzECM, or mECM in the culture media partially rescued the proliferation of (FIG. 3A) hCSC and (FIG. 3B) hHP under nutrient-deprived culture conditions. Addition of hzECM or nzECM, but not mECM, in the culture media partially rescued the proliferation of (FIG. 3C) hCSC and (FIG. 3D) hHP under dual hypoxic (2.5% $O_2$) and nutrient-deprived culture conditions. (*p≤0.05, ‡p≤0.01, § p≤0.005, #p≤0.001 compared to nutrient-deprived controls in all graphs) (FIG. 3E-H) Transwell chemotaxis assays with different cardiac ECM showing the migration of hCSC and hHP under nutrient-deprived culture conditions. hzECM and nzECM, but not mECM, induced prominent migration of (FIG. 3E) hCSC and (FIG. 3G) hHP (cells stained in green in original; scale bars=50 µm). Significantly more (FIG. 3F) hCSC and (FIG. 3H) hHP migrated in hzECM- and nzECM-induced groups than in the mECM-induced group and saline control (N=4 per group; data normalized to the respective saline control; p<0.01, *p<0.001 compared to mECM and saline; #p<0.05 hzECM vs nzECM). All quantitative data represent means±SD.

(FIG. 4A) Schematic representation of the work flow using zECM (0.5 mg suspension) for mammalian heart regeneration after acute MI (dpa: day post amputation). Cardiac contractile function is indicated by (FIG. 4B) fractional area change and (FIG. 4C) ejection fraction; left ventricular dimension is indicated by (FIG. 4D) end-diastolic area and (FIG. 4E) end-systolic area (N=7 per group;

data analyzed by two-way repeated ANOVA; *p≤0.05, ‡p≤0.01, § p≤0.005, #p≤0.001 compared to saline controls in all graphs).

Figure 5A:
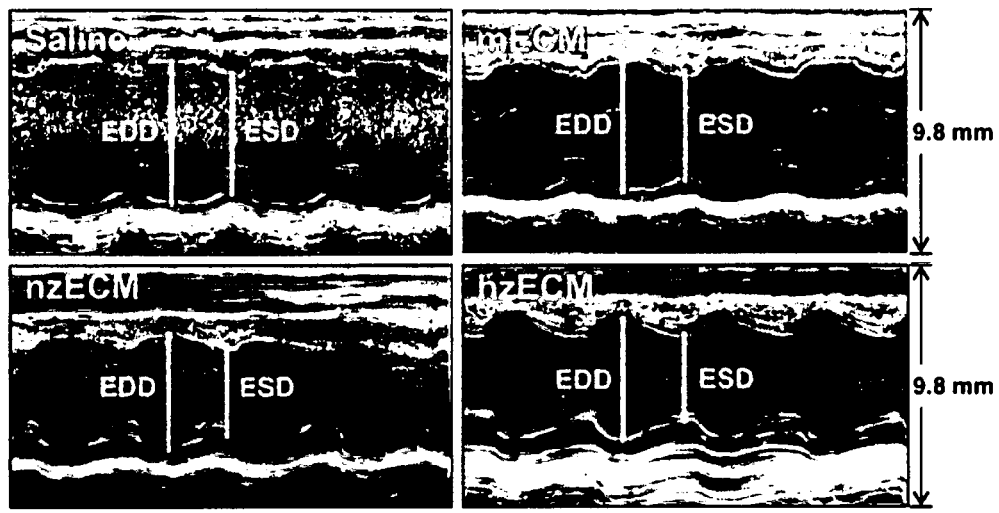
Figure 5B:
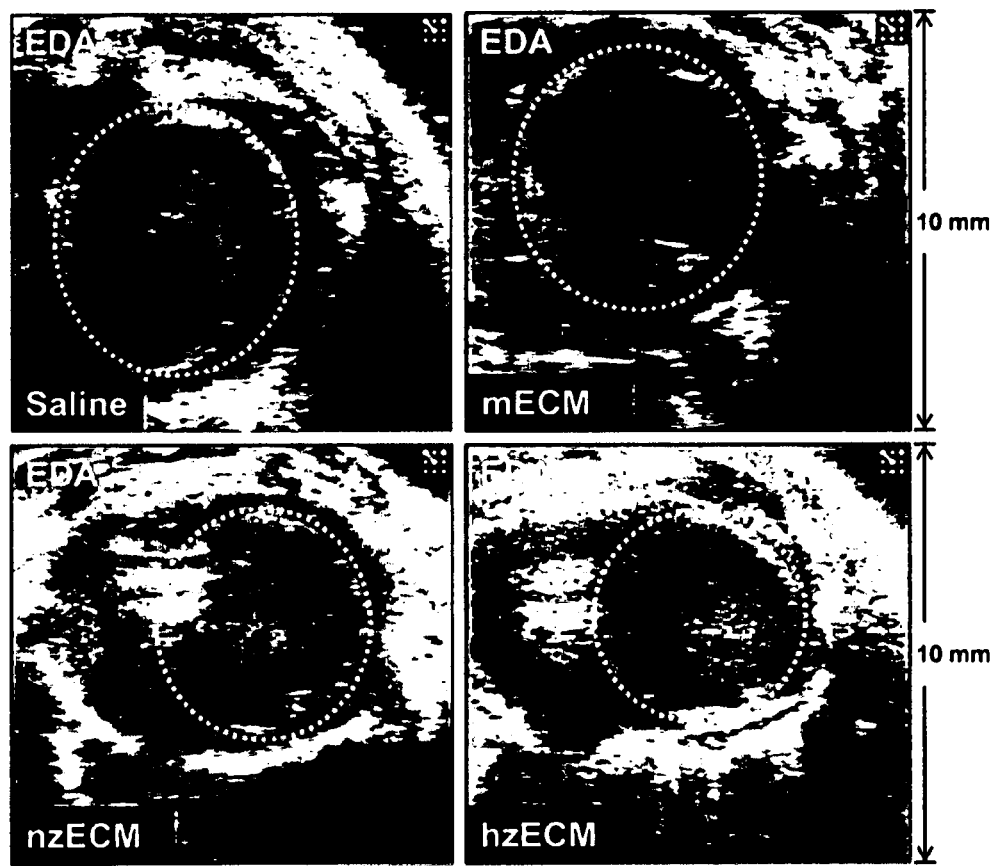

FIGS. 5A and 5B. Representative left ventricular images of (FIG. 5A) M- and (B) B-mode echocardiography. End-systolic dimension (ESD) and end-diastolic dimension (EDD) are indicated in (FIG. 5A). Dotted circles in (FIG. 5B) approximate the left ventricular wall at the end-diastole.

FIGS. 6A-6D. (FIG. 6A) Representative B-mode images showing region-of-interest (ROI) selection at end-diastole and end-systole for myocardial strain analysis. (FIG. 6B) Representative graphs showing radial (upper panels) and circumferential (lower panels) strain estimation during a cardiac cycle: strain of the infarcted area (dark blue in original) is closer to the non-infarcted area (yellow, green, red and cyan in original) and normal heart in hzECM-treated group than in mECM- or saline-treated groups. Quantification of (FIG. 6C) radial and (FIG. 6D) circumferential strain (N=3 per group; ‡p≤0.01, #p≤0.001 hzECM and nzECM compared to mECM and saline while mECM compared to saline in all graphs).

Figure 7A:
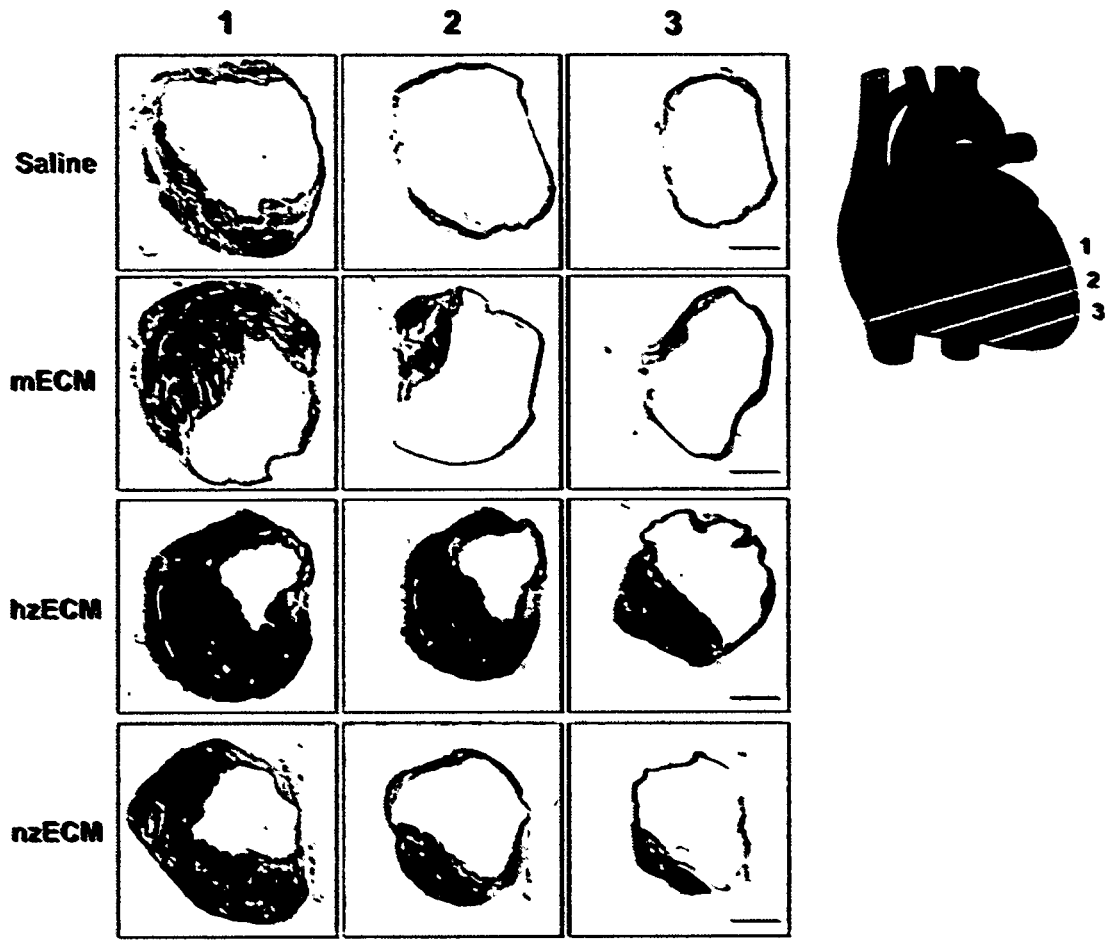
Figure 7B:
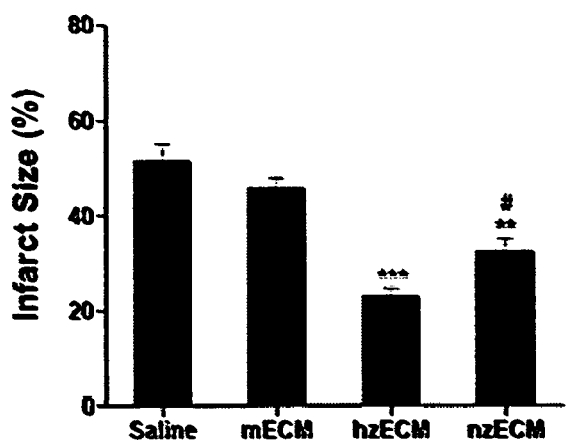
Figure 7C:
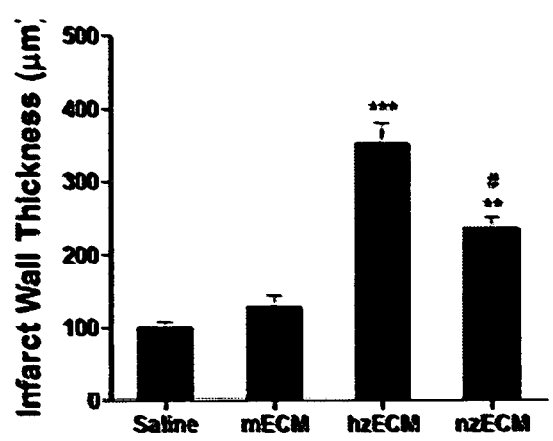

FIGS. 7A-7C. Histological analysis of mouse hearts after zECM treatment. (FIG. 7A) Representative H&E staining images of serially sectioned mouse hearts at 6 weeks post-MI. 1, 2, and 3 approximate the section level in the model heart (scale bars=1 mm). (FIG. 7B) Analysis of the infarct size with H&E stained sections at level 1 (N=4 per group). (FIG. 7C) Analysis of the left ventricular wall thickness with H&E stained sections at level 1 (N=4 per group). p<0.01, *p<0.001 compared to mECM and saline; #p<0.05 hzECM vs nzECM). All quantitative data represent means±SD.

Figure 8A:
Figure 8B:
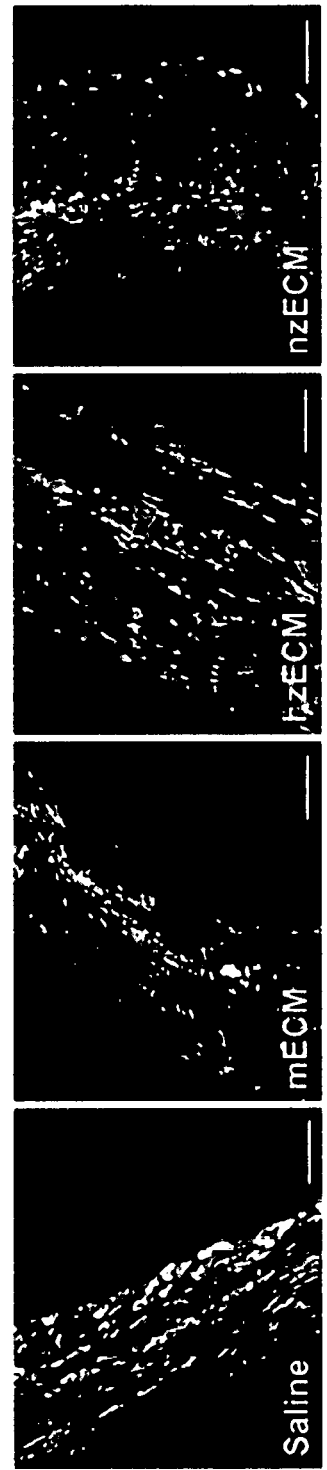

FIGS. 8A and 8B. Fibrosis and chronic inflammation. (FIG. 8A) Myocardial fibrosis at 6 weeks post-MI is revealed by Masson's trichrome stain in transverse sections of hearts injected with saline, mECM, nzECM, or hzECM (collagen in blue/purple in original, cardiac muscle in red in original; scale bars=1 mm). (FIG. 8B) Detection of chronic phagocytic cell infiltration by anti-mouse CD68 immunohistochemistry at 6 weeks post-MI in transverse sections of hearts injected with saline, mECM, nzECM, or hzECM (CD68 in green in original; scale bars=50 μm).

Figure 9A:
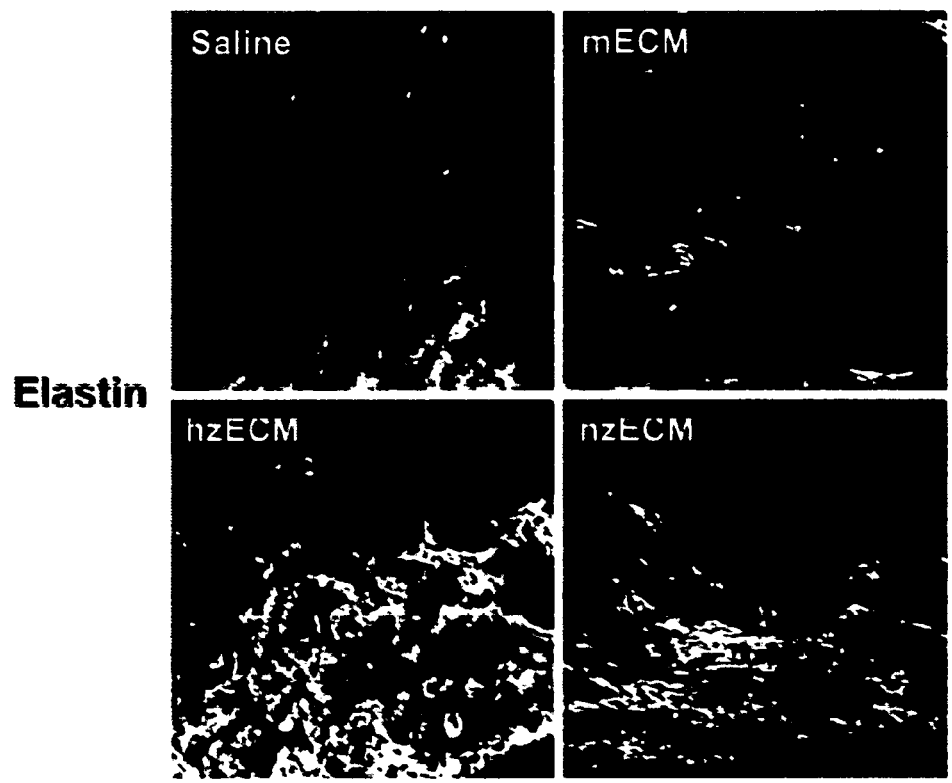
Figure 9B:
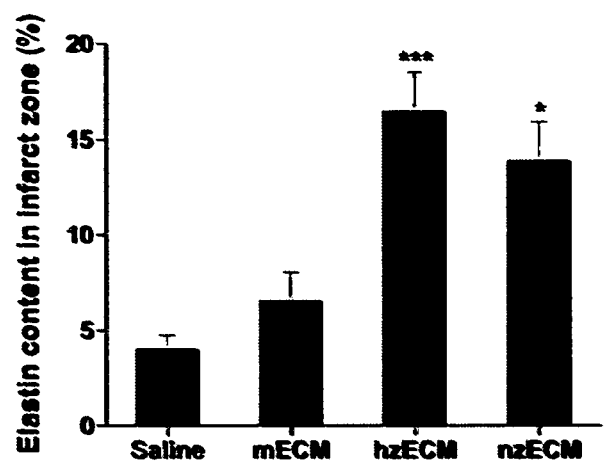

FIGS. 9A and 9B. Analysis of elastin within the infarct zone in zECM-treated hearts. (FIG. 9A) Representative images of anti-elastin immunostaining (elastin in green in original and DAPI in blue in original). (FIG. 9B) Quantification of the elastin content in the infarct zone. *p<0.05, ***p<0.001 compared to saline and mECM. All quantitative data represent means±SD.

FIGS. 10A-10H. Proliferation of cardiac precursor cell populations. Dual immunofluorescent detection and quantification of (FIGS. 10A-C) c-kit+/Ki67+ proliferating cardiac stem cells, (FIGS. 10D-F) PDGFRβ+/Ki67+ proliferating cardiac mesenchymal stromal cell, and (FIGS. 10G-H) Wt1+/Ki67+ proliferating epicardium-derived progenitor cells at 6 weeks post-MI at the mid-infarct level of mouse left ventricles. Arrows indicate doubly positive cells. All image analyses are performed within 20×10 micron areas in 5 images of each heart (N=4 per group). All quantitative data represent means±SD. *p<0.05, p<0.01, *p<0.001 compared to saline and mECM; #p<0.05, ##p<0.01 hzECM vs nzECM. Scale bars=50 μm.

FIGS. 11A-11F. Cardiomyocyte proliferation and ErbB2 expression. (FIGS. 11A-C) cTnT+/Ki67+ proliferating cardiomyocytes at 3 days post-MI at the mid-infarct level of mouse left ventricles. Arrows indicate doubly positive cells. (FIGS. 11D-F) Dual immunofluorescent detection and quantification of ErbB2+/cTnT+ cardiomyocytes suggest the involvement of NRG1 signaling in zECM-treated groups. All image analyses were performed using 20×10 micron areas in 5 images of each heart (N=4 per group). All quantitative data represent means ±SD. ***p<0.001 compared to saline and mECM; #p<0.05 hzECM vs nzECM. Scale bars=50 μm.

Figure 12A:
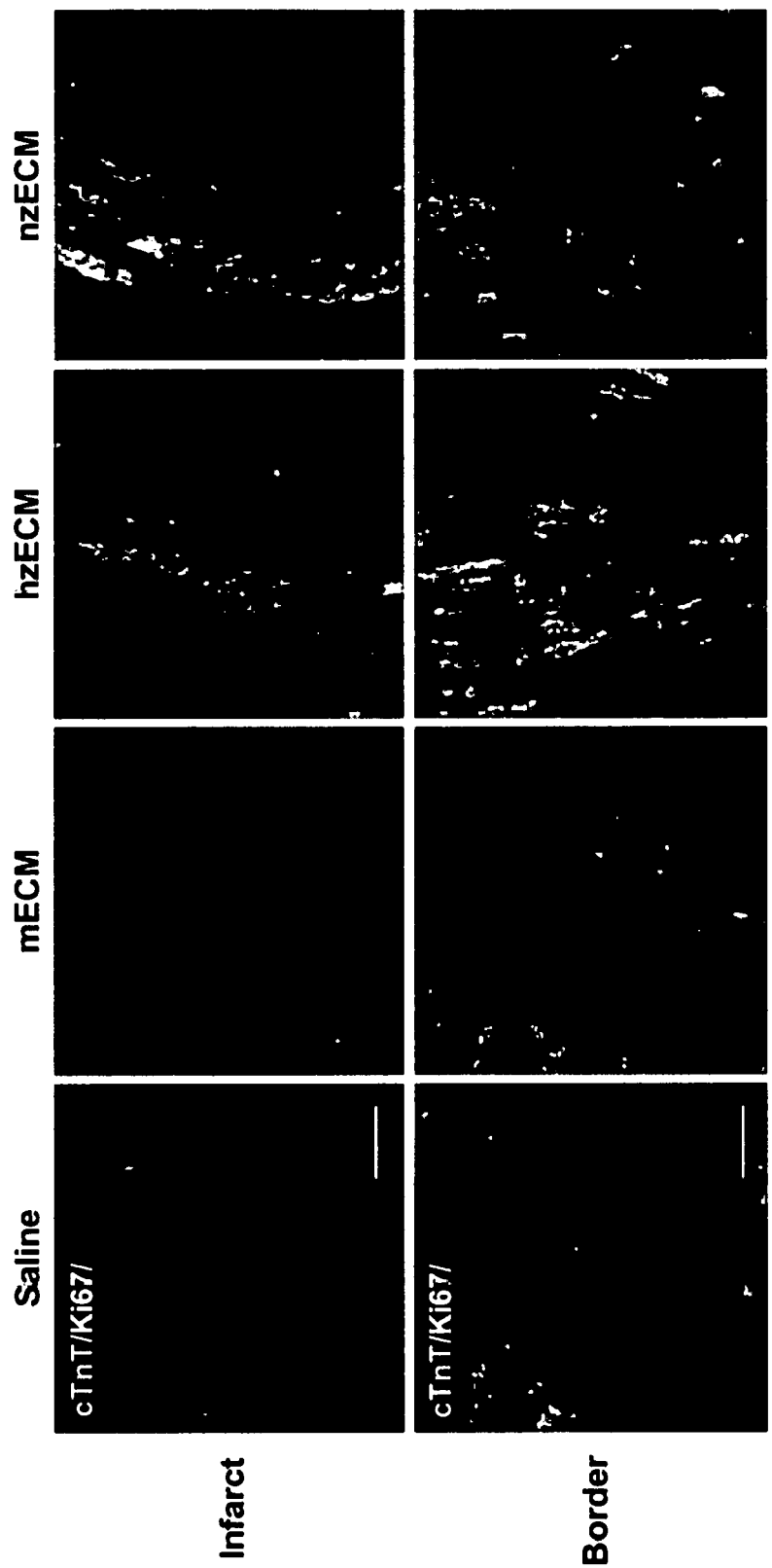
Figure 12B:
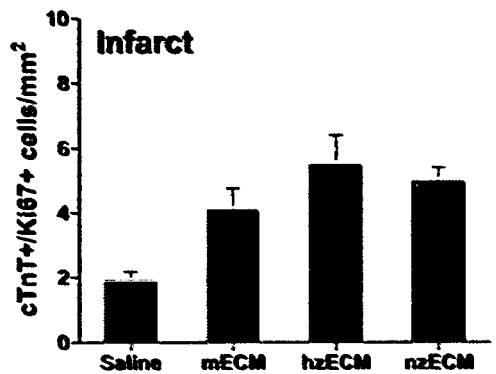
Figure 12C:
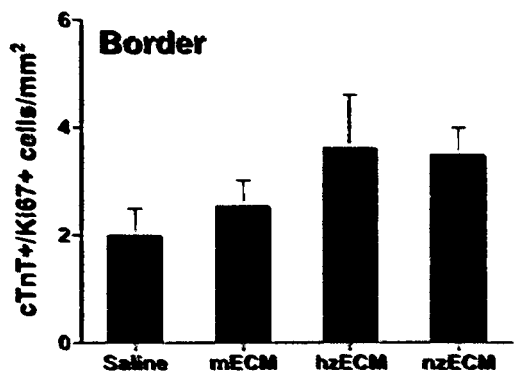

FIGS. 12A-12C. Cardiomyocyte proliferation at 6 weeks post-MI. (FIG. 12A) Dual immunofluorescent detection of cTnT+/Ki67+ cardiomyocytes at 3 days post-MI at the mid-infarct level of mouse left ventricles (scale bars=50 μm). Quantification of cTnT+/Ki67+ cardiomyocytes at the (FIG. 12B) infarct and (FIG. 12C) peri-infarct border zone. All p>0.05. All quantitative data represent means±SD.

FIGS. 13A-13D. (FIG. 13A) Immunoishochemical detection of NRG1 (arrow heads) in normal and healing (3 dpa) zebrafish hearts. (FIG. 13B) Positive immunofluorescent detection of NRG1 (green in original) at the ventricular apex of normal (nzH) and healing (hzH) zebrafish hearts but not in the adult mouse heart (mH). (FIG. 13C) Consistent with the in situ NRG1 staining, Western blotting showed that both normal (nzECM) and healing (hzECM) zebrafish heart ECM contain NRG1 protein. (FIG. 13D) Quantification data indicate hzECM and nzECM contain approximately 6.5 and 5 times more NRG1 than normal mouse heart ECM (mECM) respectively. Data represent means±SD. ***p<0.001 compared to mECM. Scale bar=50 μm.

Figure 14A:
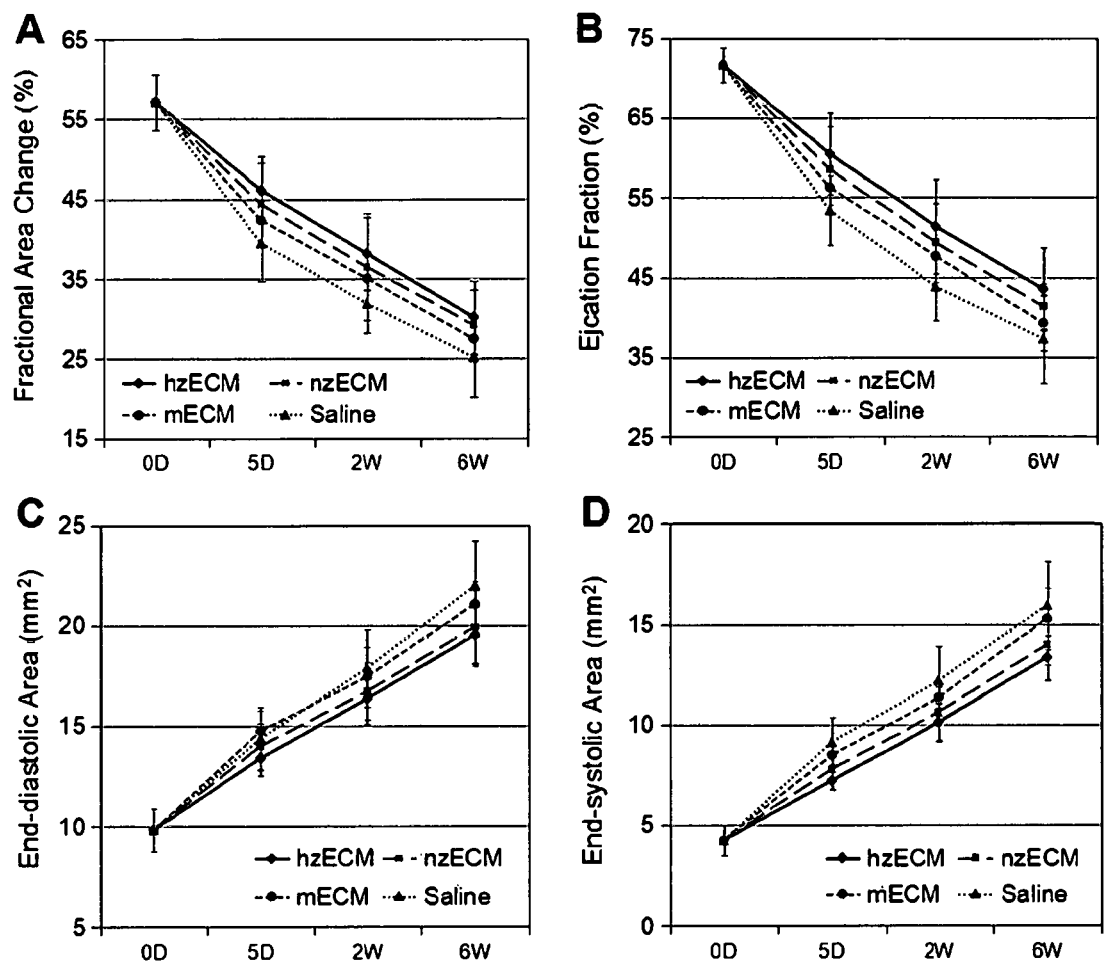

FIG. 14A-14D. Inhibition of ErbB2 activity with decellularized cardiac ECM treatment. Cardiac contractile function is indicated by FIG. 14A (A) fractional area change and FIG. 14A (B) ejection fraction; left ventricular dimension is indicated by FIG. 14A (C) end-diastolic area and FIG. 14A (D) end-systolic area. No significant difference is observed between all groups at all time points (N=7 per group; all p>0.05; data analyzed by two-way repeated ANOVA). Dual immunofluorescent detection and quantification of (FIGS. 14B and 14C) c-kit+/Ki67+ proliferating cardiac stem cells and (FIGS. 14D and 14E) ErbB2+/cTnT+ cardiomyocytes. No significant difference is observed between all groups (N=4 per group, all p>0.05). Scale bar=50 μm. All groups in this figure were incubated with the Erbb2 inhibitor AG825.

DETAILED DESCRIPTION

Other than in the operating examples, or where otherwise indicated, the use of numerical values in the various ranges specified in this application are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps. For definitions provided herein, those definitions refer to word forms, cognates and grammatical variants of those words or phrases.

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g. terminal groups, that are modified during polymerization are changed, removed, and/or relocated, and certain bonds may be added, removed, and/or modified. An incorporated monomer is referred to as a "residue" of that monomer. A polymer is said to comprise a specific type of linkage if that linkage is present in the polymer. Unless otherwise specified, molecular weight for polymer compositions refers to weight average molecular weight ($M_W$). A "moiety" is a portion of a molecule, compound or composition, and includes a residue or group of residues within a larger polymer.

By "biocompatible", it is meant that a device, scaffold composition, etc., and degradation products thereof, is essentially, practically (for its intended use) and/or substantially non-toxic, non-injurious or non-inhibiting or non-inhibitory to cells, tissues, organs, and/or organ systems that would come into contact with the device, scaffold, composition, etc.

As used herein, the term "comminute" and any other word forms or cognates thereof, such as, without limitation, "comminution" and "comminuting", refers to the process of reducing larger particles into smaller particles, including, without limitation, by grinding, blending, shredding, slicing, milling, cutting, crushing, and/or shredding. ECM can be comminuted while in any form, including, but not limited to, hydrated forms, frozen, air-dried, lyophilized, powdered, or sheet-form.

As used herein, the terms "extracellular matrix" and "ECM" refer to a natural scaffolding for cell growth that is prepared by decellularization (devitalization) of tissue found in multicellular organisms, such as mammals and humans. ECM can be further processed by, for instance sterilization, disinfection, dialysis and/or cross-linking. ECM is a complex mixture of structural and non-structural biomolecules, including, but not limited to, collagens, elastins, laminins, glycosaminoglycans, proteoglycans, antimicrobials, chemoattractants, cytokines, and/or growth factors. In mammals, ECM often comprises about 90% collagen, in its various forms. However, ECM does not include as a class purified preparations of single compositions found in tissue, such as purified collagen preparations. The composition and structure of ECM varies depending on the source of the tissue. For example, small intestine submucosa (SIS), urinary bladder matrix (UBM) and liver stroma ECM each differ in their overall structure and composition due to the unique cellular niche needed for each tissue.

As used herein, the term "derive", "derived," or "derives", refers to a component or components obtained from any stated source by any useful method. For example and without limitation, an ECM-derived gel refers to a gel comprised of components of ECM obtained from any tissue by any number of methods known in the art for isolating ECM. In another example, regenerating tissue-derived rECM refers to ECM comprised of components of regenerating, developing or growing tissue obtained from any animal, by any useful method.

Methods of preparing regenerative extracellular matrix (rECM) compositions comprising extracellular matrix obtained from growing, developing and/or regenerating tissues are provided herein. Related compositions, devices and methods of use also are provided.

Regenerative ECM (rECM) material described herein is prepared from tissue undergoing growth, development, or regeneration. In one aspect, the tissue is regenerative tissue obtained from an organism that has inherent regenerative capacity, and in certain aspects from tissue of that organism that has inherent regenerative capacity and that is optionally undergoing regeneration. As used herein, "regeneration" refers to the ability of a mature organism to regrow, repair or replace tissue that is lost, for example under circumstances where another organism, such as a human, cannot regenerate the same tissue, with examples of such regenerative tissue being described herein, including zebrafish heart tissue as shown in the Examples below. In one aspect, the rECM is prepared from growing tissue, such as fetal or neonatal tissue, obtained from an animal, such as an invertebrate, a vertebrate or a mammal. In another aspect, the rECM is prepared from regenerating tissue, that is tissue that is obtained from an animal capable of regeneration and the tissue is actively regenerating. A number of organisms undergo spontaneous regeneration, e.g., when injured or when growing tissue or organs that generate one or more times during the natural life progression of the animal. In many cases, the regeneration is limited to specific organs or limbs, as in the case of lizard tails, deer antlers, rabbit ears, bat wings, and spiny mouse (*Acomys*) ears and skin. A number of invertebrates undergo autotomy as an avoidance or protective behavior, including land slugs (*Prophysaon*), sea snails (e.g., *Oxynoe panamensis*), octopus, crickets, spiders, crabs and lobsters. Autotomous vertebrates include lizards and amphibians, such as salamanders, newts and other urodeles, as well as the axolotl (*Ambystoma mexicanum*), which can regenerate most of its body parts. As shown herein, the zebrafish can regenerate at least cardiac tissue. Other animals capable of regeneration, and especially bidirectional regeneration (the ability to regenerates a complete animal from a part of the animal, as opposed to unidirectional regeneration which is the ability of an animal to regenerate one or more specific parts, such as the lizard's tail, the zebrafish's heart or the spiny mouse's skin), including hydras, certain echinoderms such as sea stars, sea urchins and sea cucumbers, and anemones. Planaria show a dramatic ability to regenerate bidirectionally, in that even small parts of a planarian can regenerate a full organism.

In one aspect, the tissue is obtained from a genetically-modified organism that is modified by man by any useful method, such as by: mutagenesis (e.g., irradiation or chemically-induced mutation); chimerae; gene transfer, such as transgenic technologies; and genome editing (e.g. CRISPR/Cas9). This is in contrast to normal, or wild type tissue or organisms that are found in nature, or are obtained by traditional breeding, selective breeding, and cross-breeding techniques. In another aspect, the tissue is genetically-modified ex vivo or in vitro. The modification can be modification of any DNA sequence in the tissue or organism. Tissue may be cultured ex vivo or in vitro to produce suitable rECM structures.

In one aspect, regenerating tissue is processed to prepare rECM. In one aspect, regenerating tissue is prepared by damaging tissue that is capable of regeneration, such as the zebrafish cardiac tissue as shown below, planarian tissue, echinoderm tissue, amphibian, or lizard tissue by causing trauma to the tissue capable of regeneration. Tissue may be damaged by any means, such as by physical trauma, chemical damage, heating or cooling (e.g. freezing) damage, radiation damage, and/or electrical damage. The tissue is regrown at least long enough for the tissue to begin regrowth, but not so long as to complete regrowth.

To produce rECM, the tissue is devitalized. The rECM is preferably minimally processed to produce intact rECM. In one aspect, no detergents, dialysis and/or crosslinking are used to prepare the rECM. As indicated above and in the examples below, the regenerating tissue is processed, in one aspect by freezing, thawing, and digestion of nucleic acids, for example by DNAse and RNAse treatment. The rECM can then be stored prior to use as-is, or can be lyophilized, optionally comminuted, optionally sterilized, and stored prior to use. A gel composition can be prepared as described above by digestion of the product with an acid protease, followed by neutralization and raising the temperature of the mixture to physiological temperature, e.g., 37° C. or from 30° C. to 40° C.

In one aspect, planaria or hydra are used as the source of regenerating tissue because they are common, easy to grow in culture, and large quantities of regenerating tissue can be produced by damaging the organisms, for example by blending, chopping, radiating, or by chemical treatment of the organisms, allowing the organisms to recover and begin regeneration and, prior to complete regeneration of the organisms, harvesting the organisms for processing to rECM as described herein. Likewise, zebrafish hearts can be damaged in vivo, e.g., as described herein by surgical removal of all or part of the ventricular apex, and subsequently harvested for processing to rECM.

In another aspect, the regenerating tissue is prepared in vitro, in an appropriate cell or organ culture environment to permit growth of regenerating tissue.

According to one aspect, rECM is prepared from regenerating and growing or developing tissue, such as fetal or neonatal (within one week of birth) tissue. By "growing or developing tissue," it is meant tissue that is rapidly growing prior to adult maturity, for example in neonates or fetuses, and does not refer to tissues, such as intestinal mucosa, that normally propagate in adult mammals. Thus, in one aspect, adult immune tissue and intestinal tissue are excluded from the category of "growing tissue". If needed, regenerating, growing or developing tissue is comminuted prior to processing, however for certain tissues that have minimal size or thickness, such as zebrafish heart tissue, comminution is not necessary prior to devitalizing. The tissue is optionally washed prior to further processing, e.g., in an isotonic solution and/or in an antibiotic-containing solution (e.g. a P/S/A/G solution as described below). By "washed" it is meant an aqueous wash solution is added to the material to be washed, optionally mixed with the material to be washed, and removed, e.g., by centrifugation and decanting the wash solution. Red blood cells are optionally lysed, e.g., using suitable erythrolysis buffer, which are broadly-known and are commercially available. The tissue is frozen and thawed to kill live cells, and is then treated with nucleases, e.g. DNase and RNase, to remove nucleic acids. Washing steps, e.g. with an isotonic solution, such as PBS or isotonic saline and/or with antibiotics, are performed as needed to remove cellular debris and digested nucleic acids. The composition can then be utilized at that stage. The composition is then frozen or dried, e.g. lyophilized, stored, sterilized (e.g., when in a dried state). In use, dried rECM is re-hydrated in a suitable aqueous solution, such as water, PBS, or normal saline, optionally with one or more antibiotics, and is optionally centrifuged to remove large particles and/or frozen prior to use. The composition can then be used immediately, e.g., injected into a patient at a treatment site, or digested with an acid protease as outlined herein, to make a gel.

According to one aspect, a method of preparing an extracellular matrix-derived gel is provided. In the method, extracellular matrix (ECM) is solubilized by digestion with an acid protease such as trypsin or pepsin in an acidic solution to produce a digest solution. The digest solution is then brought to a pH between 7.2 and 7.8 to produce a neutralized digest solution, for example, by mixing the solution with an isotonic buffer or a base, such as, without limitation NaOH. The solution gels at a temperature greater than 25° C. The compositions are therefore "reverse gelling," meaning that the viscosity of the matrix increases when warmed above the lower critical solution temperature (LCST) of the composition, for example to physiological temperatures approaching about 37° C. According to one non-limiting aspect, the ECM-derived composition is an injectable solution at temperatures lower than 37° C., but a gel at a physiological temperature of 37° C. According to certain embodiments, the gel is bioactive because the entire, intact ECM is solubilized, and is not dialyzed, cross-linked and/or otherwise treated to remove or otherwise inactivate ECM structural or functional components. ECM-derived gels can be prepared from a variety of tissues from a variety of sources, including urinary bladder, spleen, liver, heart, pancreas, ovary, small intestine, large intestine, colon, central nervous system (CNS), adipose tissue and bone. Non-limiting examples of reverse-gelling ECM-derived compositions are described in U.S. Pat. No. 8,361,503, and United States Patent Publication Nos. 2010-0226895, and International Patent Publication Nos. WO 2011/087743 WO 2013/009595.

In further detail, in order to prepare solubilized rECM or ECM, tissue, for example regenerative tissue, e.g. tissue undergoing regeneration or tissue that is developing or otherwise growing, for example as described herein, is digested with an acid protease in an acidic solution to form a digest solution. The tissue, e.g., regenerative tissue, is comminuted if needed and as needed prior to digestion with an acid protease in order to facilitate complete solubilization. As used herein, the term "acid protease" refers to an enzyme that cleaves peptide bonds, wherein the enzyme has increased activity of cleaving peptide bonds in an acidic pH. For example and without limitation, the acid protease is pepsin.

The digest solution of rECM or ECM typically is kept at a constant stir for a certain amount of time at room temperature. The digest solution can be used immediately or can be stored at −20° C. or frozen at, for example and without limitation, −20° C. or −80° C., and optionally dried and sterilized. Next, the pH of the digest solution is raised to a pH between 7.2 and 7.8 to produce a neutralized digest solution, which is typically done at a temperature below the LCST or gelation temperature of the material to prevent gelation from beginning immediately. The pH can be raised by adding one or more of a base or an isotonic buffered solution, for example and without limitation, NaOH or PBS at pH 7.4. The method typically does not include a dialysis step prior to gelation, yielding a more-complete ECM-like matrix that typically gels at 37° C. more slowly than comparable collagen or dialyzed ECM preparations. The gel is therefore more amenable to injection into a patient, and also retains more of the qualities of native ECM due to retention of many native soluble factors, such as, without limitation, cytokines.

As used herein, the term "isotonic buffered solution" refers to an isotonic solution that is buffered to a pH between 7.2 and 7.8 and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH, or NaOH in PBS.

The neutralized digest solution can be gelled at that point by incubation at a suitably warm temperature, for example and without limitation, at about 37° C. Optionally, the neutralized digest solution is frozen and stored at, for example and without limitation, −20° C. or −80° C. As used herein, the term "neutralized digest solution" or "neutralized digest" refers to a digest or digest solution wherein the pH is increased, and can be in the form of a solution or dried/lyophilized composition. For example and without limitation, a neutralized digest has a pH between 7.2 and 7.8.

The compositions described herein find use as, without limitation, an injectable graft (e.g., xenogeneic, allogeneic or autologous) for tissues, for example, bone or soft tissues, in need of repair or augmentation most typically to correct trauma or disease-induced tissue defects. A defect can be acquired or congenital. The compositions also may be used as a filler for implant constructs comprising, for example, a molded construct formed into a desired shape for use in cosmetic or trauma-treating surgical procedures. In use, rECM is prepared from regenerating, growing or developing tissue that is the same tissue (or a precursor thereof) as the tissue being repaired. For example, as indicated below, regenerating heart tissue is used to repair ischemic myocardium (an infarct). Regenerating tissue also may be used to treat, a ischemia/reperfusion injury, a congenital myocardial or outflow tract defect, or a condition involving loss of or reduced amount of myocardial tissue, and the rECM is injected into or adjacent to the infarction, injury site, or defect location.

In one aspect, the rECM-containing compositions described herein are implanted into a patient, e.g., a human patient or animal patient, by any of a number of methods. In one non-limiting aspect, the compositions are injected as a reconstituted powder prepared from dried rECM, into a treatment site in the patient. In another aspect, the compositions are injected as a neutralized digest solution, that is, as a liquid, into a treatment site in the patient.

"ECM" and "rECM" retain the activity of certain structural and non-structural biomolecules, including, but not limited to, collagens, elastins, laminins, glycosaminoglycans, proteoglycans, antimicrobials, chemoattractants, cytokines, and/or growth factors, such as, without limitation comminuted ECM as described herein. The activity of the biomolecules within the ECM can be removed chemically or mechanically, for example, by cross-linking and/or by dialyzing the ECM. Therefore, according to one aspect of the invention, ECM or rECM are ECM that have not been processed by chemical or enzymatic processes other than with one or more added nucleases (DNase and/or RNase) and by chemical or enzymatic processes that natively occur by action of chemicals or enzymes within the native tissue during the course of preparation. In one aspect of the invention, ECM or rECM is not cross-linked and/or dialyzed, meaning that the ECM has not been subjected to a dialysis and/or a cross-linking process, or such conditions, that is, ECM or rECM that is not substantially cross-linked and/or dialyzed in anything but a trivial manner which does not substantially affect the gelation and functional characteristics of the ECM in its uses described herein. One example of ECM or rECM is tissue that has been comminuted, frozen, thawed, and treated with DNAse and RNAse, and is optionally dried and sterilized, but is not dialyzed or cross-linked prior to use, or where an ECM gel is prepared, it is not dialyzed or cross-linked prior to gelation.

In general, the method of preparing an ECM-derived gel requires the isolation of ECM from an animal of interest and from a tissue or organ of interest. For example and without limitation, tissue can be derived from aggregates of cells, an organ, portions of an organ, or combinations of organs. In certain aspects, the ECM is isolated from a vertebrate animal, for example and without limitation, human, monkey, pig, cattle, and sheep. In certain aspects, the ECM is isolated from any tissue of an animal, for example and without limitation, urinary bladder, liver, CNS, adipose tissue, small intestine, large intestine, colon, esophagus, pancreas, dermis, and heart. In one aspect, ECM is derived from a urinary bladder. The ECM may or may not include the basement membrane portion of the ECM. In certain aspects, the ECM includes at least a portion of the basement membrane. The ECM may or may not retain some of the cellular elements that comprised the original tissue such as capillary endothelial cells or fibrocytes.

The compositions described herein can be used in a number of ways or forms. For example and without limitation, according to a first aspect, as an ECM gel as described above, for instance the neutralized digest is placed in a suitable mold to model an organ or a portion thereof. As a non-limiting example, the composition is molded into a portion of a heart to facilitate re-growth of heart tissue. In another non-limiting example, the composition is molded in the shape of a nose, an ear cartilage, liver, pancreas, or virtually any anatomical structure or a portion thereof, for replacement of damaged, defective or excised tissue. In yet another non-limiting example, the composition is molded into the shape of a wound to facilitate non-scarring healing of that tissue. To prepare the molded gel, the neutralized digest is placed in a biocompatible and preferably sterile mold, such as a plastic mold, and is incubated at a temperature and for a time suitable for gelation of the composition, for example and without limitation at about 37° C. In one embodiment, the composition and mold is placed in an incubator at 37° C. to gel. Because $CO_2$ has been found to slow gelation, in one non-limiting embodiment, $CO_2$ is not injected into the incubator, though in yet another embodiment, $CO_2$ and/or temperature may be used to control the gelation process. The molded structure can be seeded with appropriate cells and/or contacted with an active agent to promote adsorption, absorption or otherwise adding/mixing, contacting, treating, binding, etc. the cells and/or active agent(s) with the structure.

Any useful cytokine, chemoattractant or cells can be mixed into the composition prior to gelation or diffused, absorbed and/or adsorbed by the gel after it is gelled. For example and without limitation, useful components include growth factors, interferons, interleukins, chemokines, monokines, hormones, angiogenic factors, drugs and antibiotics. Cells can be mixed into the neutralized, solubilized gel or can be placed atop the molded composition once it is gelled. In either case, when the gel is seeded with cells, the cells can be grown and/or adapted to the niche created by the molded ECM gel by incubation in a suitable medium in a bioreactor or incubator for a suitable time period to optimally/favorably prepare the composition for implantation in a patient. The molded composition can be seeded with cells to facilitate in-growth, differentiation and/or adaptation of the cells. For example and without limitation, the cells can be autologous or allogeneic with respect to the patient to receive the composition/device comprising the gel. The cells can be stem cells or other progenitor cells, or differentiated cells. In one example, a layer of dermis obtained from the patient is seeded on a mold, for use in repairing damaged skin and/or underlying tissue.

As used herein, the term "mold" refers to a cavity or surface used to form the gel into a three-dimensional shape. For example and without limitation, the mold can be a well plate, cell culture dish or a tube or can be shaped into any useful shape. In a certain embodiment, the mold can be shaped into a certain organ or part of an organ. The gel can be delivered to the mold in a variety of methods, including, but not limited to, injection, deposition.

As used herein, the terms "drug" and "drugs" refer to any compositions having a preventative or therapeutic effect, including and without limitation, antibiotics, peptides, hormones, organic molecules, vitamins, supplements, factors, proteins and chemoattractants.

The composition may be pre-seeded with cells, and then injected using a needle such as a larger bore needle, e.g. a 16 gauge needle, to prevent shearing of cells. As used herein, the term "seed," "seeding," or "seeded" refers to the addition, incorporation, propagation of, or spreading of a defined volume of a cell suspension or a defined cell number into a specific composition. In another aspect, the composition is gelled within a mold, and the gelled, molded product is then implanted into a patient at a desired site. The gelled, molded product may be pre-seeded (e.g., laid onto the molded gel or mixed in during gelation) with cells, such as cells of the patient. In another aspect, the composition is provided as a sheet, for example coated on absorbed to, admixed with or otherwise combined an ECM and/or polymeric material, such as a bioerodible material, that provides adequate strength to permit suturing or gluing into place and/or to retain form.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

One favorable aspect of the use of pre-molded tissue is that a layered composition can be produced. For example, a core portion of the composition to be implanted can be prepared with a first rECM-containing gel, and a surrounding layer can be with a second ECM-containing gel, obtained from a second source tissue different from the first, or the same source as the first, but containing different constituents, such as active agents such as cytokines and/or cells.

In another aspect of the pre-molded composition, the ECM gel is contained within a laminar sheath of non-comminuted and non-digested ECM tissue, such as SIS or UBM, and/or a non-woven, optionally biodegradable composition, to add physical strength to the gel. In this embodiment, sheets of ECM tissue and/or a biodegradable polymer composition, such as a nonwoven material, prepared in any manner known in the art, can be placed into the mold prior to filling the mold with the solubilized ECM tissue for producing the gel. The sheets of ECM tissue and/or biodegradable polymer may be used as the mold, so long as they are formed and sewn or cross-linked into a desired shape. In this manner, a solid composition can be produced that has greater physical strength than is the case of a gel, alone.

In another non-limiting embodiment, the composition is injected as a neutralized digest solution into a patient. The composition is injected at a locus in the patient where the matrix is needed for cell growth. For example and without limitation, where a patient has had tissue removed due to a tissue defect, trauma, debridement and/or removal of damaged, diseased or cancerous tissue, the composition can be injected at the site of tissue removal to facilitate in-growth of tissue. The viscosity of the pre-gel can be controlled by varying the amounts of water (e.g., by varying the amounts of water, acid, base, buffer (such as PBS) or other diluents) used to prepare the pre-gel. In applications in which a small gauge needle is used, such as in endoscopy, a less viscous pre-gel would be needed, which typically results in a less viscous gel once the pre-gel is gelled. In applications in which a larger gauge needle is available, a more viscous gel, with higher strength when gelled, can be used. Also, use of a larger gauge needle, e.g., a 16 gauge needle, irrespective of the viscosity of the pre-gel, favors mixing of live cells with the pre-gel immediately prior to implantation with less risk of shearing the cells.

In one aspect involving a gel containing the rECM, a neutralized digest solution is prepared by raising the pH of the acidic digest solution and the composition is directly injected into a patient prior to significant gelation proceeds. In one embodiment, the composition is in a frozen state and is thawed and warmed prior to injection. In another embodiment, the acidic digest solution is warmed to physiological temperature and is mixed during injection in a static mixer with suitable quantities of a base and/or buffer, such as PBS. Suitable static mixers include, without limitation, helical or square static mixers, commercially available from Cammda Corporation of Cobourg, Ontario, Canada or a Mini-Dual Syringe with Micro Static Mixer commercially available from Plas-Pak Industries, Inc. of Norwich, Conn.

In one aspect, the rECM composition is combined with other ECM compositions and/or synthetic polymers, such as biodegradable elastomeric (co)polymers. The rECM can is combined in any manner. For example the rECM can be mixed with the ECM compositions and/or synthetic polymers, coated on the ECM compositions and/or synthetic polymers; formed or layered with the ECM compositions and/or synthetic polymers, electrodeposited (e.g., electrospun and/or electrosprayed, either as separate streams or a single stream) with the ECM compositions and/or synthetic polymers or otherwise combined with the ECM compositions and/or synthetic polymers. In one example, the rECM is prepared, for example as described above, by freezing, thawing, incubation with DNAse and RNAse, dried and comminuted or mixed with intact ECM. The mixture of rECM and ECM is then digested with an acid protease and is neutralized and gelled as described above to form a hybrid reverse-gelling ECM composition. In another embodiment, ECM compositions and/or synthetic polymers are electrospun and an rECM solution, such as a rECM neutralized digest solution alone or mixed with an ECM neutralized digest solution, as described above, is electrosprayed onto or with the ECM compositions and/or synthetic polymers.

A variety of ECM materials or compositions can be used in combination with the rECM described herein. Broadly, ECM is a decellularized, devitalized ECM-derived scaffold material. An "ECM-derived material," is a material prepared from an extracellular matrix-containing tissue. Examples of extracellular matrix scaffold material are provided in U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666. In certain aspects, the ECM is isolated from a vertebrate animal, for example and without limitation, from a mammal, including, but not limited to, human, monkey, pig, cow and sheep. The ECM can be derived from any organ or tissue, including without limitation, urinary bladder, intestine, liver, esophagus and dermis, or regenerating, growing or developing tissue as described herein in the context of preparing rECM. In one embodiment, the ECM is cardiac ECM. As indicated above, regenerative, growing or developing tissue can be used to prepare rECM, a form of ECM. In one aspect, the ECM is not dialyzed or cross-linked prior to use, or where ECM gel is prepared, the material is not dialyzed or cross-linked prior to gelation.

In one aspect, ECM material is decellularized, sterilized and/or dried by any useful method. Methods described herein for preparation of rECM may be used to prepare ECM material. ECM-derived material can then be used in any form in the methods and compositions described herein. For instance, the compounds described herein can be applied to sheets of ECM or as comminuted and/or solubilized ECM to prepare a scaffold suitable to apply to the heart of a patient.

ECM may be sterilized by any of a number of standard methods. For example, the material can be sterilized by propylene oxide or ethylene oxide treatment, gamma irradiation treatment (0.05 to 4 mRad), gas plasma sterilization, peracetic acid sterilization, or electron beam treatment. ECM may be disinfected by immersion in 0.1% (v/v) peracetic acid (a), 4% (v/v) ethanol, and 96% (v/v) sterile water for 2 h. The ECM material is then washed, e.g., twice for 15 min with PBS (pH=7.4) and twice for 15 min with deionized water.

Commercially-available ECM preparations can also be used in certain aspects of the methods, devices and compositions described herein in combination with the rECM materials described herein. In one aspect, the ECM is derived from small intestinal submucosa or SIS. Commercially available preparations include, but are not limited to, Surgisis™, Surgisis-ES™, Stratasis™, and Stratasis-ES™ (Cook Urological Inc.; Indianapolis, Ind.) and GraftPatch™ (Organogenesis Inc.; Canton Mass.). In another aspect, the ECM is derived from dermis. Commercially available preparations include, but are not limited to Pelvicol™ (crosslinked porcine dermal collagen, sold as Permacol™ in Europe; Bard Medical Division, Covington, Ga.), Repliform™ (Microvasive; Boston, Mass.) and Alloderm™ (LifeCell; Branchburg, N.J.). In another aspect, the ECM is derived from urinary bladder. Commercially available preparations include, but are not limited to UBM (Acell Corporation; Jessup, Md.).

A number of biocompatible, biodegradable elastomeric (co)polymers are known and have been established as useful in preparing cell growth matrices and therefore are useful in combination with the rECM compositions described herein, including biodegradable poly(ester urethane) urea (PEUU), poly(ether ester urethane)urea (PEEUU), poly(ester carbonate)urethane urea (PECUU) and poly(carbonate)urethane urea (PCUU). In general, useful (co)polymers comprise monomers derived from alpha-hydroxy acids including polylactide, poly(lactide-co-glycolide), poly(L-lactide-co-caprolactone), polyglycolic acid, poly(dl-lactide-co-glycolide), poly(l-lactide-co-dl-lactide); monomers derived from esters including polyhydroxybutyrate, polyhydroxyvalerate, polydioxanone and polyglactin; monomers derived from lactones including polycaprolactone; monomers derived from carbonates including polycarbonate, polyglyconate, poly(glycolide-co-trimethylene carbonate), poly(glycolide-co-trimethylene carbonate-co-dioxanone); monomers joined through urethane linkages, including polyurethane, poly(ester urethane) urea elastomer.

In one aspect, the synthetic polymer that is combined with the rECM composition comprises a biodegradable poly(ester urethane) urea elastomer (PEUU). PEUU can be manufactured by reacting a diol with a diisocyanate to form a prepolymer and then reacting the prepolymer with a diamine. A non-limiting example of such a PEUU is an elastomeric polymer made from polycaprolactone diol (Mw 2000) and 1,4-diisocyanatobutane, using a diamine chain extender such as putrescine. One non-limiting example or a method for preparing a PEUU polymer is a two-step polymerization process whereby polycaprolactone diol (Mw 2000), 1,4-diisocyanatobutane, and diamine are combined in a 2:1:1 molar ratio. In the first step to form the prepolymer, a 15 wt % solution of 1,4-diisocyanatobutane in DMSO (dimethyl sulfoxide) is stirred continuously with a 25 wt % solution of polycaprolactone diol in DMSO. Then, stannous octoate is added and the mixture is allowed to react at 75° C. for 3 hours. In the second step, the prepolymer is reacted with a diamine to extend the chain and to form the polymer. In one embodiment, the diamine is putrescine, which is added drop-wise while stirring and allowed to react at room temperature for 18 hours. In one embodiment, the diamine is lysine ethyl ester, which is dissolved in DMSO with triethylamine, added to the prepolymer solution, and allowed to react at 75° C. for 18 hours. After the two step polymerization process, the polymer solution is precipitated in distilled water. Then, the wet polymer is immersed in isopropanol for three days to remove any unreacted monomers. Finally, the polymer is dried under vacuum at 50° C. for 24 hours.

In another aspect, the synthetic polymer that is combined with the rECM composition comprises poly(ether ester urethane) urea elastomer (PEEUU). For example and without limitation, the PEEUU may be made by reacting polycaprolactone-b-polyethylene glycol-b-polycaprolactone triblock copolymers with 1,4-diisocyanatobutane and putrescine. In one non-limiting embodiment, PEEUU is obtained by a two-step reaction using a 2:1:1 reactant stoichiometry of 1,4-diisocyanatobutane:triblock copolymer:putrescine. According to one non-limiting embodiment, the triblock polymer can be prepared by reacting poly(ethylene glycol) and ε-caprolactone with stannous octoate at 120° C. for 24 hours under a nitrogen environment. The triblock copolymer is then washed with ethyl ether and hexane, then dried in a vacuum oven at 50° C. In the first step to form the prepolymer, a 15 wt % solution of 1,4-diisocyanatobutane in DMSO is stirred continuously with a 25 wt % solution of triblock copolymer in DMSO. Then, stannous octoate is added and the mixture is allowed to react at 75° C. for 3 hours. In the second step, putrescine is added drop-wise under stirring to the prepolymer solution and allowed to react at room temperature for 18 hours. The PEEUU polymer solution is then precipitated with distilled water. The wet polymer is immersed in isopropanol for 3 days to remove unreacted monomer and dried under vacuum at 50° C. for 24 hours.

In another aspect, the synthetic polymer that is combined with the rECM composition comprises a poly(ester carbonate)urethane urea (PECUU) or a poly(carbonate)urethane urea (PCUU), which are described, for example, in Hong et al. (Tailoring the degradation kinetics of poly(ester carbonate urethane)urea thermoplastic elastomers for tissue engineering scaffolds Biomaterials, Biomaterials 31 (2010) 4249-4258). Poly(ester carbonate urethane)urea (PECUU) is synthesized, for example using a blended soft segment of polycaprolactone (PCL) and poly(1,6-hexamethylene carbonate) (PHC) and a hard segment of 1,4-diisocyanatobutane (BDI) with chain extension by putrescine. Different molar ratios of PCL and PHC can be used to achieve different physical characteristics. Putrescine is used as a chain extender by a two-step solvent synthesis method. In one example, the (PCL+PHC):BDI:putrescine molar ratio is defined as 1:2:1. Variable molar ratios of PCL and PHC (e.g., PCL/PHC ratios of 100/0 (yielding a PEUU), 75/25, 50/50, 25/75 and 0/100 (yielding a PCUU)) are completely dissolved in DMSO in a 3-neck flask with argon protection and then BDI is added to the solution, following 4 drops of $Sn(Oct)_2$. The flask is placed in an oil bath at 70° C. After 3 h, the prepolymer solution is cooled at room temperature and then a putrescine/DMSO solution is added dropwise into the agitated solution. The final polymer solution concentration is controlled to be approximately 4% (w/v). Then the flask is than placed in an oil bath and kept at 70° C. overnight. The polymer is precipitated in an excess volume of cool deionized water and then dried in a vacuum at 60° C. for 3 days. The polyurethane ureas synthesized from the different PCL/PHC molar ratios defined above are referred to as PEUU, PECUU 75/25, PECUU 50/50, PECUU 25/75 and PCUU, respectively. In practice, the yields of all final products using this method is approximately 95%.

Diamines and diols also are useful building blocks for preparing (co)polymer compositions that, in certain aspects, are combined with the rECM composition. Diamines as described above have the structure $H_2N-R-NH_2$ where "R" is an aliphatic or aromatic hydrocarbon or a hydrocarbon comprising aromatic and aliphatic regions. The hydrocarbon may be linear or branched. Examples of useful diamines are putrescine (R=butylene) and cadaverine (R=pentylene). Useful diols include polycaprolactone (e.g., Mw 1000-5000), multi-block copolymers, such as polycaprolactone-PEG copolymers, including polycaprolactone-b-polyethylene glycol-b-polycaprolactone triblock copolymers of varying sizes. Other building blocks for useful diols include, without limitation glycolides (e.g. polyglycolic acid (PGA)), lactides, dioxanones, and trimethylene carbonates. Diisocyanates have the general structure OCN—R—NCO, where "R" is an aliphatic or aromatic hydrocarbon or a hydrocarbon comprising aromatic and aliphatic regions. The hydrocarbon may be linear or branched.

In a further aspect, a commercial kit is provided comprising a composition described herein. A kit comprises suitable packaging material and the composition. In one non-limiting embodiment, the kit comprises in a vessel, rECM in any form described herein, for example as a solid, a powder, liquid, frozen composition, a digest solution for preparation of a gel, etc. The vessel may be the packaging material, or is contained within packaging material. If the packaged composition is a digest solution is neutralized, it may be frozen, cooled; e.g., kept at near-freezing temperatures, such as, without limitation, below about 4° C. or kept at room temperature, e.g., 20-25° C. In another aspect, the kit comprises a first vessel containing an acidic solution comprising a pre-neutralization rECM digest as described herein, and a second vessel comprising a neutralizing solution comprising a base and/or buffer(s) to bring the acidic solution of the first vessel to physiological ionic strength and pH, to form a neutralized digest prior to use. In a further embodiment, the first vessel contains an optionally terminally sterilized, lyophilized, pre-neutralization digest that can be hydrated using water or a suitable aqueous solution that optionally neutralizes the acid. In this embodiment, a second vessel is optionally provided comprising a neutralization solution as described above that is capable of both hydrating the lyophilized product and neutralizing it, or optionally a third vessel comprising water or any other suitable solution useful in hydrating the lyophilized product prior to neutralization with the neutralization solution. This kit also optionally comprises a syringe, a mixing needle and/or a cold-pack as is needed. The vessel may be a vial, medical syringe, tube or any other container suitable for storage and transfer in commercial distribution routes of the kit.

In yet another aspect of the kit, a gel composition is molded and pre-gelled prior to packaging and distribution. In one embodiment, the molded gel is packaged in a blister-pack comprising a plastic container and a paper, plastic and/or foil sealing portion, as are well-known in the art. The mold and packaging typically is sterilized prior to or after packaging, for example and without limitation, by gamma or electron beam irradiation or supercritical $CO_2$. The molded composition may be packaged in any suitable physiological solution, such as PBS or saline, optionally with one or more antibiotics. If the molded gel contains live cells, the mold can be transported in a suitable cell-culture medium in a sealed jar or other vessel. Of course, the cell-containing molded gel would have to be shipped in an expedited manner to preserve the cells.

As used herein, the term "hybrid inorganic/ECM scaffold" refers to an rECM-containing material, such as a gel that is coated onto a biocompatible inorganic structure, such as, without limitation, a metal, an inorganic calcium compound such as calcium hydroxide, calcium phosphate or calcium carbonate, or a ceramic composition. In one aspect, ultrasonication is used to aid in coating of the inorganic structure with the rECM-containing material. As used herein, the term "ultrasonication" refers to the process of exposing ultrasonic waves with a frequency higher than 15 kHz and lower than 400 kHz. In another aspect, a solution comprising rECM as described herein is coated onto an inorganic structure and is lyophilized.

As used herein, the term "coat", and related cognates such as "coated" and "coating," refers to a process comprising of covering an inorganic structure with an rECM-containing composition, such as a liquid gel to produce a hybrid inorganic/ECM scaffold. For example and without limitation, coating of an inorganic structure with ECM-containing composition can include methods such as pouring, embedding, layering, dipping, spraying.

In another aspect, the rECM-containing composition is coated onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium) of various grades or Ti 6Al4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. In one non-limiting example, the metal is femoral or acetabular component used for hip repair. In another example, the metal is a fiber or other protuberance used in permanent attachment of a prosthesis to a patient. Other compositions, including ceramics, calcium compounds, such as, without limitation, aragonite, may be preferred, for example and without limitation, in repair of or re-shaping of skeletal or dental structures. Combinations of metal, ceramics and/or other materials also may prove useful. For instance, a metal femoral component of a hip replacement may comprise a ceramic ball and/or may comprise a plastic coating on the ball surface, as might an acetabular component.

Metals, as well as other materials, as is appropriate, can be useful in its different forms, including but not limited to wires, foils, beads, rods and powders, including nanocrystalline powder. The composition and surface of metals or other materials can also be altered to ensure biocompatibility, such as surface passivation through silane treatments, coating with biocompatible plastics or ceramics, composite metal/ceramic materials. The materials and methods for their employment are well-known in the field of the present invention.

A difficulty with using metal inserts to repair a patient's skeletal structure is that the inserts must be anchored/attached to existing skeletal parts. Traditional methods employ cement and/or screws. In the case of prostheses, the prostheses are not connected to a patient's tissue except, typically, by cementing. Therefore, it is desirable to biologically attach a patient's tissue to a medical device. This may be accomplished by coating surfaces of the implant with the rECM-containing composition described herein, which will facilitate in-growth of tissue and thus attachment of the device. A variety of porous structures can be attached to the implant to create a scaffold into which the rECM-containing composition, and later cells or other tissue (e.g., bone) can infiltrate. Structures include, without limitation: woven or non-woven mesh, sponge-like porous materials, fused beads, etc. The porous scaffold will facilitate formation of a strong bond between living tissue, including bone, and the device. The "pores" of the porous scaffold may be of any size that will permit infiltration of an rECM-containing composition, optionally facilitated by ultrasound or other treatments that would assist in permeation of the gel, and later cells or other biological materials, such as bone, cartilage, tendons, ligaments, fascia or other connective tissue, into the scaffolding. In one aspect, metal fibers are attached to the device, and the metal fibers are coated with an rECM-containing composition described herein, thereby permitting in-growth of tissue within the fibers. In another aspect, a matrix of small beads is welded or otherwise attached to a surface of the device and an rECM-containing composition described herein is coated onto the bead matrix, facilitating in-growth of tissue among the beads. In one example, a device contains a protuberance of fibers, which can be inserted inside a bone, permitting fusion of the metal fibers with the bone. In one aspect, the rECM-containing composition is seeded and incubated with a suitable cell population, such as autologous osteoblasts, to facilitate bone in-growth.

A device (e.g., a prosthesis) as described herein can be coated with neutralized pre-gel and the temperature of the gel is then raised to cause the neutralized pre-gel to gel. In another embodiment, the acidic pre-gel is applied to the device or prostheses. The pre-gel on the device can then be dried, e.g. lyophilized and the entire device can be terminally sterilized, followed by packaging and distribution. The lyophilized product on the device can be hydrated by an end-user, and neutralized by application of water, saline or PBS to the device, and subsequently or concurrently raising the temperature of the device, e.g., above 37° C.

In use, the device which is coated with a suitable scaffolding and rECM-containing composition as described herein may be contacted with cells, e.g. of a patient or allogeneic cells, and the cells are allowed to infiltrate the matrix. The in-growth or infiltration of cells can occur in vivo or ex vivo, depending on optimization of methods. For example and without limitation, in the case of a femoral implant, the implant can be inserted into the femur and cells of a patient, and desirable bone tissue, infiltrates the scaffolding to fuse the device to the bone. In another embodiment, for example in the case of an artificial tendon or ligament, a biopsy of a patient's tendons or ligaments is incubated with an appropriate scaffold in order to create an autologous ligament or tendon graft.

In the Examples below, zebrafish cardiac ECM (zECM) enables endogenous regeneration of xenogeneic murine heart tissue after myocardial infarction (MI). Proliferation of multiple resident cardiac precursor cell populations and remaining cardiomyocytes contributes to the regeneration and correlates with approximately 61% recovery of cardiac ejection fraction (defined as [Δ(treatment−saline)/Δ(healthy−saline)]×100%). Under identical conditions, murine cardiac ECM (mECM) yields 17% functional recovery with minimal proliferation of cardiac precursor cells and cardiomyocytes.

Examples

Evolutionarily primitive species generally have higher regenerative capability than mammals. An example is the major difference in the regenerative capacity between adult zebrafish and mammalian hearts. An adult zebrafish heart can fully regenerate after up to 20% volumetric loss by ventricular amputation while a mammalian counterpart cannot sustain such an injury. On the other hand, embryonic mammals also possess robust regenerative capability that is rapidly lost during the postnatal development. For example, a neonatal mouse can regenerate up to 10% of its heart apex after ventricular resection, an ability that disappears within one week after birth. More specifically, although mammalian cardiomyocytes proliferate rapidly during the fetal period, their proliferative capacity quickly ceases after birth, with the exception of a brief proliferative burst at preadolescence. Despite a low turnover rate throughout the adulthood, most adult mammalian cardiomyocytes remain mitotically quiescent and are unable to spontaneously regenerate after severe injuries such as myocardial infarction (MI). Consequently, how the regenerative capacity lost in evolution can be effectively restored or reactivated in adult mammalian hearts remains to be explored. The ECM may contribute to this evolutionary difference in cardiac regeneration. We hypothesize that ECM in the zebrafish heart contributes to its regenerative capability and may be used to induce mammalian heart regeneration.

Decellularized mammalian ECM has been extensively investigated in tissue engineering and regenerative medicine. Mammalian cardiac ECM has been reported beneficial when administered to the ischemic heart. However, instead of regeneration, fibrosis typically occurs in adult mammalian hearts after severe ischemic insults, which in turn impedes further structural or functional recovery. We believe that the ECM from a regenerative tissue is more likely to revitalize mammalian hearts after MI than that from a fibrosis-prone tissue. Besides, mammalian organs are relatively thick and thus typically require the involvement of detergents or other potent chemicals for their decellularization. This may reduce the availability and activity of trophic molecules in the decellularized ECM and alter their three dimensional configuration. In sharp comparison, the zebrafish ventricular wall consists of only 4 to 5 layers of cardiomyocytes in a compact myocardium and is <20 μm thick. This enables a physical decellularization protocol minimizing chemical perturbations to the native ECM composition and structure. In addition, a mechanical process may be used to dissociate the decellularized ECM into fine powders for injection without any chemical or biological reagent to further preserve the integrity of zebrafish heart ECM. Zebrafish is small, easy to grow, and is routinely raised in large populations allowing researchers to pool zebrafish hearts for decellularization. In the current example, a protocol is established to physically decellularize zebrafish cardiac ECM (zECM) from normal and healing (3 dpa, 3-day post amputation) zebrafish hearts. zECM is characterized, the bioactivity of zECM on human cardiac precursor cell populations is examined, and the regenerative capability of zECM in vivo was investigated using acutely infarcted adult mouse heart as a model organ and decellularized adult mouse cardiac ECM (mECM) as a control. The role of the epidermal growth factor receptor (EGFR)-2 receptor tyrosine kinase (also known as ErbB2, Neu, HER2) was investigated in zECM-induced effects in ischemic hearts. This proof-of-concept study explores the potential of zECM as a new biological material for cardiac tissue regeneration, departing from conventional focuses on mammalian cardiac ECM.

Materials and Methods

Animals.

Adult (6-12 months) wild-type AB* zebrafish (mixed male and female) were maintained at 28° C. Approximately 850 zebrafish were used for this study. A total of 115 male BALB/cJ mice at 9-12 weeks old (Jackson Laboratory, Bar Harbor, Me., USA) were used for this study.

Ventricular Amputation and Procurement of Zebrafish Hearts.

To obtain healing zebrafish hearts, ventricular resection surgeries were performed. Briefly, zebrafish were anesthetized in Tricaine (ethyl 3-aminobenzoate methanesulfonate, i.e. MS-222, tricaine methanesulfonate, A-5040; Sigma-Aldrich, St. Louis, Mo., USA) and placed dorsally in a humid sponge. A small incision (scalpel 0.15 mm, Fine Science Tools, Foster City, Calif., USA) was made to expose the ventricle and approximately 20% of the ventricular apex was microscopically removed using iridectomy scissors (Fine Science Tools). After the surgery, fish were returned to water and stimulated to breathe with air bubbles. At 3 days post amputation (3 dpa), methylene blue (an anti-fungal/bacterial agent) was added to the fish tank 1 hr before harvesting Amputated zebrafish and age-matched uninjured counterparts were lethally anesthetized with Tricaine. Zebrafish were then dipped 3 times in 70% ethanol immediately before harvesting. The whole hearts were extracted with sterile tools and placed on a sterile plate under the dissection microscope. To accentuate the regenerating ventricular apex, only ⅔ of the ventricle (including apex) was collected for the decellularization. Normal zebrafish ventricles were collected in the same manner (only apical ⅔). Tools were sterilized with 70% ethanol between each fish. Collected ventricles were immediately washed 3 times in 4% Penicillin/Streptomycin/Amphotericin-B with 1% Gentamycin (P/S/A/G) solution and transported back to the laboratory. Approximately 50-60 ventricles were pooled together per batch to obtain sufficient materials for decellularization. All ventricles were washed extensively in 4%, 2%, and 1% gradient P/S/A/G solutions (two times each) in the biosafety cabinet before being subjected to the decellularization process.

Procurement of Adult Mouse Ventricular Tissues.

Mice were sacrificed, immersed in 70% ethanol for 30 seconds, and wiped clean before removing hearts with two sets of sterile tools (one set for cutting the skin and opening the chest and another set for removing the heart). Collected hearts were immediately washed 3 times in 4% P/S/A/G solution and transported back to the laboratory. Left ventricles were then dissected out and finely chopped to <1 mm³ with sterile tools in the biosafety cabinet. All mouse ventricular pieces were washed extensively in 4%, 2%, and 1% gradient P/S/A/G solutions (two times each) before being subjected to the decellularization process.

Decellularization of Cardiac ECM.

Zebrafish ventricles and mouse ventricular pieces were carefully transferred to individually weighed, sterile 1.5 ml microcentrifuge tubes containing 1 ml 1% P/S/A/G solution. Tubes were centrifuged at 6,000 g for 3 minutes with careful removal of supernatants and then individually weighed to obtain the collective wet weights of samples. Tubes were subsequently replenished with 1 ml 1% P/S/A/G solution, vortexed to evenly distribute contents, parafilmed to seal caps, and subjected to 3 freeze-thaw cycles by submerging in liquid nitrogen for 10 minutes and then completely thawing at 37° C. in water bath. Alternatively, tubes can be chilled with dry ice for at least 30 minutes or at −80° C. for at least 1 hour per cycle before being completely thawed at 37° C. in water bath. Tubes were centrifuged at 6,000 g for 3 minutes with careful removal of supernatants and replenished with 1 ml 1% P/S/A/G solution between each freeze-thaw cycle and then vortexed to ensure even distribution of contents before starting the next cycle. After 3 cycles, erythrocyte lysis was performed twice by adding 1 ml erythrolysis buffer (ELB) to resuspend contents, incubating for 20-30 minutes at room temperature, and centrifuging at 6,000 g for 3 minutes. Samples were then subjected to 2 more freeze-thaw cycles as described above with 1 ml 1% P/S/A/G solution. Samples were subsequently incubated with 250 U/ml deoxyribonuclease I (DNase I, 18047-019) and 25 U/ml ribonuclease A (RNase A, AM2274) at 37° C. for at least 1 hour (both from Life Technologies, Grand Island, N.Y., USA). Treatment with DNase I and RNase A was repeated after centrifugation at 6,000 g for 3 minutes and careful removal of the supernatant. After 2 rounds of DNA/RNA lysis, samples were washed three times with sterile 0.9% normal saline (Baxter Healthcare, Deerfield, Ill., USA) and frozen at −80° C. for 1 hour. Samples were then washed with 0.9% normal saline, centrifuged at 6,000 g for 3 minutes with complete removal of supernatants, and subjected to lyophilization for 72 hours in original tubes in a sterilized chamber Immediately after lyophilization, tubes were individually weighed to obtain the collective dry weights of lyophilized products. Lyophilized samples were finely crushed and ground for 15-20 minutes into fine powders in original tubes placed in a liquid nitrogen-cooled mini mortar (H37260-0100; Bel-Art Products, Wayne, N.J., USA). Lyophilized powders were stored at −80° C. for future use.

Preparation of Cardiac ECM Suspension and Particle Size Measurement.

Prior to applications, lyophilized cardiac ECM powders were weighed in a sterile container, resuspended in 0.9% normal saline, and sonicated in cool water for 15 min Large particles were then removed by centrifugation at 300×g. Cardiac ECM suspension was collected for immediate use or stored on dry ice for later use. Cardiac ECM particle size was measured by Zetasizer Nano ZS90 (Malvern, Worcestershire, UK) and reported as the mean from 25 measurements. Results were then averaged from measurements of three independent samples. For in vivo administration, 0.5 mg of lyophilized zECM or mECM powders were resuspended in 30 µl of 0.9% normal saline, sonicated and centrifuged as described above, and transported on dry ice to the operating room prior to the administration.

ECM Composition Analysis.

The amount of collagen in cardiac ECM was measured with Sircol collagen assay kit (Biocolor Ltd, Carrickfergus, County Antrim, UK) following the manufacturer's manual. Briefly, collagen was extracted by fragmentation reagent provided with the kit. Samples were incubated at 65° C. for 2 to 3 hrs and precipitated out by adding Sircol dye reagent. Ice-cold acid-salt wash reagent was gently layered onto the collagen-dye pellet to remove unbound dye. Samples were centrifuged at 12,000 rpm for 10 min Precipitates were further recovered by the addition of alkali reagent. Absorbance was measured at 550 nm with a SynergyMX plate reader (Biotek, Winooski, Vt., USA). The amount of elastin in cardiac ECM was measured with Fastin elastin assay kit (Biocolor Ltd). Briefly, elastin was extracted from tissue samples by digesting with oxalic acid at 100° C. and precipitated out using the supplied elastin-precipitating reagent. Precipitates were then incubated with elastin dye reagent followed by its dissociation in dye dissociation reagent. Absorbance was measured at 513 nm. The amount of glycosaminoglycans (GAGs) was measured using Blyscan sulfated glycosaminoglycan kit (Biocolor Ltd). Briefly, tissue samples were digested with the supplied papain extraction reagent at 65° C. Extracted GAGs were incubated with Blyscan dye reagent to form precipitates of sulfated glycosaminoglycan-dye complex. Precipitates were further dissociated by the dissociation reagent. Absorbance was measured at 656 nm.

Myocardial Infarction Model.

The induction of myocardial infarction (MI) and intramyocardial injections were performed. In brief, after the induction of anesthesia with 4% isoflurane gas, mice were intubated and inhalationally anesthetized with 2% isoflurane gas throughout the surgery. MI was microscopically induced by permanent ligation of the left anterior descending coronary artery (LAD). Mice were then randomly assigned to one of the four groups: hzECM, nzECM, mECM, and saline control. Five minutes after the induction of infarction, 30 µl of zECM or mECM suspension was injected at three sites of the ischemic myocardium (center and two borders of the infarct; 10 µl for each site). Control mice received injections of 30 µl normal saline. The investigator inducing MI and performing injections was blinded to the content of the injectant. For ErbB2 inhibition in vivo, an ErbB2 inhibitor AG825 (sc-202045A; Santa Cruz Biotechnology, Dallas, Tex., USA) was dissolved in dimethyl sulfoxide (DMSO) and intraperitoneally injected once at 5 mg/kg (20 to 25 µl in volume) immediately after the cardiac ECM administration.

Echocardiography.

Echocardiographic studies were performed by a blinded investigator repeatedly before surgery and at 5 days, 2 weeks, and 6 weeks post-surgery to assess the cardiac function. Briefly, mice were initially anesthetized with 2% isoflurane gas and subsequently maintained at 1-1.5% isoflurane gas throughout the echocardiographic study. Mice were then immobilized on a heated stage equipped with electrocardiography. Heart rate and respiratory rate were continuously monitored. The body temperature was maintained at 37° C. Echocardiographic parameters were measured using a high-frequency linear probe (MS400, 30 MHz) connected to a high-resolution ultrasound imaging system (Vevo 2100; FUJIFILM VisualSonics, Toronto, Ontario, Canada). M- and B-mode frames were acquired at a frame rate of 235 Hz during each scan. At least three independent M- and B-mode scans (300 frames per scan) were recorded respectively for each animal at each time point. End-systolic dimension (ESD) and end-diastolic dimensions (EDD) were determined from short axis images of the LV using M-mode scan. Ten consecutive beats were measured from M-mode frames. Results were averaged. End-systolic area (ESA) and end-diastolic area (EDA) were measured from short-axis images of the LV using B-mode scan (minimum and maximum LV chamber area respectively). Functional parameters, including the LV fractional shortening (LVFS), LV fractional area change (LVFAC), and LV ejection fraction (LVEF), were determined as previously described (Pollick C, et al. Echocardiographic and cardiac doppler assessment of mice. *Journal of the American Society of Echocardiography.* 1995; 8:602-10 and Wandt B, et al. Echocardiographic assessment of ejection fraction in left ventricular hypertrophy. *Heart.* 1999; 82:192-8). Mice which died, displayed behavioral abnormality, or were sacrificed for histological analysis prior to 6 weeks post-injection were not included in echocardiographic studies.

Ultrasonic Strain Analysis.

The ultrasound B-mode frames of LV short-axis view acquired at 6 weeks post-MI were analyzed using a cardiac strain analysis software package (VevoStrain, Vevo 2100; FUJIFILM VisualSonics, Toronto, Ontario, Canada) by a blinded investigator (N=3 per group)(O'Donnell M, et al. Internal displacement and strain imaging using ultrasonic speckle tracking. *Ultrasonics, Ferroelectrics, and Frequency Control, IEEE Transactions on.* 1994; 41:314-25 and Lubinski M A, et al. Speckle tracking methods for ultrasonic elasticity imaging using short-time correlation. *Ultrasonics, Ferroelectrics, and Frequency Control, IEEE Transactions on.* 1999; 46:82-96). Five regions of interest (ROI) were selected along the LV mid-wall including one ROI in the anterior lateral (infarcted area) and four ROIs in the anterior medial, posterior lateral, posterior, posterior medial (non-infarct areas) walls of the LV as shown in FIGS. 4A-4E. Radial and circumferential intercardiac strain (i.e. change in strain from end-diastole to end-systole) in all five ROIs were obtained. The end-diastole and end-systole were determined respectively according to EDA and ESA described above. The estimated intercardiac strain in the infarcted area was normalized to the average intercardiac strain of the four ROIs in unaffected LV walls.

Primary Human Cell Culture.

Primary human adult cardiac stem cells (hCSC) were purchased from Celprogen Inc. (36099-26; Torrance, Calif., USA) and expanded with hCSC complete media with serum (hCSC-CM, M36099-265; Celprogen Inc.) and extracellular matrix pre-coated T75 flasks (E36099-26; Celprogen Inc.), according to the manufacturer's protocol. Primary human heart perivascular MSC precursors (hHP) were isolated from ventricular myocardium and purified by flow cytometry (Chen W C W, et al. Human Myocardial Pericytes: Multipotent Mesodermal Precursors Exhibiting Cardiac Specificity. *STEM CELLS.* 2015; 33:557-73). hHP were expanded in complete growth media (hHP-CM) containing DMEM high glucose (11965-118, without sodium pyruvate), 20% fetal bovine serum (FBS), and 1% Penicillin/Streptomycin (P/S) (all from Life Technologies, Grand Island, N.Y., USA). hCSC at passage 2-4 and hHP at passage 6-8 were used in subsequent assays.

Measurement of Cell Proliferation in Vitro.

To investigate the effect of zECM on the proliferation of hCSC and hHP under stress, we utilized two stressed culture conditions. For the nutrient-deprivation stress assay, we used 25% complete culture medium for hCSC (25% hCSC-CM) and DMEM supplemented with 2.5% FBS and 1% P/S for hHP (2.5% PBS-CM). For the ischemic stress assay, we cultured cells under 2.5% $O_2$ concentration (with 5% $CO_2$ and 92.5% $N_2$) in addition to the nutrient-deprivation. Briefly, hCSC-CM and hHP-CM were diluted at 1:3 and 1:7 ratios respectively with DMEM high glucose containing 1% P/S before supplementing with 25 µg hzECM, nzECM, or mECM per 96 well. Full CM and diluted CM without ECM served as positive and negative controls respectively. hCSC were first plated in extracellular matrix pre-coated 96-well plates (E36099-26; Celprogen Inc.) in triplicate ($10^3$ cells/well) overnight with 100 µl 25% hCSC-CM. hHP were first plated in regular 96-well culture plates (Corning, Tewksbury, Mass., USA) in triplicate ($10^3$ cells/well) overnight with 100 hHP-CM. After washing, media were replaced with 200 µl 25% hCSC-CM and 2.5% FBS-CM, with or without ECM, for hCSC and hHP respectively. Distinct medium dilutions were applied for different cell types due to their differential cell doubling time and endurance under stress. All plates were subsequently incubated under ambient or 2.5% $O_2$ conditions for 4 days. At respective time points, after washing, 20 µl CellTiter 96® AQueous One Solution Cell Proliferation Assay (MTS) reagent (Promega, Madison, Wis., USA) in DMEM was added to all wells containing 100 µl fresh media. The plate was then incubated at 37° C. for 2.5 hrs, at which point the absorbance at 490 nm (with reference at 650 nm) was read with Infinite 200 PRO plate reader (Tecan, Männedorf, Switzerland). All experiments were independently repeated 3 times. Results were individually normalized to each experimental control and then averaged.

Measurement of Cell Migration in Vitro.

A transwell chemotaxis assay was used to investigate the effect of zECM on the migration of hCSC and hHP under nutrient-deprivation stress (with 25% hCSC-CM for hCSC and 2.5% PBS-CM for hHP as described above). Media supplemented with 125 µg hzECM, nzECM, mECM, or saline (negative control) were loaded into bottom wells. hCSC and hHP were seeded in transwell inserts with 8-µm pore size (Millipore, Billerica, Mass.) at a density of 10,000 cells/cm². After incubation at 37° C. for 6 hrs, non-migrated cells were removed with cotton swabs. Migrated cells were fixed with methanol for 10 min and stained with Quant-iT PicoGreen dsDNA reagent (P7581; Thermo Fisher Scientific, Waltham, Mass., USA). Fluorescent images were captured by Nikon Eclipse Ti fluorescence microscope equipped with NIS-Elements AR imaging software (both from Nikon, Tokyo, Japan). The number of migrated cells was quantified and averaged from 3 independent images taken in 3 different areas per sample per group (N=4). The cell number of each group was individually normalized to the average number of cells in the saline control group.

Histological and Immunohistochemical Analyses.

Animals were sacrificed at 3 days and 6 weeks post-surgery. Hearts were arrested in diastole by intraventricular injection of 1M potassium chloride (KCl) and processed as previously described (Chen C-W, et al. Human Pericytes for Ischemic Heart Repair. *STEM CELLS.* 2013; 31:305-16). For histology and immunohistochemistry, harvested hearts were flash frozen in 2-methylbutane (M32631; Sigma-Aldrich, St. Louis, Mo., USA) pre-cooled in liquid nitrogen and serially cryosectioned at 8 µm thickness from the apex to the ligation level (approximately 0.5 mm in length). Each series contains 18-21 heart sections, which are roughly 200 um apart natively and collected on one glass slide. Sections were fixed in a pre-cooled (−20° C.) mixture of methanol (322415; Sigma-Aldrich) and acetone (320110; Sigma-Aldrich) (1:1) for 5 min or in 4% paraformaldehyde (P6148; Sigma-Aldrich) for 8 min at room temperature (RT) immediately prior to staining. Hematoxylin and eosin (H&E) staining was performed following the standard protocol. Masson's trichrome staining kit (IMEB, San Marcos, Calif., USA) was used to reveal collagen deposition on heart serial cross-sections, following the manufacturer's instruction.

For immunohistochemistry, non-specific antibody binding was blocked with 10% donkey or goat serum for 1-2 hours at room temperature (RT), and, if necessary, with the Mouse-on-Mouse antibody staining kit (Vector Laboratories, Burlingame, Calif., USA). For evaluation of chronic inflammation, sections were incubated overnight at 4° C. with rat anti-mouse CD68 primary antibody (1:200, Ab53444; Abcam, Cambridge, Mass., USA), followed by goat anti-rat-Alexa488 IgG (1:400, A-11006; Life Technologies). To examine murine cardiac stem cells (CSC), heart mesenchymal stem/stromal cell (cMSC), and epicardium-derived progenitor cells (EPDC), sections were first incubated overnight at 4° C. with rat anti-mouse CD117 (1:50, CL8936AP; Cedarlane Laboratories, Burlington, N.C., USA), goat anti-mouse PDGFR-beta (1:100, AF1042; R&D Systems, Minneapolis, Minn., USA), or rabbit anti-Wilm's Tumor (1:100, E3990; Spring Bioscience, Pleasanton, Calif., USA) antibody respectively, followed by donkey anti-rat-Alexa594 IgG (1:400, A-21209; Life Technologies), donkey anti-goat Alexa594 IgG (1:400, A-11058; Life Technologies), or donkey anti-rabbit-Cy3 IgG (1:300, 711-165-152; Jackson ImmunoResearch Laboratories, West Grove, Pa., USA) respectively at RT for 1 hour. For the detection of cardiomyocytes, sections were incubated overnight at 4° C. with mouse anti-cardiac troponin T primary antibody (cTnT, 1:200, ab10214; Abcam), followed by goat anti-mouse-Alexa488 IgG (1:400, A-11001; Life Technologies) at RT for 1 hour. To detect proliferating cells, after the first staining for one of the cell lineage markers above, a second overnight incubation was performed at 4° C. with rabbit anti-mammalian Ki67 primary antibody (1:200, ab15580; Abcam), followed by donkey anti-rabbit-Alexa488 IgG (1:400, A-21206; Life Technologies) at RT for 1 hour. For the detection of cells expressing ErbB2, after the first staining of cTnT, a second overnight incubation was performed at 4° C. with chicken anti-ErbB2 primary antibody (1:100, ab14027; Abcam), followed by goat anti-chicken IgY (H+L)-Alexa594 (1:400, A-11042; Life Technologies) at RT for 1 hour. To detect elastin, sections were incubated overnight at 4° C. with mouse anti-elastin primary antibody (1:100, sc-374638; Santa Cruz Biotechnology), followed by goat anti-mouse-Alexa488 IgG at RT for 1 hour. Nuclei were stained with 4',6-diamidino-2-phenylindole (DAPI) (1:1000, D1306, Life Technologies) at RT for 5 min Immunofluorescent images were taken by Nikon Eclipse Ti fluorescence microscope equipped with NIS-Elements AR imaging software (both from Nikon).

For the histological analysis of the zebrafish heart, zebrafish were euthanized using 0.168 g/L Tricaine for 3-5 minutes. Zebrafish hearts were collected in cold PBS and fixed in 4% paraformaldehyde for 2 hours. After two washes in PBS, hearts were cryopreserved overnight with 30% sucrose in PBS. Samples were embedded in tissue freezing medium (39475237; Leica Biosystems, Buffalo Grove, Ill., USA). Tissue blocks were cryosectioned at 14 µm thickness. Sections were allowed to dry at 37° C. for 2 hours before storing them at −20° C. AFOG staining was performed as previously described (1). To detect neuregulin-1 (NRG1) in situ, sections were incubated with rabbit anti-NRG1 antibody (1:100, ab27303; Abcam) overnight at 4° C., followed by goat anti-rabbit horseradish peroxidase-conjugated IgG (1:1000, G-21234; Life Technologies) at RT for 1 hour. Images were captured with Leica MZ 16 microscope with a QImaging Retiga 1300 camera (Leica Biosystems). To fluorescently detect NRG1, mouse and zebrafish ventricular tissue sections were incubated with (1:100, ab27303; Abcam) overnight at 4° C., followed by donkey anti-rabbit-Alexa488 IgG (1:400, A-21206; Life Technologies) at RT for 1 hour. Nuclei were stained with DAPI at RT for 5 min Immunofluorescent images were taken by Nikon Eclipse Ti fluorescence microscope equipped with a QImaging Retiga 1300 camera.

Scanning Electron Microscopy.

Fresh and decellularized normal and healing zebrafish hearts and respective lyophilized powers were processed for scanning electron microscopy (SEM). Briefly, fresh whole hearts were fixed in 2.5% glutaraldehyde (G5882, Sigma-Aldrich) in 0.1 M PBS (pH 7.4) for at least 10 minutes. Ventricles were dissected out under a dissection microscope and then continued fixing for not more than 50 minutes. Tissues were washed thoroughly in 3 changes of 0.1 M PBS for 15 minutes each. Tissues were fixed in 1% OsO4 in 0.1 M PBS for 60 minutes and then washed thoroughly in 3 changes of 0.1 M PBS for 15 minutes each. Tissues were subsequently dehydrated in graded series of ethanol (in PBS) for 15 minutes each: 30%, 50%, 70%, 90%, and 3×100%. All specimens were then subjected to critical point dry, mounted on studs, and sputter coated with 3.5 nm of gold/palladium alloy using a Cressington 108auto sputter coater (Cressington Scientific Instruments, Watford, England, UK. Samples were then imaged on a JSM-6335F scanning electron microscope (SEM; JEOL USA, Peabody, Mass., USA). Samples can be stored in a desiccator for future imaging.

Western Blot.

Total proteins were extracted and purified using protein extraction reagents (Lysis RIPA buffer, 040-483; Protein-Simple, San Jose, Calif., USA) for zebrafish and mouse ventricular tissues (N=4 per group). The equivalent of 50 µg protein from each sample was separated by 11% gel (for 10 ml gel: 3.85 ml DI water, 3.53 ml 30% acrylamide, 2.6 ml Tris-HCl (pH8.8), 50 µl APS, and 10 µl TEMED; all from Bio-Rad Laboratories, Hercules, Calif., USA) and then transferred onto a PVDF membrane (BioTrace PVDF Transfer Membrane, 66594; Port Washington, N.Y., USA). After blocking with 5% bovine serum albumin (OmniPur BSA, Fraction V, 2930-100GM; EMD Millipore, Billerica, Mass., USA), membranes were incubated with the anti-NRG1 antibody (1:300, ab27303; Abcam) at 4° C. with shaking at 90 rpm overnight. Membranes were then washed with TBS buffer and treated with a goat-anti-rabbit secondary antibody (1:1000, SC-2004; Santa Cruz Biotechnology) for 2 h at room temperature. The signals were visualized with the ChemiDic XRS+ Imaging System (Bio-Rad Laboratories). The band densities were quantified with Image J (National Institutes of Health).

Statistical Analysis.

All measured data are presented as mean±standard deviation (SD). Statistical differences between groups were analyzed by Student's t-test (two groups), one-way ANOVA (multiple groups), or two-way repeated ANOVA (repeated echocardiographic measurements) with 95% confidence interval. Statistical significance was set at $p \leq 0.05$. Bonferroni multiple comparison test was performed for ANOVA post-hoc analysis. Statistical analyses were performed with SigmaStat 3.5 (Systat Software, San Jose, Calif., USA), GraphPad Prism 5.0 (GraphPad Software, La Jolla, Calif., USA), and SPSS21 (IBM, Armonk, N.Y., USA) statistics software.

Results

Production and Characterization of Decellularized Zebrafish Cardiac ECM.

Figure 1:
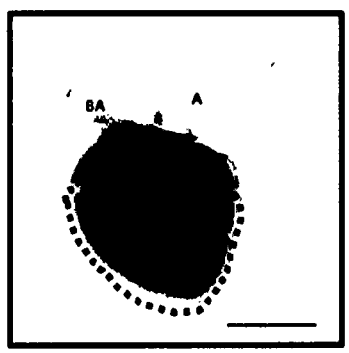
FIGS. 1A and 1B. Amputated zebrafish hearts and decellularization processes.
Figure 1:
Figure 1:
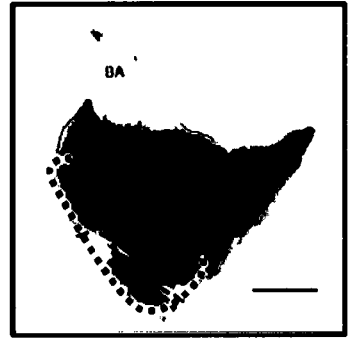
Figure 1:
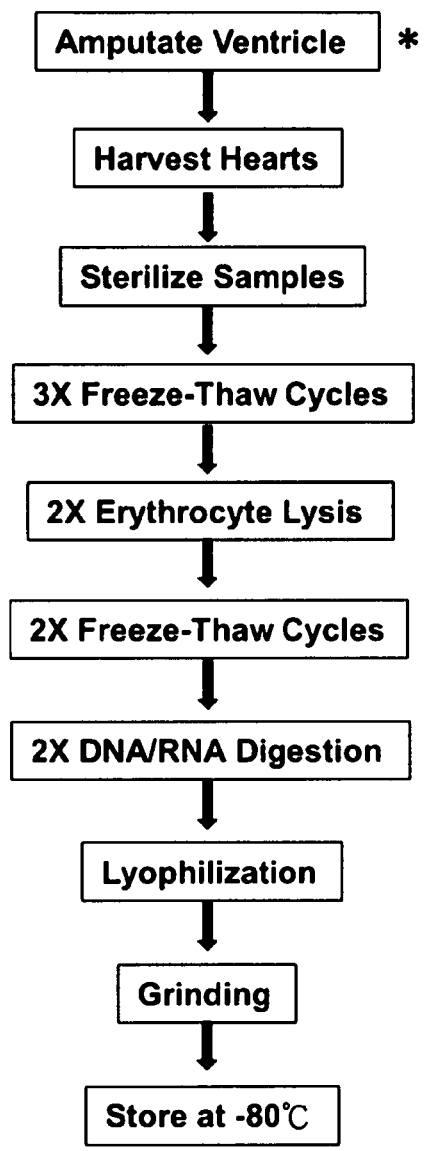

A physical decellularization protocol was developed with mechanical dissociation to minimize the use of chemical or biological reagents that may disturb the native ECM architecture and associated trophic factors, taking advantage of the very thin zebrafish ventricular wall. To compare the difference in the regenerative capacity of cardiac ECM between healthy and regenerating zebrafish hearts, normal and healing (3 dpa) adult zebrafish ventricles (FIG. 1(A)) were harvested and thoroughly washed in antibiotic/antifungal solutions. Typically 50-60 zebrafish ventricles were collected and pooled per batch. Healthy adult mouse ventricles were used as a treatment control and minced into very small fragments (<1 mm$^3$) for physical decellularization. Briefly, all 3 groups were decellularized by repeated freeze-thaw cycles with removal of red blood cells and DNA/RNA by the erythrolyse buffer and DNase/RNase respectively (FIG. 1(B)). After lyophilization, ECM was mechanically ground into fine powders in a liquid nitrogen-chilled container and stored at −80° C.

Figures 2B, 2C:
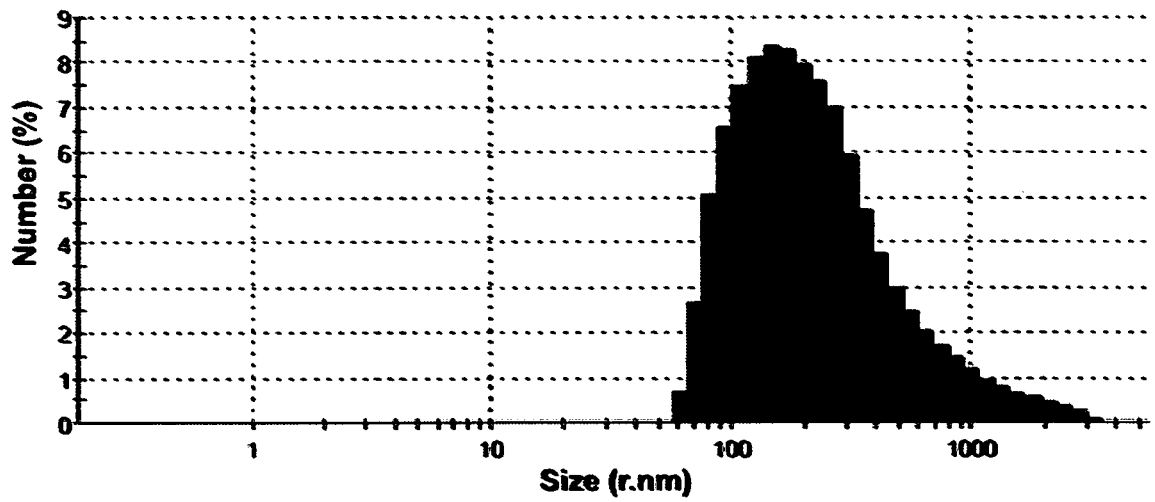

Scanning electron microscopy (SEM) was used to observe the morphological change following decellularization. SEM images revealed the differences of fresh and decellularized zebrafish ventricular tissues and ECM particles (FIG. 2A). Dynamic light scattering showed that the decellularized normal (nzECM) and healing (hzECM) zebrafish cardiac ECM were micro- to nano-particles with an average radius of approximately 306.3 nm (FIG. 2B). The final yield of lyophilized zECM powders was approximately 6-8% of the original wet weight with <0.1% residual nucleotide compared with native tissues. Analyses of cardiac ECM composition revealed that nzECM contains approximately 73.2% of collagen (p<0.01), 137.1% elastin (p<0.05), and 142.1% glycosaminoglycans (GAGs) (p<0.05) when compared with decellularized adult mouse cardiac ECM (mECM) (FIG. 2C).

Bioactivity of Decellularized zECM In Vitro.

Figure 3F:
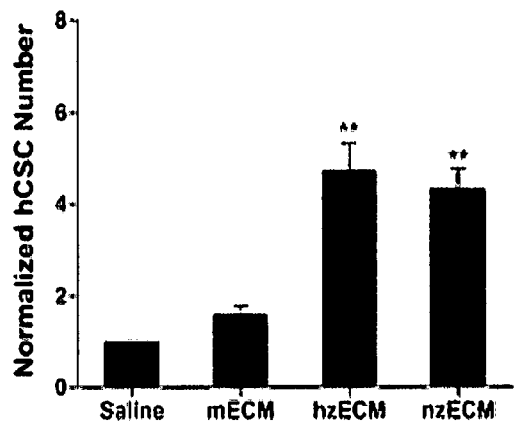
FIGS. 3A-3G. Bioactivity of zECM on human cardiac precursor cell proliferation and migration.

As a first step to investigate the cardiac regenerative potential of zECM for mammalian hearts, we examined the bioactivity of decellularized zECM on the proliferation and migration of human cardiac precursor cell populations in vitro. To simulate the harsh microenvironment in the ischemic myocardium, stressed growth conditions were applied, including nutrient-deprivation and dual hypozxia/nutrient-deprivation, to cell cultures. Both hzECM and nzECM displayed pro-proliferative effects on human cardiac stem cells (hCSC) and human heart perivascular mesenchymal stem/stromal cell (MSC)-like precursors (hHP) under each stressed culture condition. When deprived of nutrition (hCSC: 25% complete culture media; hHP: 2.5% fetal bovine serum) for 4 days, hzECM-treated hCSC and hHP both exhibited significantly higher proliferation rate when compared with mECM or non-treated controls (hCSC, both p<0.005; hHP, both p<0.05), whereas nzECM- and mECM-treated cells showed notably faster growth than control cells (all p<0.05) (FIGS. 3A and 3B). However, under dual hypoxic (2.5% $O_2$) and nutritional deprivation, zECM markedly enhanced hCSC and hHP proliferation, particularly hzECM (both p<0.01), while mECM showed no stimulatory effect (FIGS. 3C and 3D).

Figure 3H:
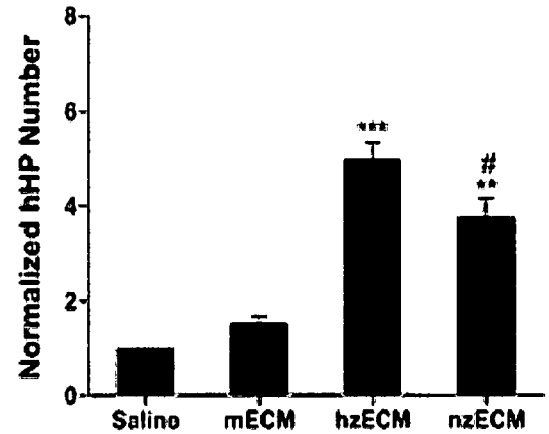
Figure 3G:
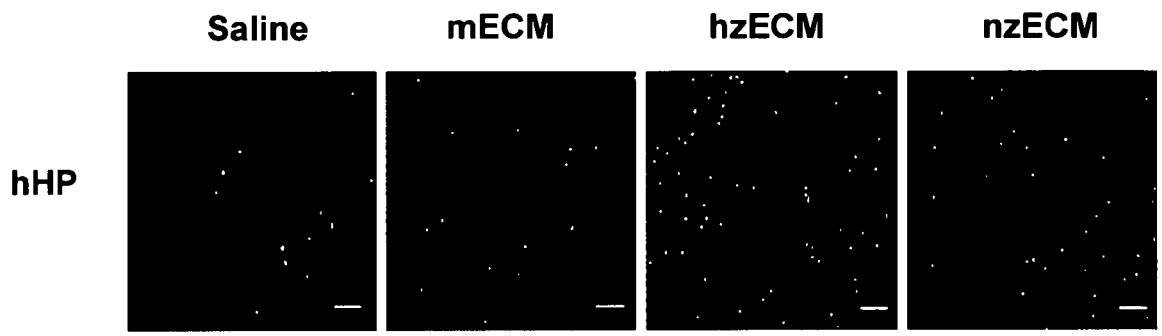

To simulate cell migration in the ischemic myocardium, nutrient-deprived culture condition were applied in the transwell chemotaxis assay with induction of different decellularized cardiac ECM. The results showed that hzECM and nzECM, but not mECM, induced prominent migration of hCSC (FIG. 3E) and hHP (FIG. 3G). Quantification data indicate significantly more hCSC (FIG. 3F; both p<0.01) and hHP (FIG. 3H; hzECM, p<0.001; nzECM, p<0.01) migrated under the hzECM and nzECM inductions than under the mECM induction and saline control. hzECM induced notably higher hHP migration than nzECM under stress (FIG. 3H; p<0.05). Together these data suggest the preservation of zECM bioactivity after decellularization and pro-proliferative and chemotactic effects of zECM on two human cardiac precursor cell populations under stressed microenvironment.

Intramyocardial Administration of zECM Improves Cardiac Function.

Figure 4A:
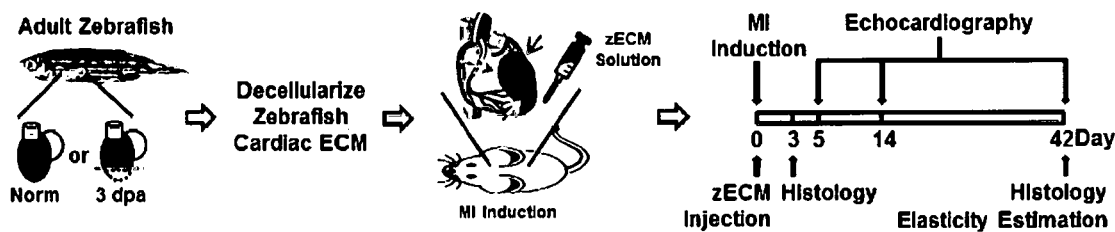
FIGS. 4A-4E. Echocardiographic analyses of cardiac function.
Figure 4B:
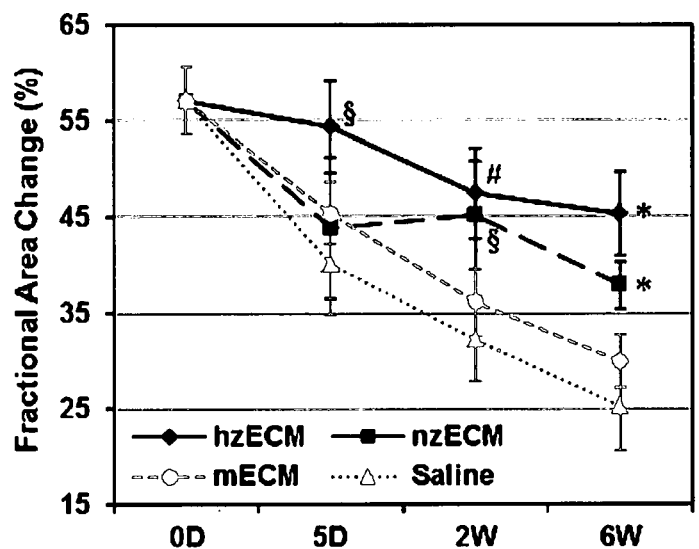
Figure 4C:
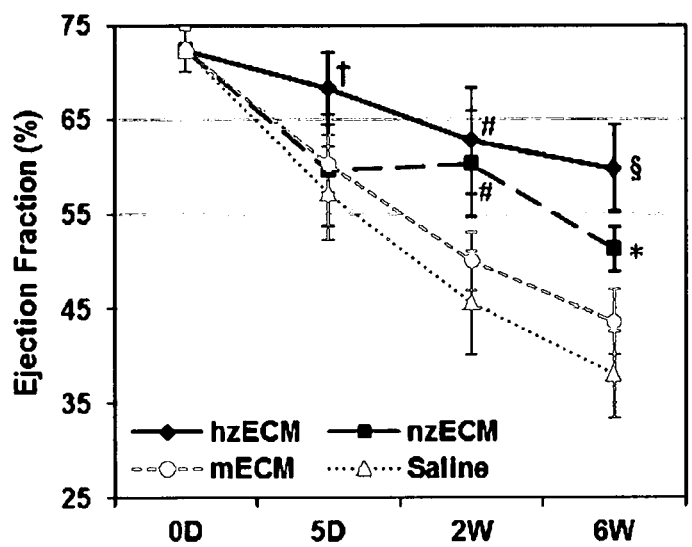
Figure 4D:
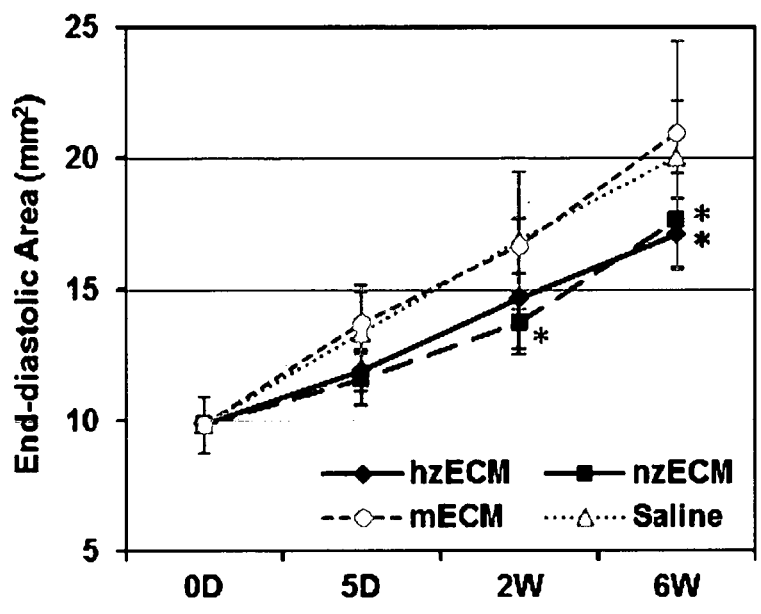
Figure 4E:
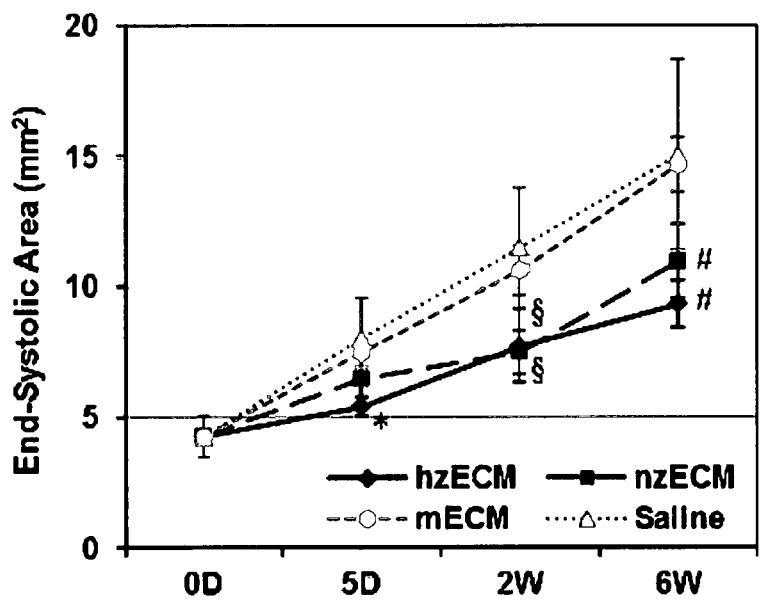

The efficacy of decellularized zECM on cardiac function was investigated in an adult mouse acute MI (AMI) model (FIG. 4A). All mice that survived the MI induction surgery have lived through the 6-week experimental duration. Long-term cardiac function was repeatedly assessed by M- and B-mode echocardiography before (baseline) and after surgery at 5, 14, and 42 days (FIGS. 5A and 5B). The results showed that hzECM exhibited substantially higher overall treatment efficacy in left ventricular fractional area change (FIG. 4B) and ejection fraction (FIG. 4C) than all other groups (all p<0.001) while nzECM was significantly higher than mECM and saline control (all p<0.005). mECM was less effective but exhibited notable beneficial effects when compared with saline (both p<0.05). These data indicate significant preservation of left ventricular contractility after AMI, following zECM treatment. Moreover, both hzECM and nzECM had markedly reduced left ventricular end-diastolic area (FIG. 4D) and end-systolic area (FIG. 4E) than mECM and saline (all p<0.005), suggesting amelioration of progressive left ventricular dilatation with zECM treatment. All echocardiographic measurements are listed in Table 1.

TABLE 1

Echocardiographic parameters of infarcted
mouse hearts following ECM treatment

| Mean ± SD (%) | 0 D | 5 D | 2 W | 6 W |
|---|---|---|---|---|
| *Fractional Area Change* | | | | |
| hzECM | 57.12 ± 3.53 | 54.35 ± 4.83 | 47.47 ± 4.74 | 45.29 ± 4.40 |
| nzECM | 57.12 ± 3.53 | 43.80 ± 7.35 | 45.13 ± 5.67 | 37.88 ± 2.44 |
| mECM | 57.12 ± 3.53 | 45.39 ± 3.21 | 36.13 ± 3.50 | 29.97 ± 2.77 |
| Saline | 57.12 ± 3.53 | 40.05 ± 5.28 | 32.27 ± 4.43 | 25.23 ± 4.72 |
| *Ejection Fraction* | | | | |
| hzECM | 72.36 ± 2.24 | 68.24 ± 3.84 | 62.75 ± 5.62 | 59.83 ± 4.58 |
| nzECM | 72.36 ± 2.24 | 59.64 ± 5.87 | 60.33 ± 5.54 | 51.31 ± 2.39 |
| mECM | 72.36 ± 2.24 | 60.32 ± 3.02 | 50.03 ± 3.14 | 43.61 ± 3.46 |
| Saline | 72.36 ± 2.24 | 57.21 ± 4.88 | 45.57 ± 5.47 | 38.02 ± 4.56 |

| Mean ± SD ($mm^2$) | 0 D | 5 D | 2 W | 6 W |
|---|---|---|---|---|
| *End-Diastolic Area* | | | | |
| hzECM | 9.83 ± 1.08 | 11.89 ± 0.77 | 14.65 ± 1.90 | 17.08 ± 1.38 |
| nzECM | 9.83 ± 1.08 | 11.60 ± 1.04 | 13.72 ± 1.19 | 17.61 ± 1.80 |
| mECM | 9.83 ± 1.08 | 13.73 ± 1.21 | 16.65 ± 1.07 | 20.95 ± 1.20 |
| Saline | 9.83 ± 1.08 | 13.37 ± 1.77 | 16.88 ± 2.62 | 20.07 ± 4.36 |
| *End-Systolic Area* | | | | |
| hzECM | 4.24 ± 0.79 | 5.41 ± 0.39 | 7.72 ± 1.41 | 9.33 ± 0.90 |
| nzECM | 4.24 ± 0.79 | 6.49 ± 0.76 | 7.51 ± 0.84 | 10.96 ± 1.40 |
| mECM | 4.24 ± 0.79 | 7.48 ± 0.55 | 10.64 ± 0.94 | 14.67 ± 1.03 |
| Saline | 4.24 ± 0.79 | 8.05 ± 1.52 | 11.48 ± 2.29 | 15.04 ± 3.62 | zECM Amends Elasticity of the Infarcted Myocardium.

Figure 6B:
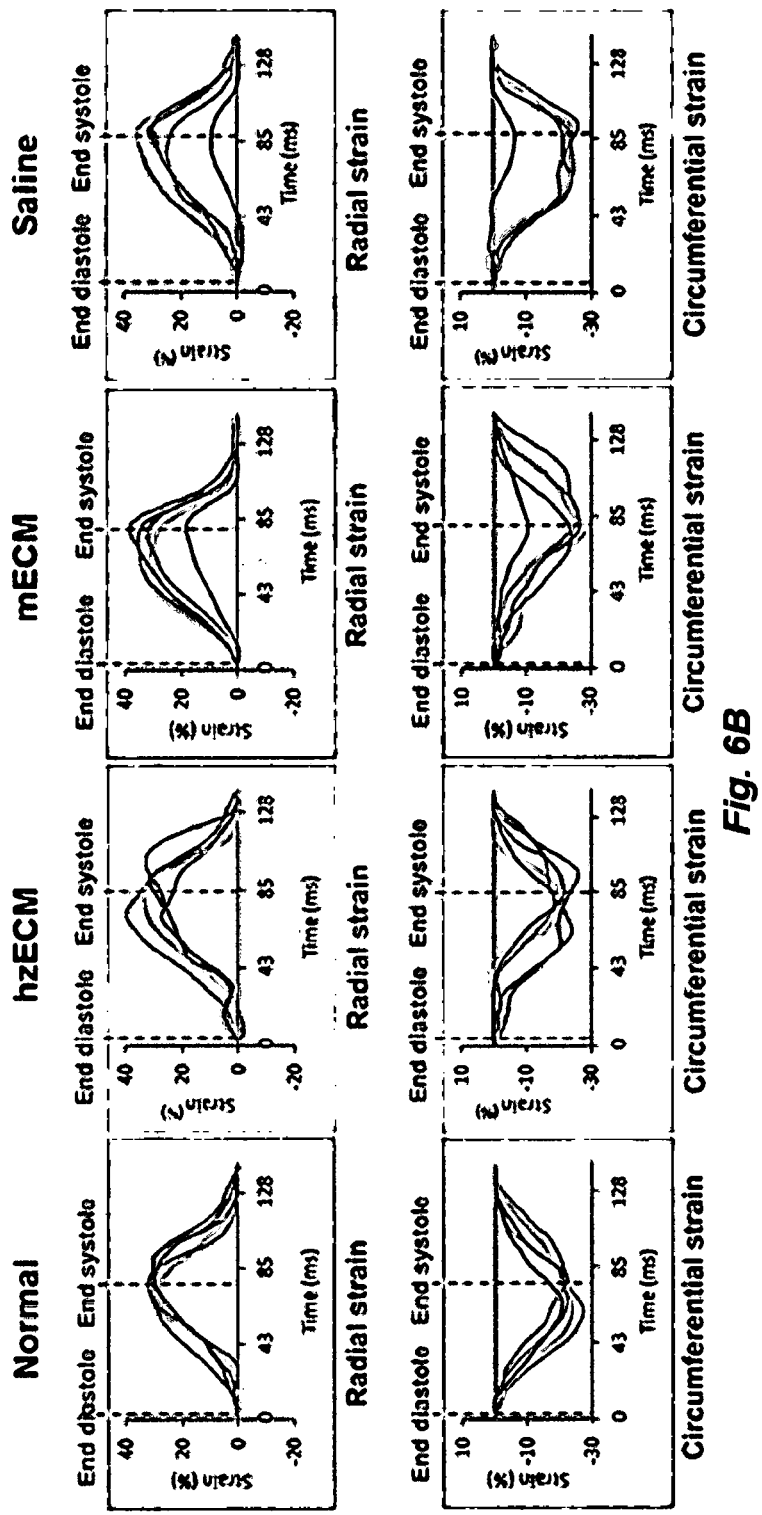

To understand the effect of zECM on the ventricular elasticity in the ischemic heart, myocardial strain analysis was performed at 6 weeks post-MI. The data revealed that zECM-treated myocardium had similar intercardiac strain (defined as Δ(end-diastole & end-systole)×100%) as the non-infarcted counterparts while mECM- and saline-treated ones were substantially stiffer. The strain of the infarcted myocardium was estimated by normalizing the spatially averaged axial strain in the infarcted area (A) to that of 4 non-infarct areas (B, C, D, and E) in left ventricular walls during a cardiac cycle (FIG. 6A), using VevoStrain cardiac strain analysis (FIG. 6B). Both hzECM (all p<0.001) and nzECM (all p<0.001) had substantially greater normalized radial (FIG. 6C) and circumferential (FIG. 6D) strains than mECM and saline. mECM showed moderately increased radial and circumferential strains (both p<0.01) than saline. No significant difference was observed between hzECM and nzECM (both p>0.05) hzECM exhibited the highest strains in both directions among all groups with no statistical difference from normal hearts (both p>0.05). These data suggest the effectiveness of zECM, but not mECM, in preserving or restoring left ventricular myocardial elasticity after MI.

zECM Promotes Structural Preservation in the Infarcted Heart.

H&E staining on serially sectioned mouse hearts revealed that zECM treatment alters pathological remodeling post-MI (FIG. 7A). Left ventricular chambers in both zECM-treated groups are notably smaller with less infarct area (FIG. 7B) and thicker ventricular walls (FIG. 7C) than those in mECM and saline groups. In zECM-treated groups, Masson's trichrome staining and anti-mouse CD68 staining at 6 weeks post-MI showed no increase in fibrotic scar (FIG. 8A) and chronic inflammation (FIG. 8B) respectively due to species difference. Consistent with the reduction of the infarct size, elastin is preserved locally at the infarct area in zECM-treated groups (FIG. 9A). We detected a significantly higher level of elastin in both zECM groups, hzECM in particular, than mECM and saline groups (FIG. 9B).

zECM Increases Proliferation of Mammalian Cardiac Precursor Cell Populations In Vivo.

Figure 10A:
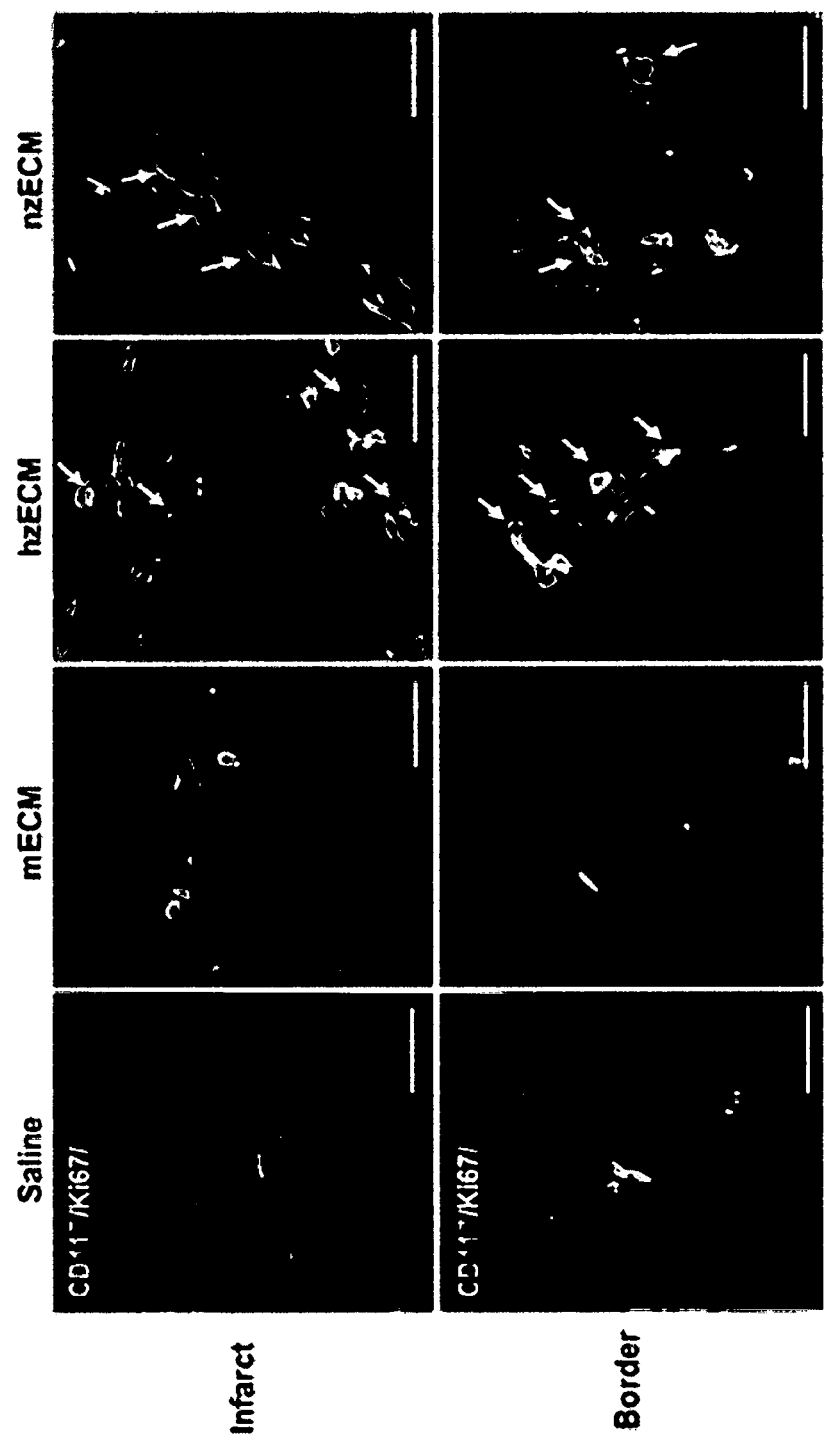
Figure 10D:
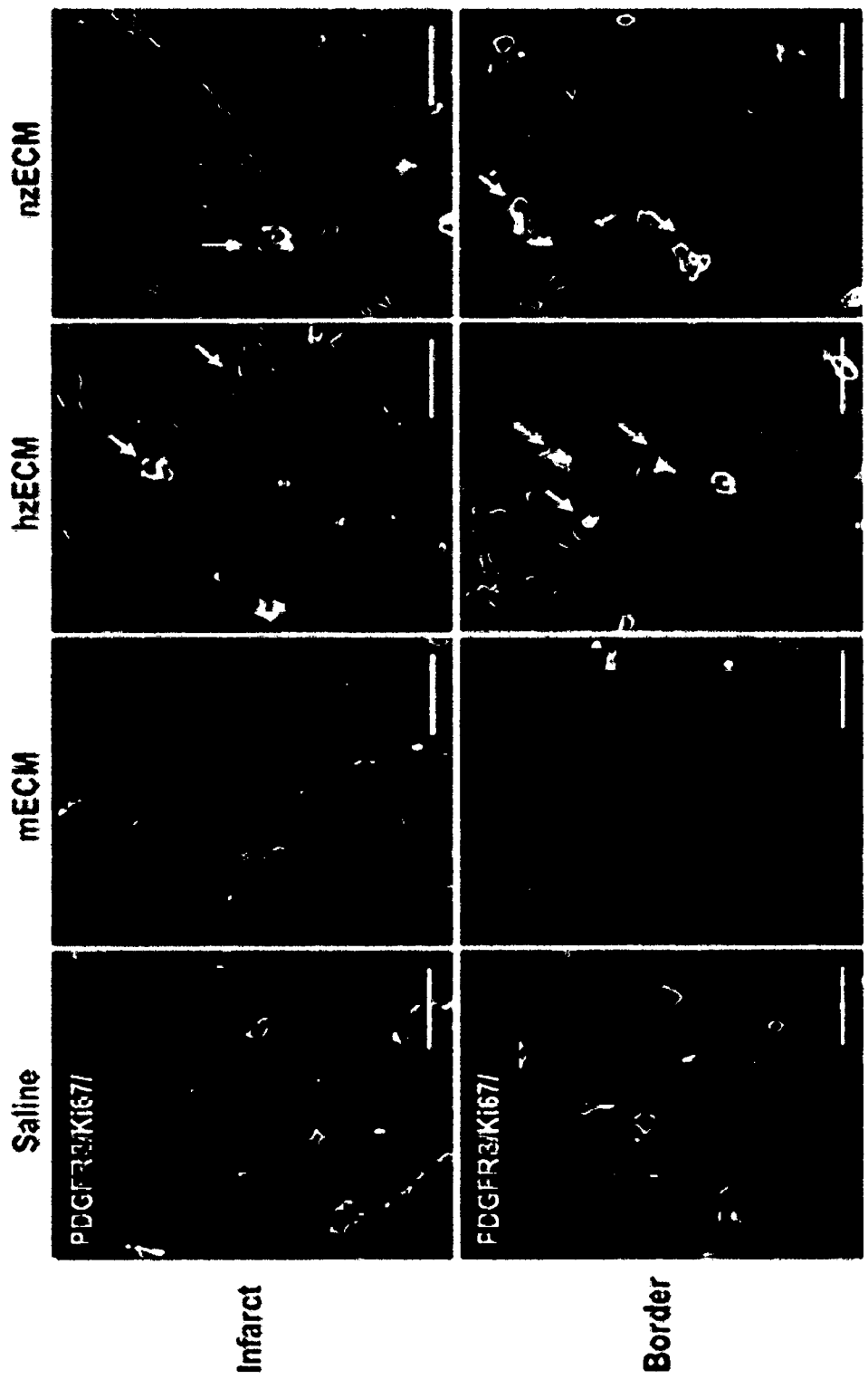
Figure 10B:
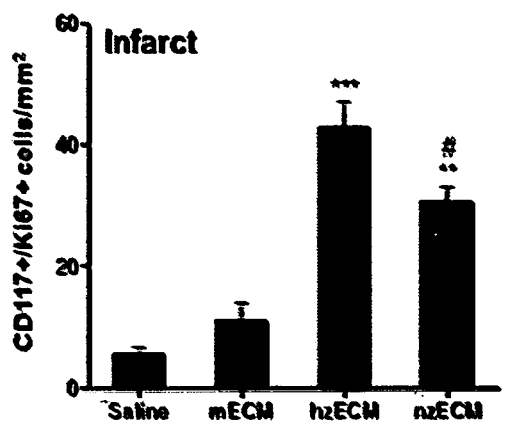
Figure 10C:
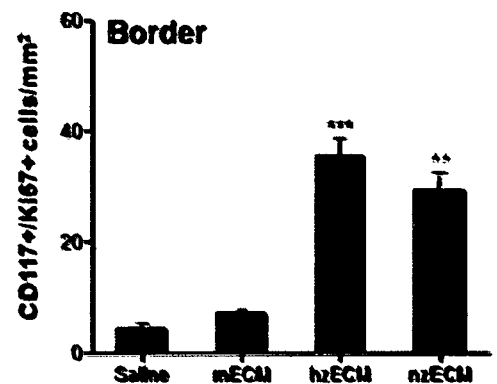
Figure 10E:
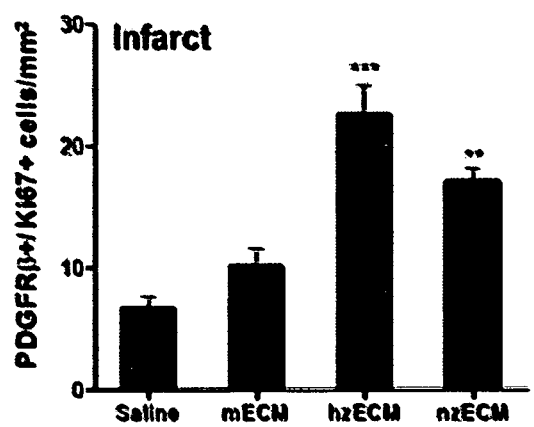
Figure 10F:
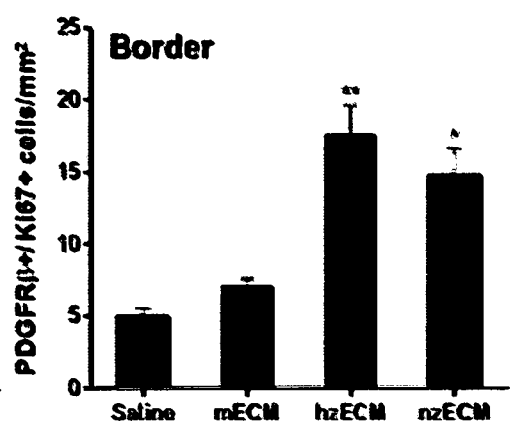
Figure 10G:
Figure 10H:
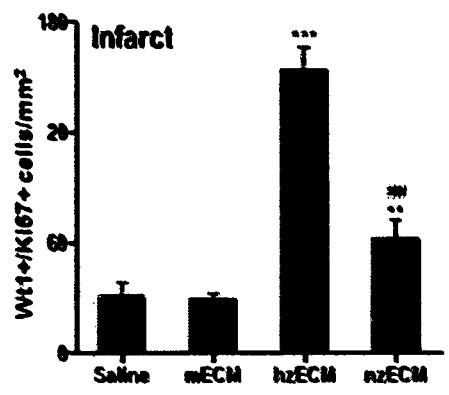

It was investigated whether the differences in functional outcomes of zECM and mECM treatment correlate with distinctive regenerative responses in the ischemic myocardium Immunohistochemistry at 6 weeks post-MI showed that all zECM-treated hearts had significantly higher numbers of c-kit+/Ki67+ proliferating murine cardiac stem cells (mCSC) than mECM- and saline-treated ones at the infarct and peri-infarct areas (c-kit: stem cell growth factor receptor or CD117; Ki67: a cellular proliferation marker) (FIGS. 10A-10C) hzECM-treated hearts exhibited markedly more platelet-derived growth factor receptor (PDGFR)-β+/Ki67+ proliferating cardiac MSC (cMSC) than mECM- and saline-treated hearts; nzECM-treated hearts contained more proliferating cMSC than saline-treated ones at the infarct and peri-infarct areas (FIGS. 10D-10F). Activation of Wilms tumor protein (Wt)-1+/Ki67+ proliferating epicardium-derived progenitor cells (EPDC) was observed only at the epicardium of the infarct (FIG. 10G) hzECM-treated group had substantially more proliferating EPDC than all other groups; nzECM had notably more proliferating EPDC than mECM and saline (FIG. 10H).

zECM Augments Adult Mammalian Cardiomyocyte Proliferation in the Ischemic Myocardium.

Figure 11A:
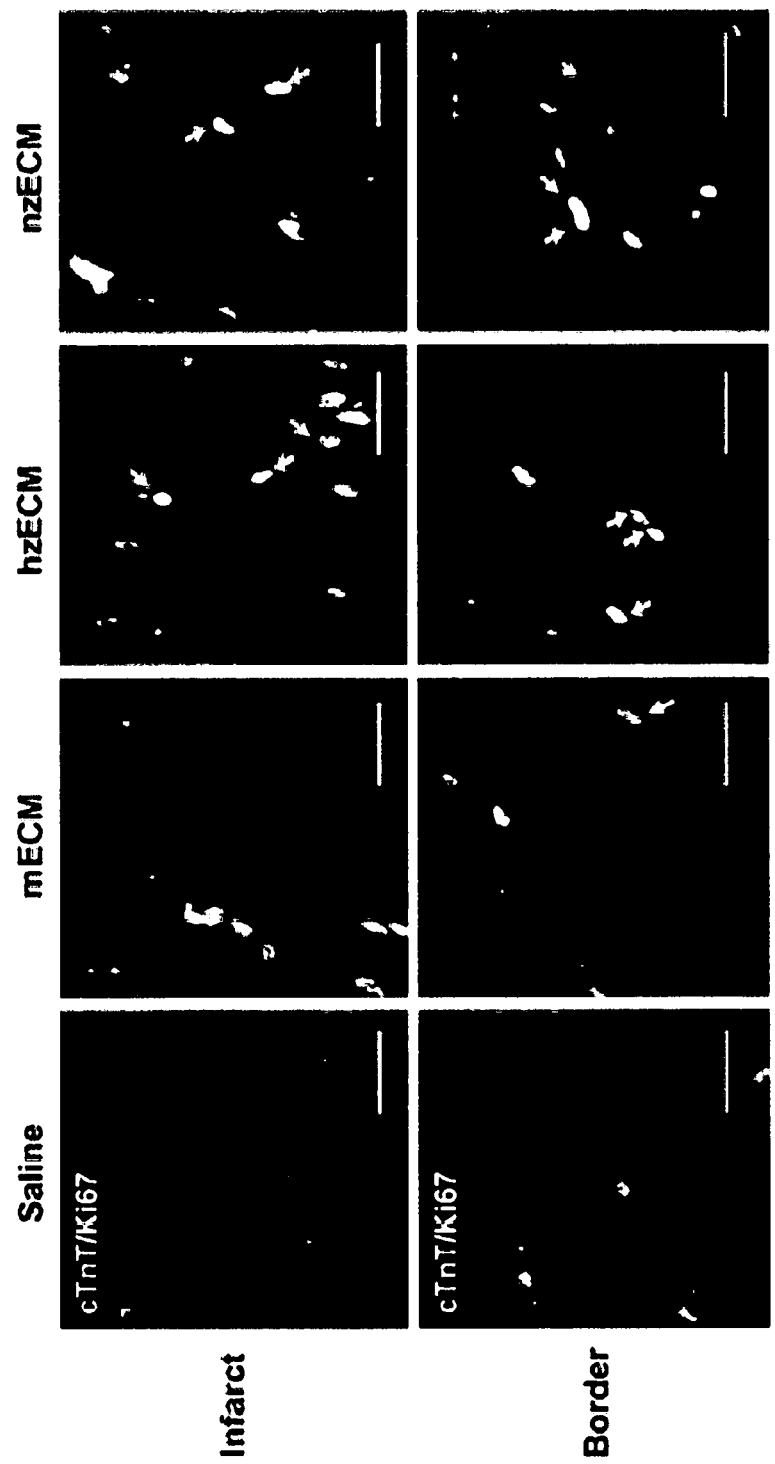
Figure 11B:
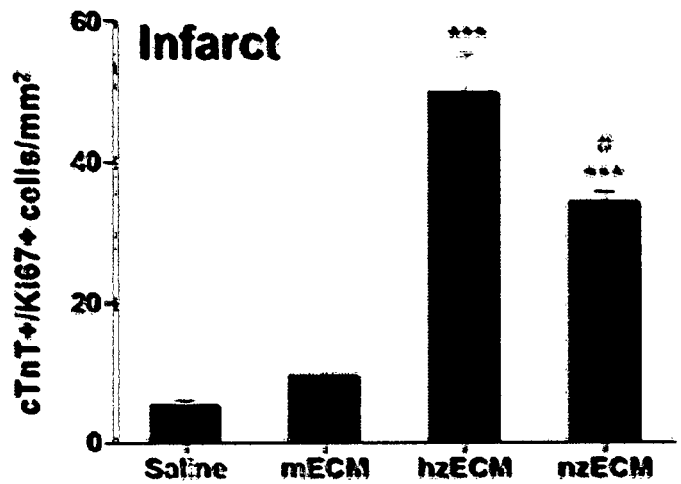
Figure 11C:
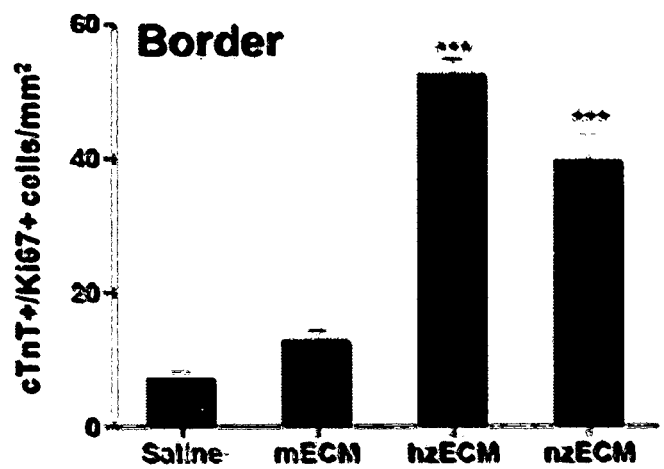
Figure 11D:
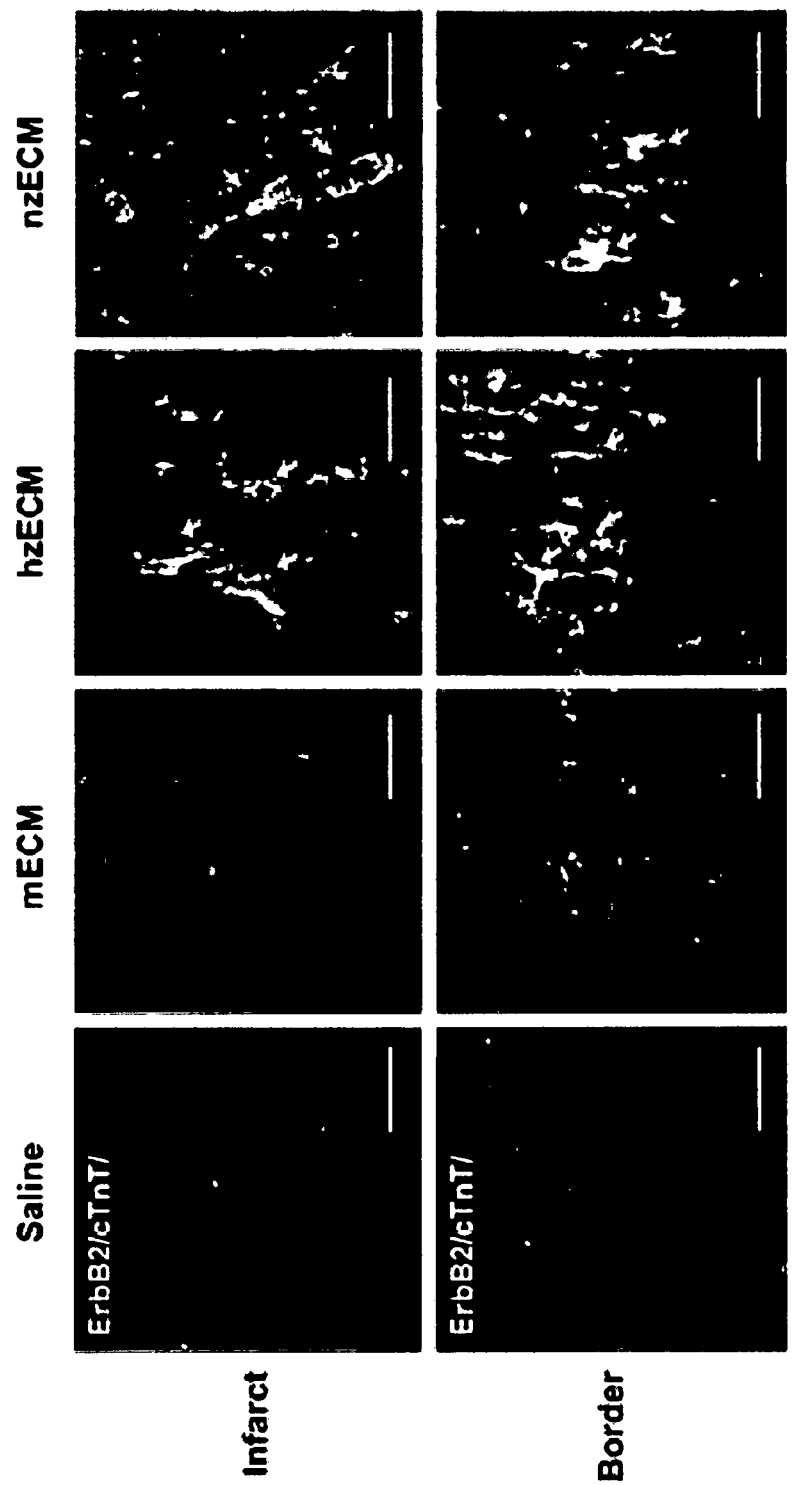
Figure 11E:
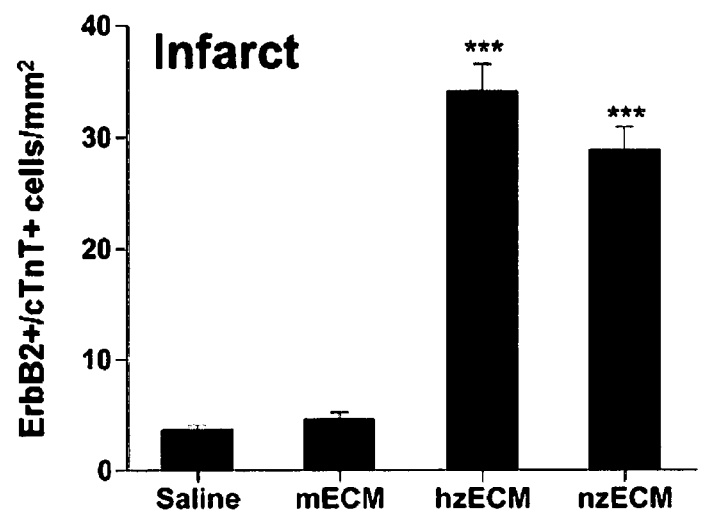
Figure 11F:
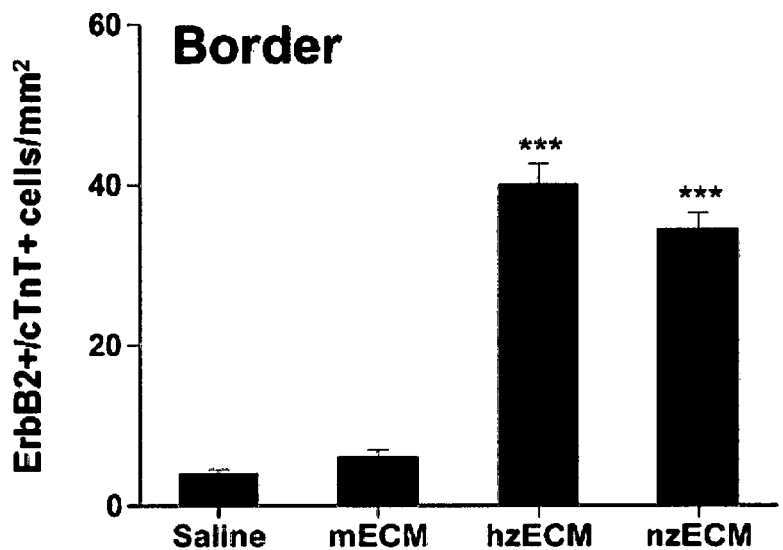

It was then examined whether the administration of zECM increases the host cardiomyocyte proliferation after the ischemic insult. Dual detection of cardiac troponin T (cTnT) and Ki67 at 3 days post-treatment revealed proliferation of adult mouse cardiomyocytes in zECM-treated animals (FIG. 11A). Image analyses showed that both zECM groups have notably higher numbers of cTnT+/Ki67+ proliferating cardiomyocytes than control groups at the infarct and peri-infarct areas (FIGS. 11B and 11C). hzECM had the highest cTnT+/Ki67+ cell number among all groups, especially at the infarct area (FIGS. 11B and 11C). In sharp contrast, cardiomyocyte proliferation is very limited in mECM and saline controls (FIGS. 11A-11C). Nevertheless, there are few cTnT+/Ki67+ cardiomyocytes in all four groups at 6 weeks post-MI (FIG. 12A-12C, all $p>0.05$), suggesting that a finite window of zECM treatment. This limited window may reduce the chance of hypertrophy and tumor development due to prolonged cell proliferation. On the other hand, healthy adult mouse hearts have little ErbB2 expression, which plays a significant role in mammalian heart regeneration [34]. However, at 3 days post-treatment, we observed the presence of ErbB2+/cTnT+ cardiomyocytes in both zECM-treated groups (FIG. 11D). hzECM and nzECM exhibited markedly larger presence of ErbB2+/cTnT+ cardiomyocytes than mECM and saline controls at the infarct and peri-infarct areas (FIGS. 11E and 11F), suggesting that zECM reactivates ErbB2 expression in adult mammalian cardiomyocytes post-MI.

Neuregulin-1, a Mitogen of Cardiomyocytes, is Present in zECM.

Figure 13A:
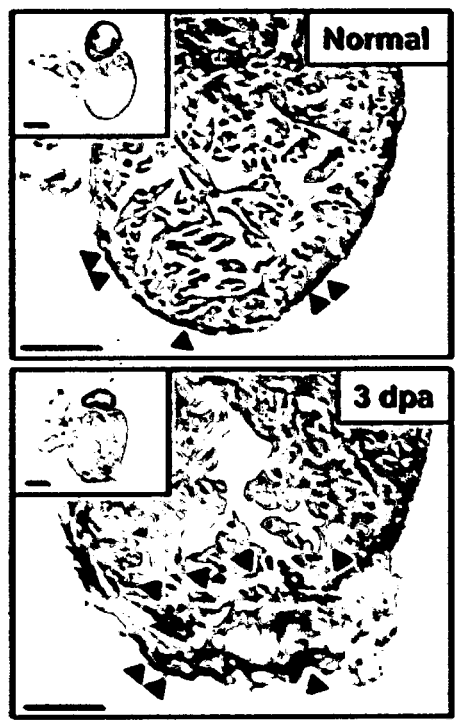
Figure 13B:
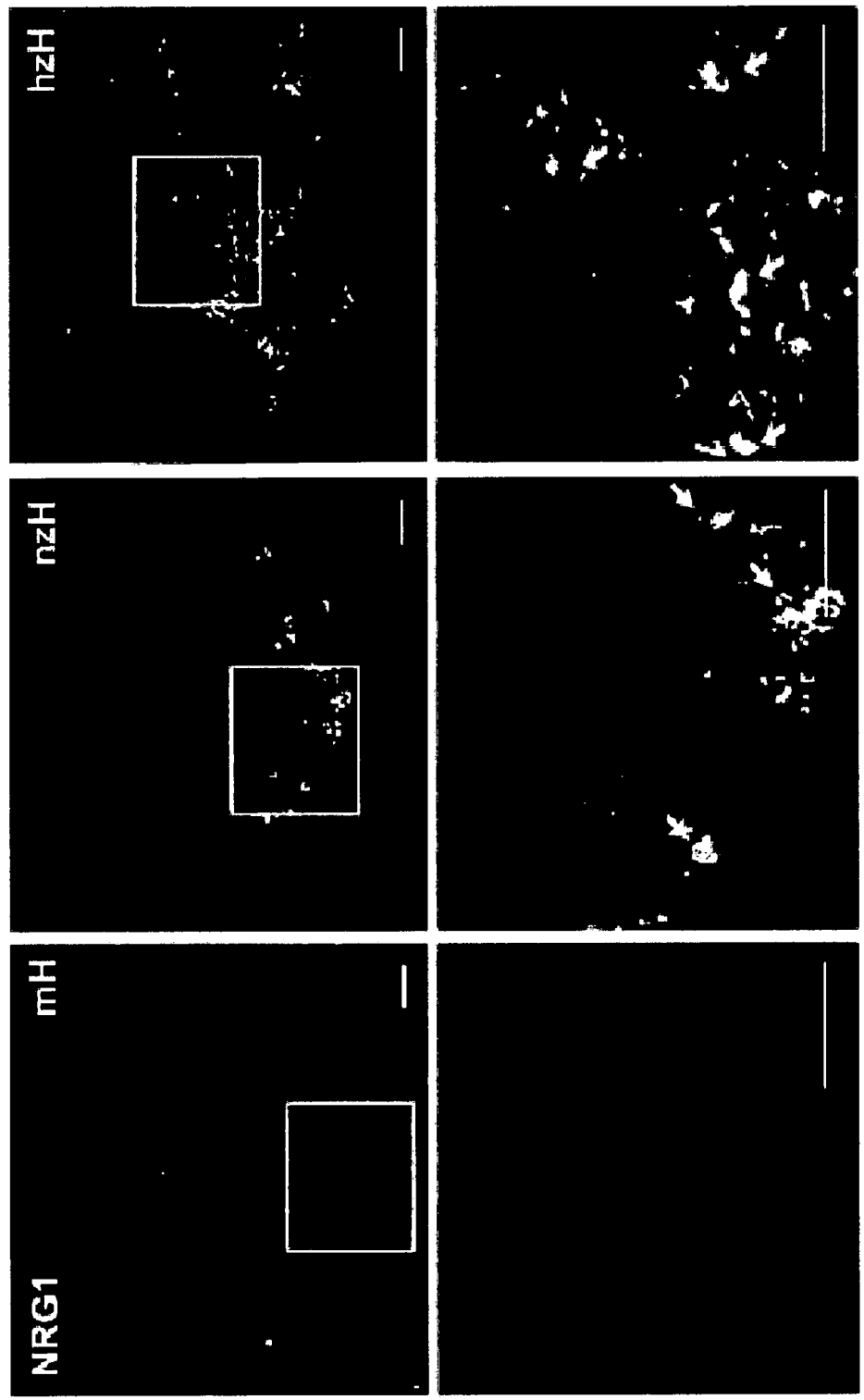
Figure 13C:
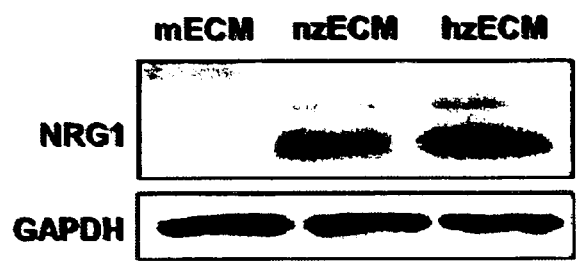
Figure 13D:
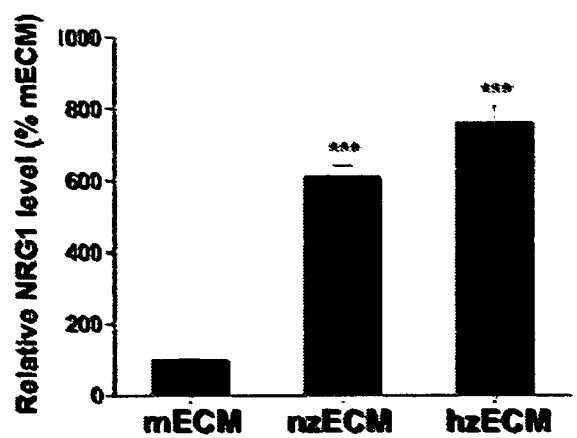

Neuregulin-1 (NRG1) is a mitogen capable of stimulating cardiomyocyte proliferation in regenerating zebrafish myocardium Immunohistochemical analysis showed that zebrafish hearts, especially the actively healing ones, express NRG1 (FIGS. 13A and 13B)), which is absent in adult mouse heart (FIG. 13B). Western blot analysis of NRG1 in all three ECM groups revealed the presence of NRG1 protein in both hzECM and nzECM (FIG. 13C). Quantification of Western blotting showed that hzECM and nzECM contain approximately 6.5 and 5 folds of NRG1 protein respectively when compared with mECM (FIG. 13D), both $p<0.001$).

Inhibiting ErbB2 Signaling Obliterates Beneficial Effects of zECM Treatment.

Figure 14B:
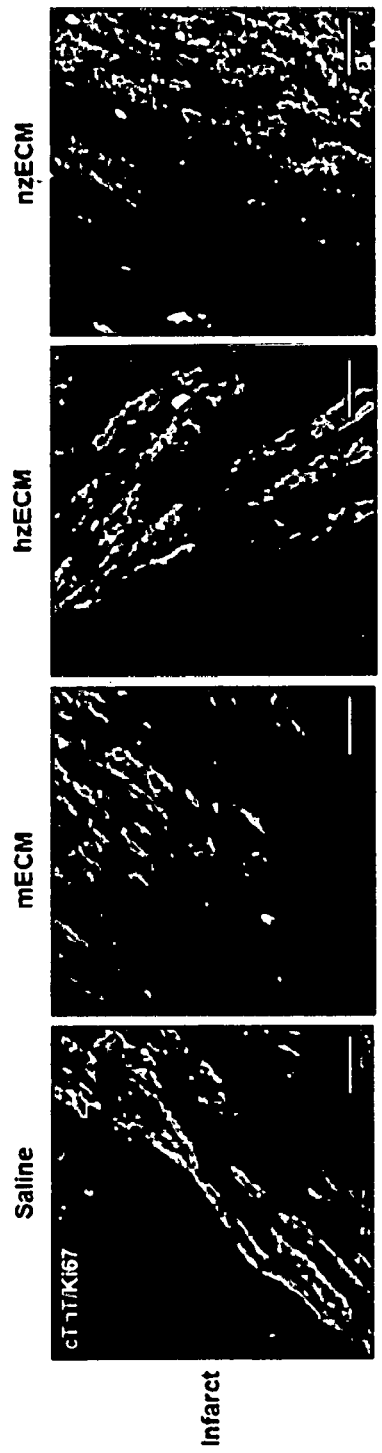
Figure 14D:
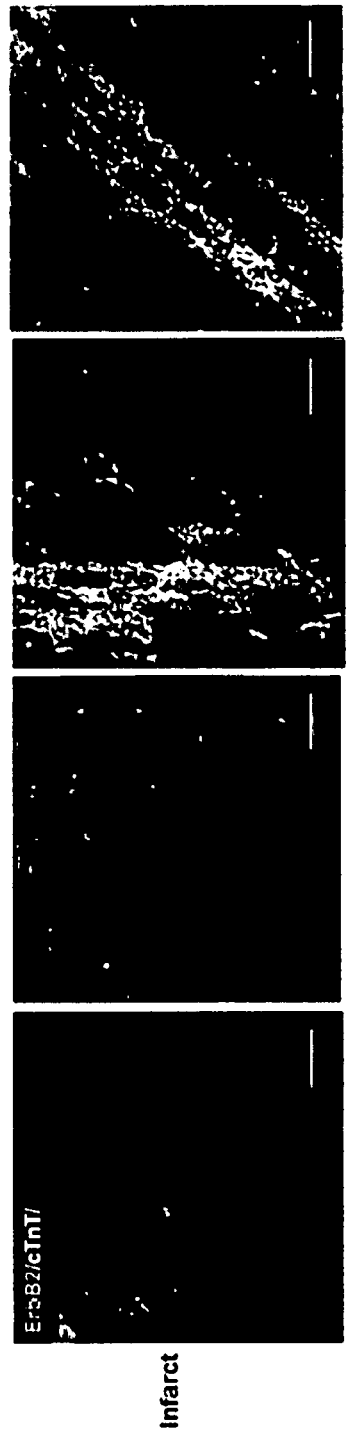
Figure 14C:
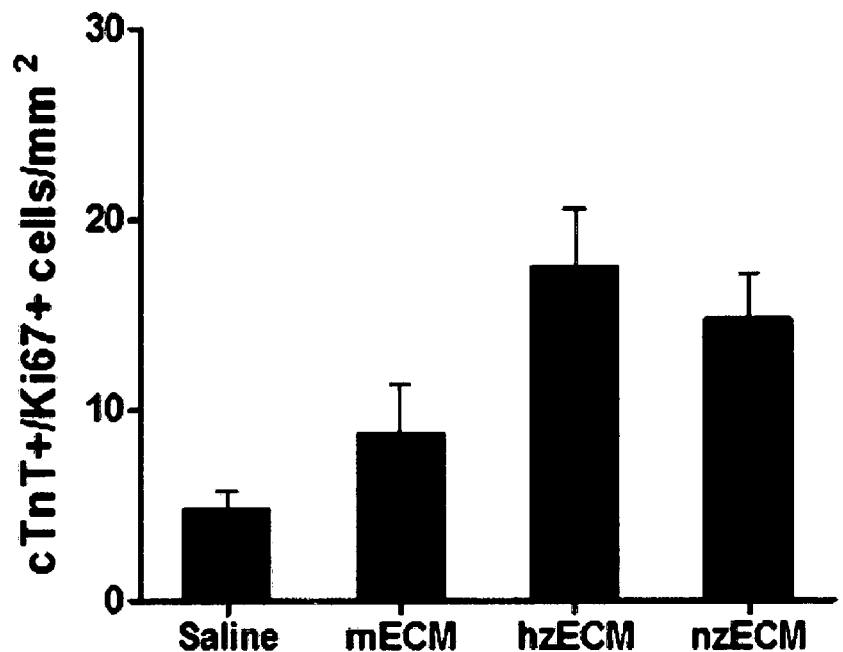
Figure 14E:
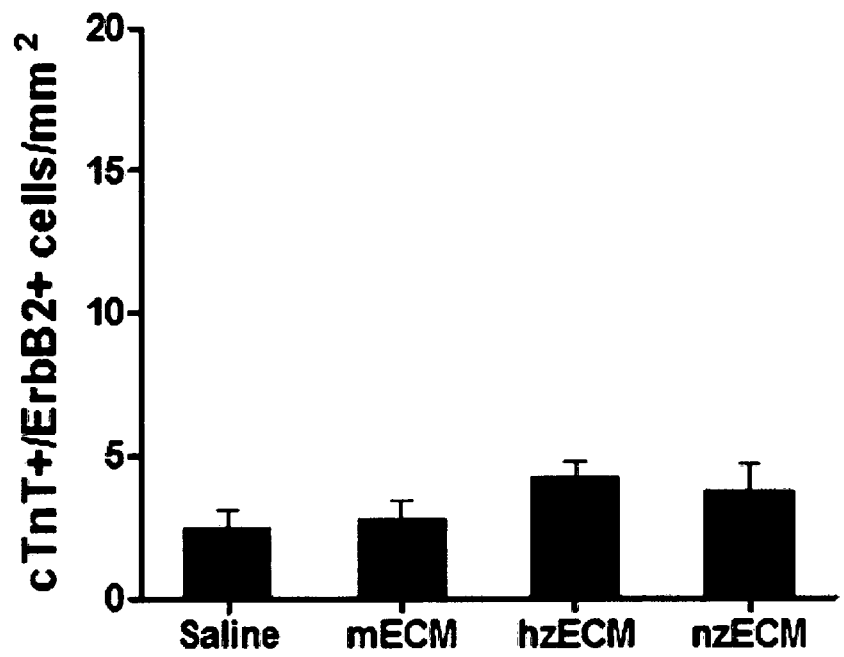

It was hypothesize that activation of ErbB2 signaling pathway by NRG1 in zECM plays a significant role in cardiac repair and regeneration observed in zECM-treated groups. To evaluate the importance of ErbB2 signaling in zECM-mediated therapeutic effects, zECM was injected intramyocardially after AMI while selectively inhibiting ErbB2 receptor kinase activity with a tyrphostin AG825 via intraperitoneal administration. Echocardiographic analyses showed that blocking ErbB2 signaling during zECM treatment renders zECM ineffective: it abolished the improvement of left ventricular contractility (FIG. 14A(A-B), both $p>0.05$) and eliminated the prevention of left ventricular dilatation (FIG. 14A(C-D), both $p>0.05$). All echocardiographic measurements are listed in Table 2. Dual immunofluorescent detection and quantification of c-kit+/Ki67+ proliferating mCSC at 3 days post-treatment exhibited no notable difference between all four groups (FIGS. 14B and 14C, $p>0.05$). Similarly, no significant difference in the number of ErbB2+/cTnT+ cardiomyocytes between all groups was observed following AG825 treatment (FIGS. 14D and 14E, $p>0.05$). These results suggest that ErbB2 mediates major effects of zECM, including zECM-induced functional recovery, activation of cardiac precursor cell proliferation, and reactivation of ErbB2 expression in adult cardiomyocytes.

TABLE 2

Echocardiographic parameters of infarcted mouse hearts following ECM treatment and ErbB2 inhibitor administration

| Mean ± SD (%) | 0 D | 5 D | 2 W | 6 W |
| --- | --- | --- | --- | --- |
| Fractional Area Change | | | | |
| hzECM | 57.12 ± 3.53 | 46.11 ± 4.21 | 38.16 ± 4.52 | 30.14 ± 4.55 |
| nzECM | 57.12 ± 3.53 | 44.37 ± 5.24 | 36.46 ± 6.71 | 29.18 ± 4.38 |
| mECM | 57.12 ± 3.53 | 42.37 ± 3.30 | 35.02 ± 3.47 | 27.45 ± 2.50 |
| Saline | 57.12 ± 3.53 | 39.48 ± 4.76 | 31.87 ± 3.68 | 25.16 ± 4.91 |
| Ejection Fraction | | | | |
| hzECM | 72.36 ± 2.24 | 60.44 ± 5.13 | 51.37 ± 5.95 | 43.49 ± 5.21 |
| nzECM | 72.36 ± 2.24 | 58.51 ± 5.32 | 49.35 ± 4.98 | 41.29 ± 2.83 |
| mECM | 72.36 ± 2.24 | 56.24 ± 2.11 | 47.63 ± 3.34 | 39.21 ± 3.44 |
| Saline | 72.36 ± 2.24 | 53.37 ± 4.33 | 43.76 ± 4.12 | 37.22 ± 5.65 |
| Mean ± SD (mm$^2$) | 0 D | 5 D | 2 W | 6 W |
| End-Diastolic Area | | | | |
| hzECM | 9.83 ± 1.08 | 13.39 ± 0.84 | 16.35 ± 1.28 | 19.50 ± 1.43 |
| nzECM | 9.83 ± 1.08 | 13.99 ± 1.12 | 16.71 ± 1.41 | 19.91 ± 1.95 |
| mECM | 9.83 ± 1.08 | 14.72 ± 1.04 | 17.45 ± 1.50 | 21.05 ± 1.17 |
| Saline | 9.83 ± 1.08 | 14.38 ± 1.58 | 17.85 ± 1.92 | 21.96 ± 2.25 |
| End-Systolic Area | | | | |
| hzECM | 4.24 ± 0.79 | 7.21 ± 0.43 | 10.11 ± 0.94 | 13.32 ± 1.10 |
| nzECM | 4.24 ± 0.79 | 7.78 ± 0.61 | 10.62 ± 1.41 | 13.96 ± 1.01 |
| mECM | 4.24 ± 0.79 | 8.49 ± 0.48 | 11.33 ± 0.53 | 15.27 ± 1.53 |
| Saline | 4.24 ± 0.79 | 9.13 ± 1.23 | 12.18 ± 1.72 | 15.93 ± 2.21 |

Although mammalian cardiomyocytes spontaneously proliferate at a very low rate throughout the adulthood, unlike the evolutionarily primitive zebrafish, adult mammalian hearts have very limited regenerative capacity after MI or other injuries involving massive loss of cardiomyocytes.

It was suspected that ECM contribute to this genus difference and hypothesize that ECM from a regenerable tissue, such as the zebrafish heart, can induce and/or facilitate adult mammalian heart regeneration after injury. Zebrafish and mice were used as representative species for lower vertebrates and mammals respectively. It was found that the composition of nzECM is significantly different from mECM with more elastin and GAGs and less collagen. Both hzECM and nzECM had significant pro-proliferative and chemotactic effects on human cardiac precursor cells, including hCSC and hHP, under stress in vitro while the efficacy of mECM was rather limited. The differences in the cellular proliferation and migratory rates suggest differential rescue and/or inductive capacities with each ECM treatment under deprived growth conditions.

Intramyocardial administration of decellularized cardiac ECM suspension showed that a single treatment of zECM, particularly hzECM, enables endogenous regeneration of murine heart tissue after AMI. Notably increased proliferation of multiple resident cardiac precursor cell populations was observed, including mCSC, cMSC, and EPDC, in both zECM groups. Furthermore, a fraction of remaining cardiomyocytes not only re-expressed ErbB2 but also proliferated after zECM treatment. These cellular regenerative responses following zECM induction contribute to the overall architectural preservation and structural regeneration, which correlates with approximately 61% recovery of cardiac ejection fraction (defined as [Δ(treatment−saline)/Δ(healthy−saline)]×100%). Under identical conditions, mECM yields only 17% functional recovery with limited improvement of myocardial elasticity and minimal proliferation of cardiac precursor cells and cardiomyocytes, consistent with literature reports on mammalian ECM in MI treatment [43, 44]. The data presented herein indicates a single intervention with zECM is sufficient to lead to significant improvement in cardiac output and remodeling as well as near-normal left ventricular wall motion. Altogether these results suggest the efficacy of zECM, especially hzECM, in the preservation and/or recovery of global cardiac milieu after MI.

zECM likely exerts its activities via multiple mechanisms in the ischemic myocardium, for example, the alteration of local ECM composition with increased elastin preservation and the release of incorporated inductive factor(s). The higher elastin content is consistent with greater myocardial strain and may augment cardiac stem/progenitor cell proliferation. In addition, it is possible that the altered ECM composition in the healing phase of amputated zebrafish heart partly contributes the highest regenerative efficacy of hzECM for ischemic mouse hearts. On the other hand, the presence of NRG1, a mitogen of cardiomyocytes and a ligand of ErbB2/ErbB4 complex, was detected in both hzECM and nzECM, but only minimally in mECM. NRG1 induces cardiomyocyte proliferation and myocardial regeneration in injured mammalian hearts, especially in neonates, largely via ErbB2/ErbB4 signaling pathways. The presence of NRG1 in zECM and the reactivation of its receptor ErbB2 in zECM-treated hearts are consistent with the observed proliferation of cardiomyocytes and improvement of cardiac function. Moreover, one intramyocardial zECM treatment yields significant functional recovery and structural change in infarcted hearts, in contrast to similar outcome yielded by daily systemic injections of recombinant NRG1 protein for 12 weeks. These results suggest the contribution of NRG1 in zECM-induced cardiomyocyte proliferation post-MI. However, a sufficient amount of NRG1-depleted zECM for testing could not be obtained due to the lethality of NRG1 deficiency in developing zebrafish. Thus, the NRG1-ErbB2 signaling axis was probed in the context of zECM administration by inhibiting ErbB2 activity.

ErbB2 signaling is essential in the survival, repair, growth, and regeneration of postnatal mammalian cardiomyocytes. Ventricular-restricted ErbB2-deficient mice exhibit phenotypes of dilated cardiomyopathy in their adulthood, indicated by decreased contractility, wall thinning, and chamber dilation. ErbB2 activation promotes dedifferentiation, proliferation, and hypertrophy of cardiomyocytes. To block ErbB2 signal transduction, AG825, a small molecule tyrphostin which selectively inhibits ErbB2 autophosphorylation nearly 60-fold more potently than ErbB1 (EGFR), was administered immediately following zECM treatment. Surprisingly, early ErbB2 inhibition not only obliterated the improvement of cardiac function but also eliminated the reduction of left ventricular dilatation in both hzECM and nzECM groups post-MI. These results are in agreement with previous findings showing notable deterioration in cardiac contractility of normal or diabetic murine hearts subjected to ischemia-reperfusion injury ex vivo after repeated intraperitoneal administration of AG825. Moreover, early ErbB2 inhibition fully prevented mCSC proliferation and ErbB2 reactivation in cardiomyocytes after zECM treatment. Together our data indicate the crucial role of ErbB2 signaling, both functionally and structurally, in likely all zECM-mediated benefits post-MI.

The substantially more proliferating cardiomyocytes in both zECM groups at 3 days, but not at 6 weeks, post-MI suggest a limited duration of zECM activities and possibly a finite therapeutic window for zECM-based intervention. This may reduce the risk of cardiac hypertrophy associated with unrestrained activation of NRG1/ErbB2 signaling. Local injection of zECM limits potential oncogenic risks associated with systemic growth factor administrations such as NRG1 treatment. The proliferation of multiple cardiac progenitors further indicates the broader biological activities of zECM beyond NRG1. Identification of other bioactive molecules within zECM could reveal additional pathways important to mammalian cardiac tissue regeneration. Test of zECM in large animal models of MI using a less invasive delivery method is under investigation. Additionally, it is possible that decellularized ECM from other primitive lifeforms can also promote the regeneration of mammalian heart and other organs with limited regenerative capability.

In conclusion, the current study demonstrated that decellularized cardiac ECM from zebrafish induces the proliferation of murine and human cardiac precursor cell populations and murine adult cardiomyocytes under stress and significantly augments cardiac function and myocardial elasticity post-MI. Decellularized adult mouse cardiac ECM only slightly promoted cardiac progenitor cell and cardiomyocyte proliferation under stress and marginally improved functional recovery and myocardial elasticity, as typically seen in previous approaches using mammalian ECM. Through the selective inhibition of ErbB2 activity, it was found that ErbB2 signaling, likely via NRG1 present in zECM, plays an indispensable role in zECM-mediated anatomical and functional improvement. Overall, these data demonstrated the potential of zECM as a new candidate to induce cardiac regeneration.

The following clauses provide aspects of the invention:
1. A method of producing regenerative extracellular matrix (rECM) composition, comprising:
   a. freezing and thawing tissue that has inherent regenerative capability or that is undergoing regeneration, growth, or development, to kill cells within the tissue;

b. treating the thawed tissue with one or more nucleases to digest nucleic acids in the tissue to produce rECM; and
c. washing the nuclease-digested tissue in an aqueous solution, to remove cellular debris.
2. The method of clause 1 wherein the rECM has not been subjected to a dialysis and/or a cross-linking process.
3. The method of clause 1, wherein the tissue is regenerating tissue.
4. The method of clause 1, wherein the tissue is obtained from an animal selected from the group consisting of: a fish, a lizard, an amphibian, an echinoderm, a planaria, or a hydra, and optionally the tissue is obtained from a lizard tail, a deer antler, a rabbit ear, a bat wing, a spiny mouse (*Acomys*) ear or skin, a land slug (*Prophysaon*), a sea snail (e.g., *Oxynoe panamensis*), an octopus, a cricket, a spider, a crab, a lobster, a salamander, a newt, a urodele, an axolotl (*Ambystoma mexicanum*), a zebrafish, a sea star, a sea urchin, a sea cucumber, an anemone, a planaria, or a hydra.
5. The method of any one of clauses 1-4, wherein the tissue is genetically-modified or is obtained from a genetically-modified organism.
6. The method of clause 4, wherein the tissue is a regenerative tissue.
7. The method of clause 6, wherein the tissue is prepared by damaging the tissue in the animal, and harvesting the tissue after regeneration begins but before regeneration ends.
8. The method of any one of clauses 1-7, wherein the rECM is in the form of a solid, a gel, or a solution.
9. The method of any one of clauses 1-8, wherein the tissue undergoing regeneration, growth, or development is treated with a red blood cell lysis solution and washed prior to treating the thawed tissue with one or more nucleases.
10. The method of any one of clauses 1-9 comprising washing the tissue in an aqueous solution at any point prior to or after any of a. or b.
11. The method of clause 10, wherein the aqueous solution is water, phosphate-buffered saline, or isotonic saline, optionally comprising one or more antibiotics.
12. The method of any one of clauses 1-11 wherein a. or b. is repeated one or more additional time, with a washing step in between repeated steps.
13. The method of any one of clauses 1-12, wherein the tissue or rECM composition is not dialyzed, digested with a protease, or cross-linked.
14. The method of any one of clauses 1-13, wherein the rECM composition is dried, e.g. lyophilized
15. The method of any one of clauses 1-14, further comprising:
c. digesting the nuclease-digested tissue with an acid protease.
16. The method of any one of clauses 1-15, wherein the regenerating tissue is normal or genetically-modified zebrafish heart tissue, optionally prepared by damaging the heart and harvesting the heart after regeneration begins but before regeneration ends.
17. The method of any one of clauses 1-16 further comprising, combining the rECM material with another extracellular matrix (ECM) material; a polymeric composition, such as a biodegradable polymer composition, such as a polyester including a polyglycolic acid (PGA), a polylactic acid (PLA), poly(lactic-co-glycolic acid) (PLGA), a polycaprolactine (PCL), a polyethyleneglycol (PEG)-derived biodegradable polymers, poly (glycerol sebacate) (PGS), or a polyurethane, a poly(ester urethane) urea (PEUU), poly(ether ester urethane)urea (PEEUU), a poly(ester carbonate)urethane urea (PECUU) or a poly(carbonate)urethane urea (PCUU); and/or a medical device or apparatus, such as a woven or nonwoven material, a fiber, and/or a prosthetic.
18. The method of any one of clauses 1-17 wherein the rECM is deposited onto a surface.
19. The method of clause 17, wherein the rECM is combined with a polymer or combination of polymers.
20. The method of clause 19, wherein the rECM is sprayed, spun, electrosprayed or electrospun, and is optionally co-deposited with a polymeric composition such as a polyglycolic acid (PGA), a polylactic acid (PLA), poly(lactic-co-glycolic acid) (PLGA), a polycaprolactine (PCL), a polyethyleneglycol (PEG)-derived biodegradable polymers, poly (glycerol sebacate) (PGS), a polyester, a poly(ester urethane) urea (PEUU), poly(ether ester urethane)urea (PEEUU), a poly(ester carbonate)urethane urea (PECUU) or a poly(carbonate)urethane urea (PCUU).
21. The method of any one of clauses 1-20, wherein the rECM material is deposited onto a surface of a bandage.
22. A method of treating a patient having a tissue injury, condition or defect, comprising administering to the patient an amount of an rECM composition to the patient at a location in the patient of tissue injury, condition or defect, in an amount effective to treat the tissue injury, condition or defect in the patient.
23. The method of clause 22, wherein the rECM composition is prepared according to the method of any one of clauses 1-20.
24. The method of clause 22, wherein the tissue injury, condition or defect is tissue trauma, and the rECM is administered to the patient at or near the tissue trauma.
25. The method of clause 22, wherein the condition is a myocardial infarction, a ischemia/reperfusion injury, a congenital myocardial or outflow tract defect, or a condition involving loss of or reduced amount of myocardial tissue, and the rECM is injected into or adjacent to the infarction, injury site, or defect location.
26. The method of clause 22, wherein the rECM is prepared from regenerating normal or genetically-modified zebrafish heart tissue.
27. The method of any one of clauses 22-26, wherein the tissue is obtained from a lizard tail, a deer antler, a rabbit ear, a bat wing, a spiny mouse (*Acomys*) ear or skin, a land slug (*Prophysaon*), a sea snail (e.g., *Oxynoe panamensis*), an octopus, a cricket, a spider, a crab, a lobster, a salamander, a newt, a urodele, an axolotl (*Ambystoma mexicanum*), a zebrafish, a sea star, a sea urchin, a sea cucumber, an anemone, a planaria, or a hydra, and/or a genetically modified organism or tissue.
28. Regenerative extracellular matrix (rECM), prepared according to the method of any one of clauses 1-21.
29. The rECM of clause 28, combined with a different ECM material and/or a polymeric material.
30. The rECM of clause 29, combined with a biodegradable polymeric material, such as a polyglycolic acid (PGA), a polylactic acid (PLA), poly(lactic-co-glycolic acid) (PLGA), a polycaprolactine (PCL), a polyethyleneglycol (PEG)-derived biodegradable polymers, poly (glycerol sebacate) (PGS), a polyester, poly(ester urethane) urea (PEUU), poly(ether ester urethane)urea (PEEUU), a poly(ester carbonate)urethane urea (PECUU) or a poly(carbonate)urethane urea (PCUU).

31. The rECM of clause 28, prepared as a reverse-gelling composition.

32. A medical device or apparatus comprising or coated with an rECM material or any one of clauses 28-31 or prepared according to a method of any one of clauses 1-21.

33. A method of preparing an rECM gel material comprising neutralizing an acid protease-digested material that is prepared by:
  a. freezing and thawing tissue that has inherent regenerative capability or that is undergoing regeneration, growth, or development, to kill cells within the tissue;
  b. treating the thawed tissue with one or more nucleases to digest nucleic acids in the tissue to produce rECM;
  c. washing the nuclease-digested tissue in an aqueous solution, to remove cellular debris;
  d. digesting the nuclease-digested tissue with an acid protease; and
  e. optionally freezing or lyophilizing the acid protease-digested material.

34. The method of clause 33, wherein a., b., and c. are performed according to any one of clauses 2-20.

35. A kit comprising rECM or rECM combined with other materials contained in a vessel.

36. The kit of clause 35, wherein the rECM is prepared according to any one of clauses 1-21 or 33.

Having described this invention, it will be understood to those of ordinary skill in the art that the same can be performed within a wide and equivalent range of conditions, formulations and other parameters without affecting the scope of the invention or any embodiment thereof.

What is claimed is:

1. A method of producing regenerative extracellular matrix (rECM) composition, comprising:
  obtaining tissue that has inherent regenerative capability, or that is undergoing regeneration, growth, or development, from an animal selected from the group consisting of: a lizard, an echinoderm, a planarian, a hydra, a bat, a spiny mouse, a land slug, a sea snail, an octopus, a cricket, a spider, a crab, a lobster, a zebrafish, or an anemone;
  freezing and thawing the tissue that has inherent regenerative capability or that is undergoing regeneration, growth, or development, to kill cells within the tissue;
  treating the tissue with one or more nucleases to digest nucleic acids in the tissue to produce rECM; and
  washing the nuclease-digested tissue in a solution, to remove cellular debris.

2. The method of claim 1 wherein the rECM has not been subjected to a dialysis and/or a cross-linking process.

3. The method of claim 1, wherein the tissue is regenerating tissue.

4. The method of claim 1, wherein the tissue is genetically modified.

5. The method of claim 1, wherein the tissue is a regenerative tissue, and optionally the tissue is prepared by damaging the tissue in the animal and harvesting the tissue after regeneration begins but before regeneration ends.

6. The method of claim 1, wherein the rECM is in the form of a solid, a gel, or a solution.

7. The method of claim 1, wherein the tissue undergoing regeneration, growth, or development is treated with a red blood cell lysis solution and washed prior to treating the tissue with one or more nucleases.

8. The method of claim 1, further comprising:
  digesting the nuclease-digested tissue with an acid protease.

9. The method of claim 1, further comprising combining the rECM material with:
  another extracellular matrix (ECM) material;
  a biodegradable polymer composition, comprising a polyester including a polyglycolic acid (PGA), a polylactic acid (PLA), poly(lactic-co-glycolic acid) (PLGA), a polycaprolactine (PCL), a polyethyleneglycol (PEG)-derived biodegradable polymers, poly (glycerol sebacate) (PGS), and/or a polyurethane, a poly(ester urethane) urea (PEUU), poly(ether ester urethane)urea (PEEUU), a poly(ester carbonate)urethane urea (PECUU), and/or a poly(carbonate)urethane urea (PCUU); and/or
  a medical device or apparatus comprising a woven or nonwoven material, a fiber, and/or a prosthetic.

10. The method of claim 1, further comprising spraying, spinning, electrospraying, or electrospinning the rECM, and optionally co-depositing the rECM with a polymeric composition comprising a polyglycolic acid (PGA), a polylactic acid (PLA), poly(lactic-co-glycolic acid) (PLGA), a polycaprolactine (PCL), a polyethyleneglycol (PEG)-derived biodegradable polymers, poly (glycerol sebacate) (PGS), a polyester, a poly(ester urethane) urea (PEUU), poly(ether ester urethane)urea (PEEUU), a poly(ester carbonate)urethane urea (PECUU) and/or a poly(carbonate)urethane urea (PCUU).

11. Regenerative extracellular matrix (rECM), prepared according to the method of claim 1.

12. The rECM of claim 11, combined with a biodegradable polymeric material, comprising a polyglycolic acid (PGA), a polylactic acid (PLA), poly(lactic-co-glycolic acid) (PLGA), a polycaprolactine (PCL), a polyethyleneglycol (PEG)-derived biodegradable polymers, poly (glycerol sebacate) (PGS), a polyester, poly(ester urethane) urea (PEUU), poly(ether ester urethane)urea (PEEUU), a poly (ester carbonate)urethane urea (PECUU), and/or a poly (carbonate)urethane urea (PCUU).

13. The rECM of claim 11, prepared as a reverse-gelling composition.

14. A medical device or apparatus comprising or coated with an rECM material prepared according to claim 1.

* * * * *

UNITED STATES PATENT AND TRADEMARK OFFICE
CERTIFICATE OF CORRECTION

| | |
|---|---|
| PATENT NO. | : 11,331,348 B2 |
| APPLICATION NO. | : 16/096400 |
| DATED | : May 17, 2022 |
| INVENTOR(S) | : Chien-Wen Chen et al. |

It is certified that error appears in the above-identified patent and that said Letters Patent is hereby corrected as shown below:

In the Claims

Column 36, Line 19, Claim 9, delete "polycaprolactine" and insert -- polycaprolactone --

Column 36, Lines 32-33, Claim 10, delete "polycaprolactine" and insert -- polycaprolactone --

Column 36, Line 45, Claim 12, delete "polycaprolactine" and insert -- polycaprolactone --

Signed and Sealed this
Twentieth Day of September, 2022

Katherine Kelly Vidal
*Director of the United States Patent and Trademark Office*